US006689757B1

(12) United States Patent
Craig

(10) Patent No.: US 6,689,757 B1
(45) Date of Patent: Feb. 10, 2004

(54) METHODS FOR VACCINATION AND VACCINES THEREFOR

(75) Inventor: Roger K. Craig, Cheshire (GB)

(73) Assignee: M.L. Laboratories PLC, London (GB)

(*) Notice: Subject to any disclaimer, the term of this patent is extended or adjusted under 35 U.S.C. 154(b) by 0 days.

(21) Appl. No.: 09/221,050

(22) Filed: Dec. 28, 1998

Related U.S. Application Data

(63) Continuation-in-part of application No. 09/022,614, filed on Feb. 12, 1998, now abandoned, which is a continuation of application No. 08/861,283, filed on May 21, 1997, now abandoned, which is a continuation-in-part of application No. 08/800,079, filed on Feb. 12, 1997, now abandoned.
(60) Provisional application No. 60/024,116, filed on Aug. 16, 1996, and provisional application No. 60/016,506, filed on Apr. 30, 1996.

(30) Foreign Application Priority Data

Feb. 12, 1996 (GB) .............................. 9602777
Jul. 11, 1996 (GB) .............................. 9614548

(51) Int. Cl.[7] .................. A61K 48/00; C12N 15/00; C12N 15/63
(52) U.S. Cl. ................ 514/44; 514/2; 435/370.1; 435/325; 435/455; 530/300; 530/350; 424/93.2; 424/93.21
(58) Field of Search ............... 514/44, 2; 424/93.2, 424/93.21; 435/325, 320.1, 455; 530/300, 350

(56) References Cited

U.S. PATENT DOCUMENTS

| | | | |
|---|---|---|---|
| 3,791,932 A | 2/1974 | Schuurs et al. | 435/7.8 |
| 3,949,064 A | 4/1976 | Bornstein et al. | 436/527 |
| 4,174,384 A | 11/1979 | Ullman et al. | 436/537 |
| 4,868,116 A | 9/1989 | Morgan et al. | 435/456 |
| 4,980,286 A | 12/1990 | Morgan et al. | 435/371 |
| 5,166,320 A | 11/1992 | Wu et al. | 530/395 |
| 6,300,090 B1 * | 10/2001 | Steinman et al. | 435/7.24 |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 92/07573 | 5/1992 |
| WO | WO 94/12629 | 6/1994 |
| WO | WO 94/21806 | 9/1994 |
| WO | WO 95/05853 | 3/1995 |
| WO | WO 95/08635 | 3/1995 |
| WO | WO 96/41606 | 12/1996 |

OTHER PUBLICATIONS

Yasutomi et al. (1995) J. Virol., vol. 69 (4); 2279–2284, Apr. 1995.*
Verma et al. (1997) Science, vol. 389; 239–242, 1997.*
Marshall et al. (1995) Science, vol. 269; 1050–1055, 1995.*
Orkin et al. (1995) "Report and Recommendations of the Panel to Assess the NIH Investment in Research on Gene Therapy", 1995.*
Alijagic et al., Eur. J. Immunol., 1995, 25, 3100–3107.
Armentano et al., Proc. Natl. Acad. Sci. USA, 1990, 87, 6141–6145.
Antoniou et al., EMBO J., 1988, 7, 377–384.
Barry et al., Nature, 1995, 377, 632–635.
Berkner et al., BioTechniques, 1988, 6, 616–629.
Blobel et al., J. Cell Biol., 1975, 67, 852–862.
Carson et al., Nucl. Acids Res., 1993, 21(9), 2065–2072.
Chiang et al., Proc. Natl. Acad. Sci. USA, 1992, 89, 5799–5803.
Chowdhury et al., Science, 1991, 254, 1802–1805.
Cristiano et al., Proc. Natl. Acad. Sci. USA, 1993, 90, 2122–2126.
Curiel et al., Proc. Natl. Acad. Sci. USA, 1991, 88, 8850–8854.
Dai et al., Proc. Natl. Acad. Sci. USA, 1992, 89, 10892–10895.
Danos et al., Proc. Natl. Acad. Sci. USA, 1988, 85, 6460–6464.
Dawson et al., Biochim. et Biophy. Acta, 1978, 510, 75–86.
Donivan, Nature, 1987, 326, 331–332.
Eglitis et al., Science, 1985, 230, 1395–1398.
Ferry et al., Proc. Natl. Acad. Sci. USA, 1991, 88, 8377–8381.
Flotte et al., Am. J. Respir. Cell Mol. Biol., 1992, 7, 349–356.
Flotte et al., J. Biol. Chem., 1993, 268, 3781–3790.
Gordon et al., Curr. Topics Microbiol. Immunol., 1992, 181, 1–37.
Grosveld et al., Cell, 1987, 51, 975–985.
Hermonat et al., Proc. Natl. Acad. Sci. USA, 1984, 81, 6466–6470.
Herz et al., Proc. Natl. Acad. Sci. USA, 1993, 90, 2812–2816.
Huber et al., Proc. Natl. Acad. Sci. USA, 1991, 88, 8039–8043.
Hwu et al., J. Immunol., 1993, 150, 4104–4115.
Kay et al., Human Gene Therapy, 1992, 3, 641–647.
Kollias et al., Cell, 1986, 46, 89–94.
Krieg et al., Nature, 1995, 374, 546–549.
Krysan et al., Mol. Cell Biol., 1989, 9, 1026–1033.
Lemarchand et al., Proc. Natl. Acad. Sci. USA, 1992, 89, 6482–6486.

(List continued on next page.)

Primary Examiner—Anne M. Wehbe'
(74) Attorney, Agent, or Firm—Cozen O'Connor, P.C.

(57) ABSTRACT

The invention relates to methods of and compositions for vaccinating a mammal against a disease, wherein a mixture is administered which includes (i) a nucleic acid which encodes a first epitope and (ii) a peptide containing a second epitope such that both of the nucleic acid and the second epitope are taken up by and the nucleic acid is expressed in a professional antigen presenting cell of the mammal, and the first and second epitopes are processed in the cell such that an immune response is elicited in the mammal to the epitopes.

53 Claims, 27 Drawing Sheets

OTHER PUBLICATIONS

Levitskaya et al., *Nature*, 1995, 375, 685–688.
MacGregor et al., *Nucl. Acids Res.*, 1989, 17, 2365.
Magram et al., *Nature*, 1985, 315, 338–340.
McLaughlin et al., *J. Virol.*, 1988, 62, 1963–1973.
Miller, *Blood*, 1990, 76, 271–278.
Moss et al., *Proc. Natl. Acad. Sci. USA*, 1991, 88, 8987–8990.
Muzyczka et al., *Curr. Topics in Micro. & Immunol.*, 1992, 158, 97–129.
Nixon et al., *Nature*, 1988, 336, 484–487.
Nixon et al., *Aids*, 1991, 5, 1049–1059.
Orkin et al., "Report and Recommendations of the Panel to Assess the NIH Investment in Research on Gene Therapy", NIH Recommendation Panel Assessment, 1995.
Piirsoo et al., *EMBO J.*, 1996, 15, 1–11.
Quantin et al., *Proc. Natl. Acad. Sci. USA*, 1992, 89, 2581–2584.
Rafalaski et al., *Biochem.*, 1990, 29, 7917–1922.
Rappaport et al., *Biochem.*, 1993, 32, 3291–3297.
Rappaport et al., *J. Biol. Chem.*, 1994, 263, 15124–15131.
Raz et al., *Proc. Natl. Acad. Sci. USA*, 1996, 93, 5141–5145.
Romani et al., *J. Exp. Med.*, 1994, 180, 83–93.
Rosenfeld et al., *Science*, 1991, 252, 431–434.
Rosenfeld et al., *Cell*, 1992, 68, 143–155.
Sallusto et al., *J. Exp. Med.*, 1994, 179, 1109–1118.
Samulski et al., *J. Virol.*, 1989, 63, 3822–3828.
Struhl et al., *Proc. Natl. Acad. Sci. USA*, 1979, 76, 1035–1039.
Togunaga et al., *Microbiol. Immunol.*, 1992, 36, 55–66.
Tokunaga et al., *J. Nat. Cancer Insti.*, 1984, 72, 955–962.
Townes et al., *EMBO J.*, 1985, 4, 1715–1723.
Tratschin et al., *J. Virol.*, 1984, 51, 611–619.
Tratschin et al., *Mol. Cell Biol.*, 1984, 4, 2072–2081.
Tratschin et al., *Mol. Cell Biol.*, 1985, 5, 3251–3260.
van Beusechem et al., *Proc. Natl. Acad. Sci. USA*, 1992, 89, 7640–7644.
Verma et al., "Gene therapy—promises, problems and prospects", *Nature*, 1997, 389, 239–242.
Wagner et al., *Adv. Drug Delivery Rev.*, 1994, 14, 113–135.
Wilson et al., *Proc. Natl. Acad. Sci. USA*, 1988, 85, 3014–3018.
Wilson et al., *J. Biol. Chem.*, 1992, 267, 963–967.
Wondisford et al., *Mol. Endocrinol.*, 1988, 2, 32–39.
Wu et al., *J. Biol. Chem.*, 1988, 263, 14621–14624.
Yates et al., *Proc. Natl. Acad. Sci. USA*, 1984, 81, 3806–3810.
Yates et al., *Nature*, 1985, 313, 812–815.
Yi et al., *J. Immunol.*, 1996, 156, 558–564.
Hermanson, G.T., *Bioconjgate Techniques*, Academic Press Ltd., London, 1996, 88–90.
Lalvani et al., "Rapid Effector Function in $CD8^+$ Memory T Cells", *J. Exp. Med.*, 1997, 186(6), 859–865.
Tuting, T. et al., "Genetically modified bone marrow–derived dendritic cells expressing tumor–associated viral or "self" antigens induce antitumor immunity in vivo", *Eur. J. Immunol.*, 1997, 27, 2702–2707.
Ausubel, F.M. et al. (eds.), *Current Protocols in Molecular Biology*, Greene Publishing Associates, 1989, Sections 9.10–9.14.
Fields, B.N. et al. (eds.), *Fundamental Virology*, Second Edition, Raven Press, New York, 1991.

* cited by examiner

In vivo vaccination against infectious agents by gene expression in professional Antigen Presenting Cells FIG. 3
MHC-LCR-regulated enzyme expression in transgenic mice macrophage
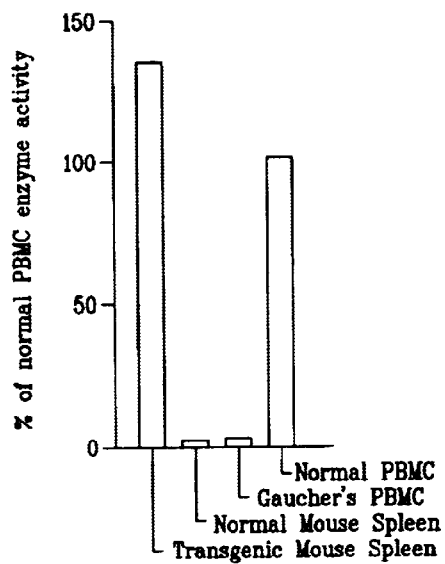
Human glucocerebrosidase transgenic mouse bone marrow macrophage.

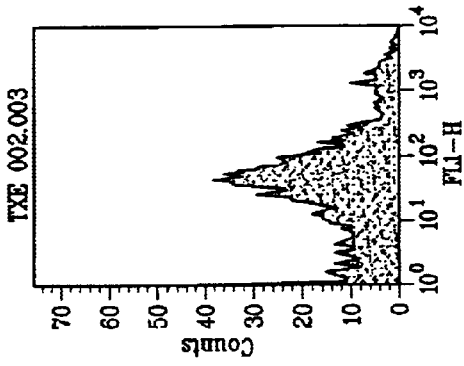
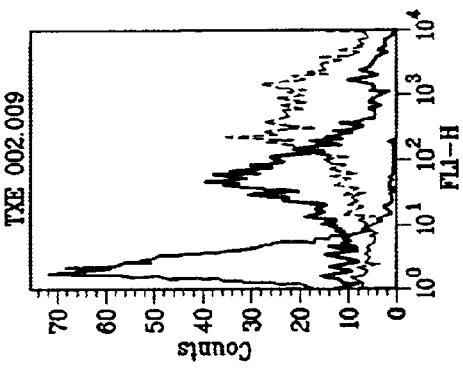
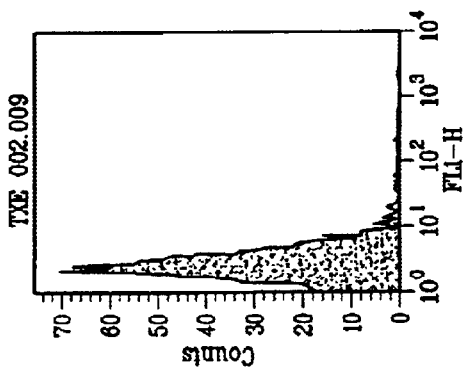
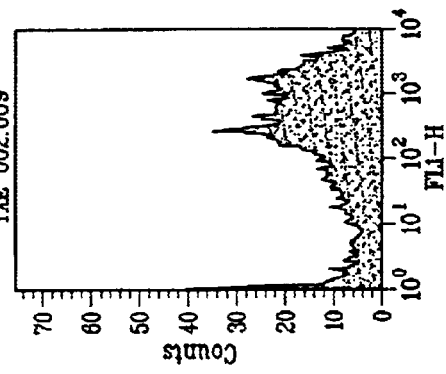

| | lum units | mg prot | lum/mg | Av (×10⁻⁶) | (St. Error) (×10⁻⁶) |
|---|---|---|---|---|---|
| naked DNA | 4623 | 0.877 | 5271.4 | 0.01 | 0.00 |
| | 4449 | 0.871 | 5107.9 | | |
| | 4526 | 0.84 | 5388.1 | | |
| K6CIII + DNA | 52408000 | 0.492 | 106520325.2 | 103.88 | 8.49 |
| | 45337400 | 0.515 | 88033788.4 | | |
| | 68721100 | 0.587 | 117071720.6 | | |

Luminescence

Effect of transfection time on transfection efficiency with 2 μg/μg CL22 complexes and 40 μM chloroquine Effect of transfection time on transfection efficiency with 20 μM chloroquine and 2 μg/μg CL22 complexes

METHODS FOR VACCINATION AND VACCINES THEREFOR

This application is a continuation-in-part of application Ser. No. 09/022,614, filed Feb. 12, 1998, now abandoned, which is a continuation of application Ser. No. 08/861,283 filed May 21, 1997, now abandoned, which is a continuation-in-part of application Ser. No. 08/800,079 filed Feb. 12, 1997, now abandoned, which claims priority from application Ser. No. 60/016,506 filed Apr. 30, 1996 and application Ser. No. 60/024,116 filed Aug. 16, 1996, all hereby incorporated by reference in their entireties.

FIELD OF THE INVENTION

The present invention relates to vaccines and methods of vaccination which involve transfection of cells.

BACKGROUND OF THE INVENTION

Vaccination has been an important medical pursuit ever since it was observed that, for certain diseases, initial exposure to the infectious agent conferred lifelong immunity against subsequent infections. Vaccines have been used for many years in order to build immunity in an individual against infection by particular pathogenic organisms such as viruses, bacteria, fungi and parasites.

Early vaccines relied on live organisms or killed organisms that retained their immunogenicity. A better understanding of the structure and function of particular pathogens and of the mechanisms of adaptive immunity has made it possible to design safer and more directed vaccines. The current vaccine against Hepatitis B virus, for example, relies on inoculation using only a portion of the viral surface antigen, rather than the complete organism. Such directed vaccines lead to fewer side-effects and avoid unwanted immune responses to antigens that are not protective, i.e., do not confer lasting immunity.

Advanced vaccine design has made use of recombinant DNA technology and gene therapy concepts to provide DNA vaccines, wherein a vector for expression of a desired immunogen in mammalian cells is injected into a subject. The vector is taken up into cells around the site of injection, and then operates to express the immunogen in situ, which in turn leads to a protective immune response.

A problem associated with the use of DNA vaccines thus far is that the tissue into which the vector is typically injected, i.e., muscle, is not usually associated with antigen presentation. Consequently, the DNA vaccine does not produce a highly effective immune response.

There is a need for methods and specialized gene delivery vehicles suitable for delivery of complex antigens to cells so that the resulting antigen presentation is capable of activating substantially all of the components of the adaptive immune system, i.e., capable of eliciting the immune response necessary to combat a particular pathogen whether mediated by antibodies, cytotoxic T cells, helper T cells, natural killer cells, or macrophages.

SUMMARY OF THE INVENTION

The present invention provides methods and compositions for obtaining long-lasting immunity via delivery to an antigen presenting cell a complex comprising a nucleic acid encoding a first epitope, and a peptide containing a second epitope.

Antigen presenting cells present antigenic epitopes of antigens to T cells in association with either Class I or Class II MHC molecules. Endogenously synthesized proteins are generally presented in association with Class I whereas proteins taken up from the environment (exogenously synthesized proteins) are generally presented in association with Class II. It is therefore beneficial for a vaccine to produce presentation of the required antigen to both Class I and II MHC molecules. The invention provides for stimulation of both class I and II presentation by providing antigen to an antigen presenting cell in the form of an endogenously synthesized protein (i.e., a nucleic acid-encoded epitope) and an exogenously synthesized protein.

It is believed that the dual delivery to an antigen presenting cell of an epitope, or antigen, in its peptide or polypeptide form, together with a second nucleic acid encoded epitope results in an enhanced immune response.

The invention therefore encompasses a method of vaccinating a mammal against a disease, comprising administering to said mammal a mixture of (i) a nucleic acid encoding a first epitope and (ii) a peptide comprising a second epitope such that the nucleic acid and the peptide are taken up by and the nucleic acid is expressed in a professional antigen presenting cell of the mammal, wherein an immune response is elicited in the mammal to the epitopes.

The invention also encompasses a method of vaccinating a mammal against a disease wherein the mixture administered comprises a complex comprising (i) a nucleic acid encoding a first epitope and (ii) a peptide comprising a second epitope such that the complex is taken up by and expressed in a professional antigen presenting cell of the mammal, wherein an immune response is elicited in the mammal to the first and second epitopes.

The invention also encompasses a method of vaccinating a mammal against a disease, comprising administering, to the mammal professional antigen presenting cells containing (i) a recombinant nucleic acid encoding a first epitope and (ii) a second epitope that is not normally present in the antigen presenting cells and, wherein upon administration an immune response is elicited in the mammal to the epitopes.

The invention also encompasses a composition for vaccinating a mammal against a disease, comprising a complex comprising (i) a vector comprising a nucleic acid encoding a first epitope and a sequence which permits maintenance of the vector in episomal form , and (ii) a peptide containing a second epitope, wherein said composition is adapted for delivery to or selective expression in antigen presenting cells.

The invention also encompasses a complex for vaccinating a mammal against a disease, comprising professional antigen presenting cells containing (i) a recombinant nucleic acid encoding a first epitope and (ii) a peptide containing a second epitope that is not normally present in the antigen presenting cells.

The invention encompasses a method of vaccinating a mammal against a disease, comprising administering to the mammal a complex comprising (i) a nucleic acid and (ii) a peptide including an epitope such that the complex is taken up by a professional antigen presenting cell of the mammal, wherein an immune response is elicited in the mammal to the epitope.

In this aspect of the invention, it is believed that the presence of the nucleic acid in the mixture promotes uptake by antigen presenting cells of the peptide containing an epitope so as to promote an immune response to the epitope.

Preferably, the first epitope is from an infectious agent or an organism, and the first epitope is present in the mammal during the course of a disease.

It is preferred that the complex further comprises a second epitope, and that the first and second epitopes are epitopes of the same antigen, or epitopes of the same infectious agent or organism.

For example, the first and/or second epitope may comprise an immunodominant epitope of influenza NP.

It is also preferred that the complex or mixture further comprises a second peptide that contains an epitope that is different from the epitope contained in the peptide referred to in (ii) above.

The complex may further comprise a cell-targeting ligand for targeting professional antigen presenting cells.

It is preferred that the nucleic acid is intimately associated with the peptide containing the epitope such that the nucleic acid is preferably in condensed form.

Therefore, it also is preferred that the first epitope is present in a two-domain polypeptide comprising the first epitope fused to a nucleic acid-binding amino acid sequence. As used herein, the term "epitope" refers to an immunogenic amino acid sequence. An epitope may refer to a minimum amino acid sequence of 6–8 amino acids (i. e., a peptide), which minimum sequence is immunogenic when removed from its natural context and is carried in a complex according to the invention as a peptide, or when transplanted into a heterologous polypeptide such that it retains its natural immunogenicity and thus is carried in a complex according to the invention as part of a polypeptide. An epitope also may refer to that portion of a natural polypeptide which is immunogenic, where the natural polypeptide containing the epitope is referred to as an antigen. Of course, a polypeptide or antigen may contain one or more distinct epitopes. An epitope also may refer to an immunogenic portion of a multichain polypeptide, i.e., which is encoded by distinct open reading frames. The terms epitope, peptide, and polypeptide all refer to a series of amino acids connected one to the other by peptide bonds between the alpha-amino and alpha-carboxy groups of adjacent amino acids, and may contain or be free of modifications such as glycosylation, side chain oxidation, or phosphorylation, provided such modifications, or lack thereof, do not destroy immunogenicity. As used herein, the term "peptide" is meant to refer to both a peptide and a polypeptide or protein.

It is desirable that the epitope (peptide, polypeptide, antigen) be as small as possible while still maintaining immunogenicity. Immunogenicity is indicated by the ability to elicit an immune response, as described herein, for example, by the ability to bind an appropriate MHC molecule (i.e., an MHC class I or class II molecule) and to induce a T cell response and an antibody response, e.g., by measuring a cytotoxic T cell response or a serum antibody response to a given epitope(s).

As used herein, the terms "antigen" or "immunogen" refer to a peptide, protein, polypeptide which is immunogenic, that is capable of eliciting an immune response in a mammal, and therefore contains at least one and may contain multiple epitopes. According to the invention a "pathogen", organism, or "agent" may cause a disease for which vaccination is desired according to the invention. As used herein, these terms refer to a virus, bacteria, fungus, or a parasite. The term "agent" also may refer to antigens such as tumor antigens or antigens associated with autoimmunity. The invention does not contemplate administration of a whole pathogen, or its entire genome, to achieve antigenicity. Therefore, the term "epitope" is limited to this extent that it does not refer to a whole pathogen.

"Immune response" refers to either a cellular or a humoral immune response or to both a cellular and a humoral immune response.

It is believed that the antigenic peptide or protein delivered to the target cell by the delivery vehicle will be processed as an exogenously synthesized antigen and epitopes will be presented predominantly in association with Class II MHC molecules to Class II-restricted T cells. The antigen encoded by the nucleic acid of the delivery vehicle will be endogenously synthesized and epitopes of the antigen will be presented predominantly in association with Class I MHC molecules. Presentation in association with both MHC Class I and II molecules will ensure a strong immune response.

It is preferred according to the invention that the nucleic acid encoded antigen is expressed only in professional antigen-presenting cells (APC).

As used herein, the term "professional antigen-presenting cells" refers to MHC class II-bearing cells (that is, cells which express MHC class II or can be induced to express class II); such cells include B-lymphoctyes, dendritic cells other than follicular dendritic cells, macrophages, endothelial cells, phagocytic leukocytes, monocytes or monocyte derived cells, Kupffer cells, Langerhans cells, or stem cells thereof or other precursor cells, and other cells which either express class II or can be induced to express MHC class II.

The restricted expression of the gene to APCs or related cells can be achieved in two ways: 1) by targeting the delivery vehicle only to APCs or related cells and/or 2) by restricting the expression of the gene encoding the antigen to APCs or related cells.

It is contemplated according to the invention that the complex may further include a targeting ligand for targeting a receptor on the cell surface. Targeted delivery may be accomplished nonspecifically to both non-APCs and APCs, for example, where expression of the gene is restricted to APCs, or specifically to APCs only.

Thus, it is preferred that the complex of the present invention is adapted to target specifically to a professional antigen presenting cell of a mammal and/or the nucleic acid is adapted to be expressed specifically in a professional antigen presenting cell.

The term "to target specifically to a professional antigen presenting cell" refers to the situation where the complex is targeted to APCs and thus delivery will be substantially restricted to APCs. However, one skilled in the art will realize that targeting is rarely completely efficient and some delivery will occur to non-targeted cells. The term refers to where delivery to APCs is increased relative to other cell types, preferably by approximately two-fold or more.

Targeted delivery to APCs, their stem cells or other precursor cell types can be achieved by receptor-mediated gene transfer using delivery vehicles comprising the following examples of targeting ligands: (a) for hemopoietic stem cells: anti-CD34 monoclonal antibody, or the Stem cell factor (c-Kit or CD117), or flk-2 ligand (human homolog STK-1); (b) for monocyte/macrophage/dendritic cell precursors: anti-CD33 monoclonal antibody; (c) for differentiated macrophage/dendritic cells: glycosylated DNA binding peptides carrying mannose groups may be used to target to specific receptors, for example the mannose receptor; and (d) for MHC class II bearing cells: an antibody that is specific for the constant region of MHC class II proteins or a ligand that binds MHC class II, for example soluble CD4; for example, one subset of MHC class bearing cells, B lymphocytes, may be targeted using soluble CD4 or using antibodies to or ligands for CD80, CD19, or CD22; for endothelial cells, γ-interferon and the vascular endothelial growth factor (VEGF) receptors; and (e) for APCs or T cells ligands for or antibodies to co-stimulatory molecules such as B7-1, B7-2 or CD28, CTLA-4, respectively. These targeting ligands may play a dual role which involves increasing co-stimulatory signals to the APC; and thus increasing its activation, in addition to their targeting function.

Alternatively or in addition to the use of targeted complexes, DNA regulatory elements which lead to expression in APCs, their stem cells or other precursor cell types can be utilized.

The term "to be expressed specifically in a professional antigen presenting cell" refers to the situation where the expression of the nucleic acid is substantially restricted to APCs. The term therefore covers the situation where expression of the nucleic acid is restricted predominantly to APCs, for example, where approximately 50% and preferably 80%–100% of the cells in which expression of the nucleic acid occurs are APCs.

It is further contemplated according to the invention that the nucleic acid encoded antigen is predominantly expressed only in professional antigen-presenting cells (APCs).

Preferred regulatory elements include locus control regions (LCRs) such as the MHC class II LCR.

The present invention may be used to cause presentation of any protein or peptide capable of eliciting an immune response.

The present invention is applicable to any infectious agent against which an immune response can be measured. The invention also is applicable to other disease targets against which an immune response would be beneficial, such as tumors. Thus, the invention contemplates the use of a sequence encoding epitope of any infectious agent or disease target.

Preferably, the epitope is a key epitope, i.e., either the complete polypeptide sequence or an epitope which gives rise to a strong immune response to a particular infectious agent or disease. Examples of preferred epitopes include peptide epitopes of the influenza nucleoprotein (NP) gene, the tat, rev, gag and nef components of HIV, and epitopes from the E6 and E7 proteins of HPV. Additional preferred epitopes are those which are found to induce tolerance, such as the collagen involved in Rheumatoid arthritis.

More than one epitope may be encoded by the gene in order to increase the likelihood of an immune response. This is particularly important where the key epitopes which give rise to a protective immune responses have not been identified. Thus, in a further aspect of the present invention, the nucleic acid encodes more than one epitope capable of eliciting an immune response to a particular infectious agent or disease. This is particularly important where the key epitope(s) which give rise to a protective immune response have not been identified. Preferably, the epitope is present in a polypeptide (i.e., a polypeptide antigen) and therefore the polypeptide is encoded in a construct. Preferably, the construct is a multi-gene construct in which the antigens are coordinately expressed.

In a further embodiment of the present invention, where an immune response is desired to an infectious agent, all of the open reading frames from the pathogen's genome are arranged together in a construct in order to form the coding region of the delivery vehicle. This has the advantage that all the antigens will be present and thus the likelihood of an immune response increased.

Basically, an expression-library is made of the pathogen DNA and the expression-library delivered in the delivery vehicle to the cell in order to elicit an immune response.

In a further embodiment of the present invention, DNA sequences encoding antigens specific for different diseases or infectious agents may be arranged together in a construct for expression in the delivery vehicle of the present invention. The antigens may be whole proteins or multiple or single epitopes thereof arranged as a single gene or as a multi-gene construct. The delivery means will therefore provide immune protection against a number of diseases specified by the antigens encoded within the DNA construct.

In a further embodiment of the present invention the delivery vehicle may comprise mixture of antigenic peptide/protein components. These may be derived from the same antigen, they may be different antigens from the same infectious agent or disease, or they may be from different infectious agents or diseases. The complex or mixture will therefore raise an immune response against a number of antigens and possibly a number of infectious agents or diseases as specified by the antigenic peptide/protein components of the delivery system.

In a further embodiment of the present invention the antigenic components of the complex or mixture may, or may not, be glycosylated depending on the requirement for glycosylation for the generation of a suitable immune response against the epitope or antigen.

In a further embodiment of the present invention, the DNA encoded antigen or the antigenic component of the complex or mixture may not necessarily encode the most immunodominant epitopes of the antigen. They may be epitopes which are more highly conserved between different strains of an infectious agent or disease, or may be epitopes which have limited, or no, mutational variation. Antigens may also be encoded as a series of subgenes which cover the whole antigen but the whole antigen may not necessarily be encoded in a single gene.

In a further embodiment of the present invention the DNA may encode additional factors which will have the effect of upregulating the immune response to the encoded antigen, or protein/peptide component of the delivery system. The additional factors may include cytokines for the general upregulation of specific components of the immune response e.g. interferon gamma, IL-2, IL-4, IL-10, IL-12, and GM-CSF; lymphokines; or co-stimulatory molecules such as B7-1, B7-2, ICAM-1 and ICAM-3. Alternatively, each factor may be included in a mixture of complex according to the invention in its polypeptide form, in that it may be co-administered with a nucleic acid and antigen according to the invention or it may be conjugated to the antigen or to a nucleic acid binding peptide so as to form part of the delivery complex.

The invention encompasses the delivery of a vector or nucleic acid to a cell (i.e., the use of a delivery vehicle).

As used herein, the phrase "means for delivering" a vector to a cell" or "adapted for delivery" to a cell refers to any means, including viral and non-viral delivery means, by which it is possible to deliver nucleic acid and an antigenic peptide or protein associated with nucleic acid to a mammalian cell, including DNA/polycation complexes, self assembling virus like particles, viral vectors which are capable of delivering nucleic acid to a mammalian cell such as adenoviruses, retroviruses and adeno-associated viruses, microspheres which are used for delivery of DNA or protein to cells, e.g., polylactide glycolide polymers, and liposomes. Delivery means useful according to the present invention are well known to those skilled in the art and are described further herein.

Particularly preferred delivery vehicles are those which include polycation-condensed nucleic acid which in addition may be coupled with a ligand for targeting cells specifically or non-specifically.

The delivery vehicle may therefore include a nucleic acid condensing peptide, e.g., a polycationic heteropeptide, which binds DNA (i.e., a DNA binding peptide).

In another embodiment of the invention, the complex or mixture may include a peptide which does not necessarily participate in delivery of the vector or nucleic acid to the cell, but which is antigenic and thus serves to induce an immune response in a mammal upon entry of the delivery vehicle into the cell. The antigenic peptide may be a portion of a two-domain peptide comprising a DNA-binding amino acid sequence and the antigenic peptide. The two domains may be fused via a peptide bond to form a fusion polypeptide, wherein the antigenic domain is amino terminal and the DNA binding domain is carboxy terminal, or wherein the DNA binding domain is amino terminal and the DNA binding domain is carboxy terminal. Where a protein contains a DNA binding domain and also an epitope(s) to which an immune response is desired, the protein may be considered to be essentially equivalent to a two domain peptide as described herein.

Alternatively, the two domains may be separated by a cleavable linker such as a acid labile linkage or a peptide sequence cleavable by an endosomal protease such as cathepsin.

In another embodiment, it is also contemplated that the epitope is not part of a fusion protein but is directly absorbed onto a complex comprising a nucleic acid encoding an epitope in association with a DNA binding domain by electrostatic, hydrophobic, covalent or other interactions.

Where a DNA binding peptide is used in a complex or mixture of the invention, whether it be as part of a two domain fusion polypeptide or noncovalently associated with an epitope, it is envisioned that the DNA binding peptide binds the nucleic acid of the complex or mixture in a condensing reaction and therefore permits intimate association of the epitope portion of the complex or mixture with the nucleic acid.

In a further embodiment of the present invention the antigen encoding nucleic acid sequence may contain a signal sequence for secretion of the antigen outside the cell. Signal sequences useful in the present invention are well known to those skilled in the art and are, for example, described in Blobel and Dobberstein (1975), J. Cell Biol., 62, 852–862. The secreted antigen will be taken up by the secreting cell and other neighbouring cells, processed as an exogenous antigen, and presented in association with Class II MHC. The delivery vehicle of the present invention may contain a mixture of nucleic acids encoding an antigen, some with, and some without, the secretion signal sequence. Thus secreted and non-secreted antigen can be produced in the same cell and both Class I and Class II MHC presentation can be produced after a single transfection event.

An antigenic peptide useful as an antigen component of a delivery vehicle or in a two-domain peptide may be from the same or a different organism against which a DNA-based immune response is desired. An example of a preferred antigenic peptide for this purpose is the immunodominant peptide epitope(s) of influenza nucleoprotein (NP).

Upon entry of this delivery vehicle into a cell, an immune response will be elicited to the antigenic peptide. The immune response will be subsequently sustained and expanded by the expression of the antigenic protein encoding sequences also present in the delivery vehicle.

It is further preferred that the vector containing a nucleic acid encoding an antigen is maintained at a high copy number in dividing and non-dividing cells of a patient.

Thus, particularly preferred vectors useful according to the invention contain a sequence which permits maintenance of the vector in an episomal form. Such vectors may comprise a minimal origin of replication of a papilloma virus, a minichromosomal maintenance element of a papilloma virus, and a cloning site for inserting a nucleic acid encoding one or more antigens. This may be achieved by employing the BPV-I vector system comprising a plasmid harboring the BPV-I origin of replication, or a minimal origin plus minichromosomal maintenance element, as disclosed hereinbelow, and optionally the BPV—L E1 and E2 genes.

If desired, the antigenicity of selected proteins (e.g., targeting ligands) or peptides of the delivery vehicle, or other proteins encoded by the vector, (e.g., the BPV-1 E1 and E2 proteins) may be eliminated by introducing into their open reading frames sequences from the Epstein bar virus EBNA-1 protein encoding a Gly-Ala repeat, that suppresses antigen presentation of amino acid sequence linked in cis.

A composition of the present invention may be used in ex vivo gene therapy or in in vivo gene therapy in order to provide immune protection against various infectious agents and diseases.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The present invention is illustrated in the appended examples, with reference to the following figures:

FIG. 3 demonstrates cell-specific expression of the human glucocerebrosidase gene under the control of the MHC class II LCR in APCs.

FIGS. 5(A–D) represent FACScan analysis of COS cells incubated with either buffer (A), peptide alone (B), or complex (C). D represents an overlay plot (thin line buffer; solid-broad line, peptide, lined line, complex).

DETAILED DESCRIPTION

Figure 1:
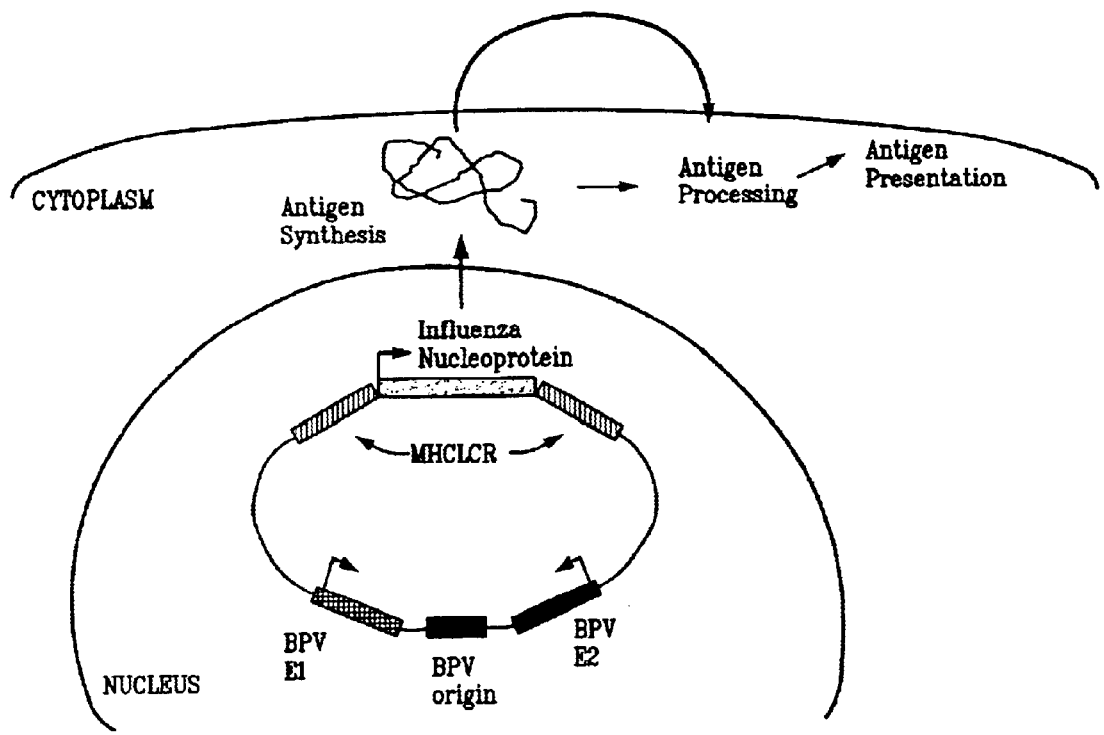
FIG. 1 is a schematic diagram showing sustained, targeted expression of antigenic proteins in professional antigen presenting cells (dendritic cells).
Figure 2:
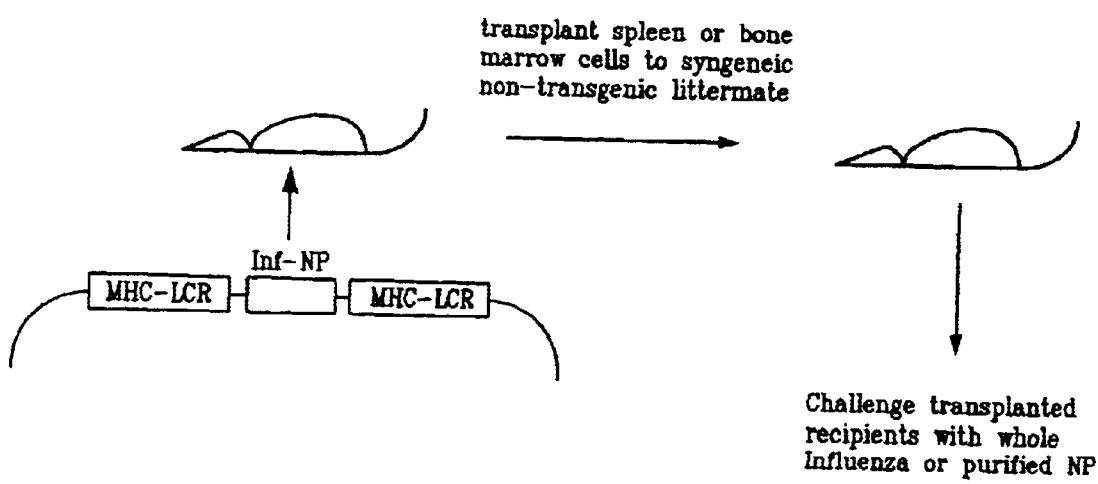
FIG. 2 is a schematic diagram showing in vivo vaccination against infectious agents where gene expression in professional antigen presented cells.
Figure 4:
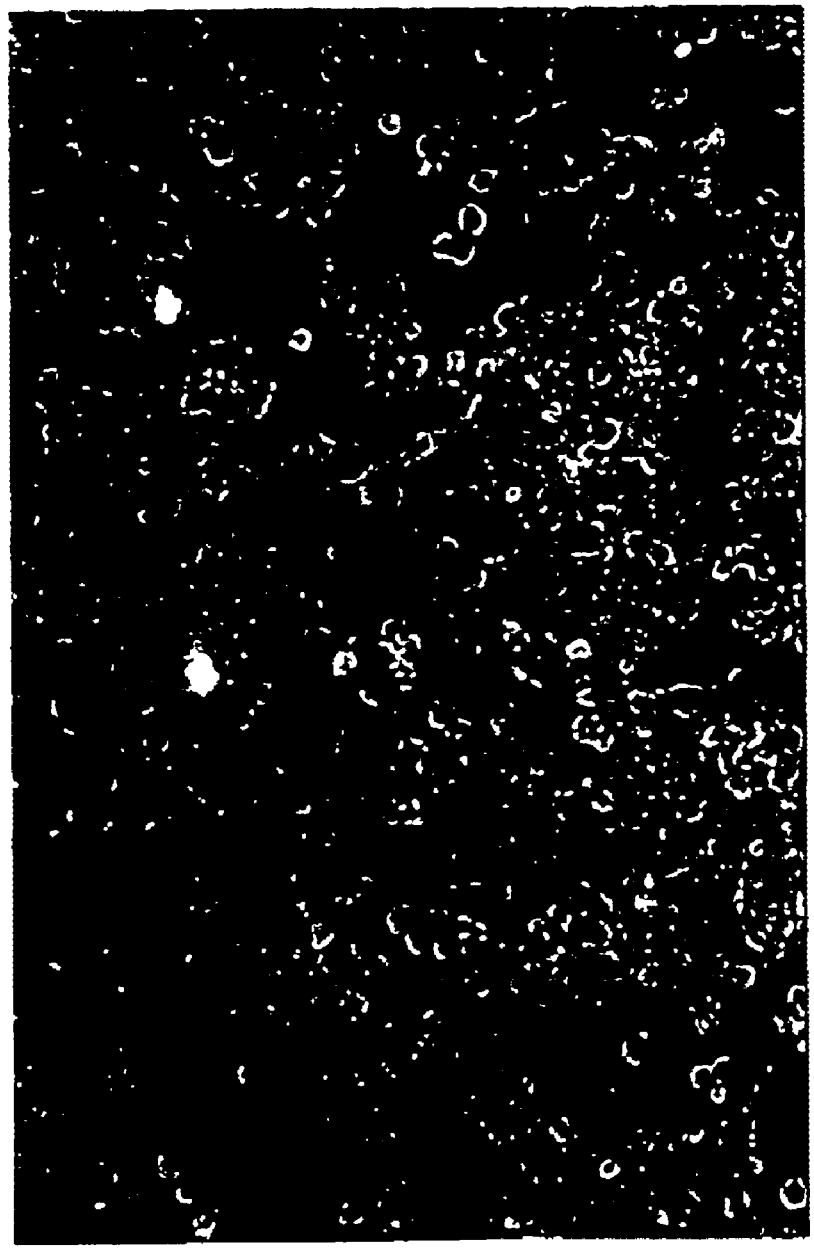
FIG. 4 is a microscopic view of an in vitro matured dendritic cells transfected with pEGFP-NI. Transfected cells are fluorescent.

The invention is based on the observation that an immune response to an antigen may be rendered highly specific and effective by delivery to antigen presenting cells of a mixture comprising an antigen in its peptide or polypeptide form and a nucleic acid encoding an antigen.

The invention also is based on the observation that an immune response to an antigen may be rendered highly effective by delivery to antigen presenting cells of a complex comprising an antigen in its peptide or polypeptide form and a nucleic acid encoding an antigen.

The invention also is based on the observation that an immune response to an antigen may be rendered highly effective by delivery to antigen presenting cells of a complex comprising an antigen in its peptide or polypeptide form and a nucleic acid. In this aspect of the invention, the nucleic acid need not encode an antigen, but is useful to promote uptake of the antigen by the antigen presenting cell.

In the simplest form, the peptide antigen and the nucleic acid encoded antigen described herein are the same. However, it is believed that a more effective immune response may be obtained using a first peptide antigen in combination with a second different nucleic acid-encoded antigen, or wherein several different peptide antigens are administered in combination with one or several different nucleic acid-encoded antigens. A "more effective" immune response will be evident, as it relates to prior art vaccination procedures and compositions, as a two-fold and preferably a five-fold to ten-fold higher immune response, or by the finding that both a cellular and a humoral immune response is elicited by complexes or mixtures of the invention. Methods and compositions for making and carrying out the invention are described in detail below.

VACCINATION VIA ANTIGEN PRESENTING CELL-RESTRICTED GENE

Expression According to the Invention

The invention provides for vaccination against a disease or pathogen via administration to a mammal of a mixture or complex described according to the invention and, in some cases, of antigen presenting cell—(i.e., tissue—) restricted expression of a nucleic acid encoding an antigen associated with the disease or pathogen. Tissue-restricted expression of a gene encoding an antigen for which an immune response is desired, wherein the tissue to which expression is restricted comprises antigen presenting cells, as defined herein or subsets thereof is obtained as follows.

Two modes of effective antigen presenting cell-restricted gene expression are contemplated according to the invention: 1) via targeted delivery of a mixture or complex comprising an antigenic peptide and a gene (preferably encoding an antigen for which an immune response is desired) to antigen presenting cells, and 2) via either targeted or untargeted gene delivery (and thus possible delivery of the gene to different cell types) wherein control of expression of the gene is effected using genetic control elements which limit gene expression to the desired antigen presenting cells or subset of cells.

Delivery of Nucleic Acid to Host Cell

It is contemplated according to the invention that a mixture or complex according to the invention may be delivered to an antigen presenting host cell non-specifically or specifically (i.e., to a designated subset of host cells). Three modes of delivery are contemplated. First, wherein no targeting ligand is used. Second and third, where a targeting ligand is employed; in the case of non-specific delivery to cells, a non-specific ligand is used that targets a cell surface receptor that is present on the target cell population as well as on other cells; in the case of specific delivery, a ligand is used that targets a specific subset of cells. Therefore, the complex or mixture may be delivered generally to any cell, or may be delivered to antigen presenting cells, or may be delivered to a subset of antigen presenting cells, these subsets and targeting ligands and cognate receptors being described herein.

1. Non-viral Delivery to APCs

Non-viral delivery to APCs may or may not employ a targeting ligand. Targeted delivery to APCs, their stem cells, or other precursor cell types can be achieved by receptor-mediated gene transfer using a complex containing a ligand which is targeted to a cognate receptor on a cell surface. Targeting ligands useful according to the invention include but are not limited to the following: (a) for hemopoietic stem cells: anti-CD34 monoclonal antibody, or the Stem cell factor (c-Kit or CD117), or flk-2 ligand (human homolog STK-1); (b) for monocyte/macrophage/dendritic cell precursors: anti-CD33 monoclonal antibody; (c) for differentiated macrophage/dendritic cells: glycosylated DNA binding peptides carrying mannose groups may be used to target to specific receptors, for example the mannose receptor; and (d) for MHC class II bearing cells: an antibody that is specific for the constant region of MHC class II proteins or a ligand that binds MHC class II, for example soluble CD4; for example, one subset of MHC class II-bearing cells, B lymphocytes, may be targeted using soluble CD4 or using antibodies to or ligands for CD80, CD19, or CD22; for endothelial cells, y-interferon; and (e) for APCs or T cells, co-stimulatory molecules such as B7-1, B7-2 or CD28, CTLA-4, respectively.

Targeted delivery vehicles for delivery of DNA constructs to cells are known in the art and include DNA/polycation complexes which are specific for a cell surface receptor, as described in, for example, Wu and Wu (1988) J. Biol. Chem 263:14621; Wilson et al. (1992) T. Biol. Chem. 267:963–967, and U.S. Pat. No. 5,166,320, and, for example, U.S. Ser. No. 60/011,531, assigned to the same assignee and hereby incorporated by reference. In this co-pending application, a self-assembling virus-like particle is described and includes the DNA of interest and condensing peptides which are heteropeptides with respect to their amino acid composition (i.e., containing at, least two different amino acids which are preferably basic and thus good DNA binding and DNA condensing peptides) and which have low polydispersion (i.e., a given preparation of a heteropeptide which has low polydispersion contains peptides of very similar, if not identical lengths, such that the preparation is essentially monodispersed).

The invention thus also relates to a nucleic acid construct which is delivered to a cell using a synthetic virus like particle for transfecting nucleic acid into a mammalian cell. The synthetic virus like particle includes a recombinant nucleic acid, a plurality of nucleic acid condensing peptides, the peptides being non-covalently associated with the recombinant nucleic acid such that the nucleic acid is in condensed form, wherein each nucleic acid condensing peptide is a heteropeptide, and plurality of nucleic acid condensing peptides has low polydispersion.

The plural nucleic acid condensing peptides may include a first nucleic acid condensing peptide and a second nucleic acid condensing peptide, wherein the first nucleic acid condensing peptide comprises a first functional group covalently bound thereto. The first nucleic acid condensing peptide may further include a second functional group which may be directly bound to the peptide or may be covalently bound to the first functional group, where the first functional group is bound to the peptide.

Alternatively, a second nucleic acid condensing peptide also may include a second functional group covalently bound thereto, the second functional group being different from the first functional group. The first and second nucleic acid condensing peptides may have identical or different amino acid sequences.

The functional groups which are bound to peptides useful according to the invention include antigenic peptides or proteins, such as influenza nucleoprotein (NP), or a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The first nucleic acid condensing peptide may include 8–24 positively charged amino acid side groups; for example, the number of positively charged amino acid side groups may be in the range of 12–18.

The ratio of positive/negative charges in a synthetic virus like particle that is capable of targeting a specific mammalian cell type is within the range 0.5–3 per phosphate residue in the nucleic acid; this ratio thus also may be within the range 0.8–1.2.

The ratio of positive/negative charges in a synthetic virus like particle that is unrestricted with respect to the type of cell it targets is in within the range of 0.5–5 per phosphate residue in the nucleic acid, and thus also may be within the range of 1.2–2.

A nucleic acid condensing peptide which is particularly useful for condensing the nucleic acid construct and therefore for delivering nucleic acid to a cell includes a peptide of the generic formula

NH2—A—(X$_1$X$_2$Y$_1$Y$_2$)$_n$X$_3$X$_4$—(Z$_1$Z$_2$Z$_3$Z$_4$)—(X$_5$X$_6$Y$_3$Y$_4$)$_m$X$_7$X$_8$BCOOH wherein each of $X_{1-8}$ is, independently, an amino acid having a positively charged group on the side chain; wherein each of $Y_{1-4}$ is, independently, a naturally occurring amino acid which promotes alpha helix formation; wherein each of $Z_{1-4}$ is, independently, a naturally occurring amino acid with at least 3 amino acids having a high propensity to form a stabilized turn structure; wherein A is an amino-terminal serine or threonine residue; wherein B is any amino acid and wherein n=2–4 and m=2.

Other peptides are those wherein each of X, $_8$ is, independently, lysine, arginine, 2,4-diamino-butyric acid or ornithine; wherein each of $Y_{1-4}$ is, independently, glutamic acid, alanine, leucine, methionine, glutamine, tryptophan or histidine; wherein each of $Z_{1-4}$ is, independently, asparagine, glycine, proline, serine, or aspartic acid; wherein B is any one of alanine, glutamic acid or cysteine.

It is also contemplated according to the invention that peptides useful in this embodiment of the invention which involves delivery of a complex according to the invention to a cell either ex vivo or in vivo may contain one or more internal Serine, Threonine, or Cysteine residues, preferably at a position in the sequence which will be exposed for conjugation to a selected ligand, and thus not on the positively charged (nucleic acid oriented) face of the a-helix. This positioning of selected reactive amino acid residues within the peptide are oriented such that they do not contact the face of the peptide that contacts nucleic acid permits conjugation of the peptide with other functional peptides by bonds of selected and defined stability. Cysteine allows specific conjugation via the thiol side chain to compounds containing other reactive thiol groups (via disulfide), alkylating functions (to form thioether bonds), or other thiol reactive groups such as maleimide derivatives.

Peptides which fall within this generic sequence include:
NBC7
TRRAWRRAKRRAARRCGVSARRAARRAWRRE-OH; (SEQ ID NO:1) and, NBC11 H-TKKAWKKAEKKAAKKCGVSAKKAAKKAWKKA-NH$_2$. (SEQ ID NO:2) Thus, a nucleic acid condensing peptide useful for delivery of a nucleic acid may contain: 1) helix-forming amino acids, 2) a repeating three-dimensional structure that contacts the major groove of the nucleic acid, 3) suitable chromophores for quantitation, and 4) a number of "handles" (i.e., reactive sites) for regio-specific conjugation of ligands which form accessory functional domains.

Nucleic acid condensing peptides also may include portions of HI (sequence I, II or III below) which are identified herein as sequences which possess the ability to condense nucleic acid. Therefore, a nucleic acid condensing peptide can include a linear combination of the following three consensus sequences where the total sequence length is>17 residues:

Sequence I: -K-K-X-P-K-K-Y-Z-B-P-A-J (SEQ ID NO:3) where: K is Lysine, P is Proline; A is Alanine; X is Serine, Threonine or Proline; Y is Alanine or Valine; Z is Alanine, Threonine or Proline; B is Lysine, Alanine, Threonine or Valine; and J is Alanine or Valine.

Sequence II—-X-K-S-P-A-K-A-K-A- (SEQ ID NO:4) where: X is Alanine or Valine; K is Lysine; S is Serine; P is Proline; and A is Alanine.

Sequence III: -X-Y-V-K-P-K-A-A-K-Z-K-B (SEQ ID NO:5) where: X is tysine or Arginine; Y is Alanine or Threonine; Z is Proline, Alanine or Serine; B is Lysine, Threonine or Valine; K is Lysine; P is Proline; A is Alanine.

One such peptide is NBC1, which has the following structure:
NH2-[SV40 NLS]-[Seq I]-[Seq II]-[Seq III]-[SV40 NLS]-[Seq I]-C—COOH, where —C— is Cysteine; where the SV40 NLS has the sequence Pro-Lys-Lys-Lys-Arg-Lys-Val-Gln (SEQ ID NO:6); and the sequence
H-PKKKRKVEKKSPKKAKKPAAKSPAKAKA KAVKPKAAKPKKPKKKRKVEKKSP KKAKKPAAC (Acm)-OH. (SEQ ID NO:7)

Another such nucleic acid condensing peptide of the invention will have a peptide that falls within the following generic sequence: NH2-X-(Y)$_n$—C—COOH, where X is either absent or Serine or Threonine; Y is sequence I, II or III as defined above; n is 2–6; and C is Cysteine.

Other such peptides have the following structures and sequences:
NBC2 has the structure: NH$_2$-[Seq III][SV40 NLS1]-[Seq I]-C—COOH, where —C— is Cysteine.

NBC8 has the structure: NH$_2$-[Seq I]-[Seq I]-C—COOH, where —C— is Cysteine.

NBC9 has the structure: NH$_2$-[Seq I]-[Seq I]-[Seq I]-C—COOH, where —C— is Cysteine.

NBC10 has the structure: NH$_2$-[Seq I]-[Seq I]-[Seq I]-[Seq I]-C—COOH
where —C— is Cysteine; the amino acid sequences of which are as follows:
NBC2
H-KAVKPKAAKPKKPKKKRKVEKKSPKKAK KPAAC(Acm)-OH (SEQ ID NO:8);
(NBC8 H-KKSPKKAKKPAAKKSPKKAKKPAAC (Acm)-OH (SEQ ID NO:9);
NBC9
H-KKSPKKAKKPAAKKSPKKAKKPAAKKSP KKAKKPAAC(Acm)-OH (SEQ ID NO:10);
NBC10
-KKSPKKAKKPAAKKSPKKAKKPAAKKSPK KAKKPAAKKSPKKAKKP (Acm)-OH (SEQ ID NO:11);

As described above, nucleic acid condensing peptides having a low polydispersion index (PDI) are useful for delivery to a cell of a nucleic acid encoding an antigen according to the invention. The PDI for such peptides may be calculated from analysis of the peptides by electro-spray mass spectrometry. This method gives the exact mass of each component to within 0.001%. The PDI values of the peptide preparations useful in the present invention are in the range of 1.0–1.100. Peptide preparations which are especially useful in the invention possess a PDI<1.01, and even <1.001.

Preferred delivery vehicles are prepared as follows. A synthetic virus like particle is formulated such that the nucleic acid encoding an antigen and the peptide preparation are prepared in equal volumes of the same buffer. The nucleic acid is shaken or vortexed while the condensing peptide preparation is added at the rate of 0.1 volume per minute. The complex is left at room temperature for at least 30 minutes prior to addition to the target cells or prior to administration to a subject, and can be stored at 4° C. The particle is centrifuged to remove any aggregated material.

In addition to the above-described DNA/polycation complexes for cell targeting, methods are known in the prior art for preparing cell-targeting liposomes containing nucleic acid. An example of targeting liposomes is immunoliposomes, which are prepared, for example, by adsorption of proteins (e.g., immunoglobulin) on the liposomal surface; incorporation of native protein into the liposome membrane during its formation (e.g., by ultrasonication, detergent dialysis or reverse phase evaporation); covalent binding (direct or via a spacer group) of a protein to reactive compounds incorporated into the liposomes membrane; noncovalent hydrophobic binding of modified proteins during liposome formation or by the incubation with preformed liposomes); and indirect binding, including covalent binding of immunoglobulin protein via a polymer to the liposome (see Torchilin, V. P. CRC Critical reviews in Therapeutic Drug Carrier Systems, vol. 2(1)). Binding of the nucleic acid-ligand complex to the receptor facilitates uptake of the nucleic acid by receptor-mediated endocytosis.

A nucleic acid-ligand complex linked to adenovirus capsids, which naturally disrupt endosomes, thereby releasing material into the cytoplasm, can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122–2126).

Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest, or can be non-selective with respect to the target cell type.

The precise stoichiometric ratio of the various components of the complex or mixture according to the invention can be varied in order to control the magnitude of the initial immune response, the efficiency of delivery and the degree of specific targeting to APCs or related cells. Generally, the ratio of the nucleic acid encoding a first epitope to the amino acid sequence encoding the second epitope will be in the range of 1:10,000 to 1,000:1, with a preferred range of 1:1,000 to 100:1, and a most preferred range of 1:200 to 10:1.

A) Nucleic Acid Vectors Useful for Non-viral Delivery

The invention contemplates the use of a vector containing the gene of interest (i.e., the gene encoding an antigen for which an immune response is desired). The vector may be carried in a delivery vehicle which is targeted or untargeted for cell delivery, as described above. Vectors useful according to the invention will include vectors that integrate into host cell nuclear DNA or stable episomal vectors.

Episomal Vectors

Extrachromosomal replicators, generally, in addition to their origin function, encode functions that assure equal distribution of replicated molecules between daughter cells at cell division. In higher organisms, different mechanisms exist for partitioning of extrachromosomal replicators. For example, artificial (ARS-containing) plasmids in yeast utilize chromosomal centromeres as extrachromosomal replicators (Struhl et al., 1979, Proc. Natl. Acad. Sci. USA, 76:1035–1039). In metazoan cells, one well studied example of a stable extrachromosomal replicator exists—the latent origin oriP from Epstein-Barr Virus (EBV). The maintenance function of EBV requires the viral replication factor EBNA-1 and a series of binding sites for EBNA-1 termed the family of repeats (FR). Replication from oriP requires cis-acting elements (the Family of Repeats—FR and the dyad symmetry element) and the viral origin-binding protein, EBNA-1 (Yates et al., Proc. Natl. Acad Sci. USA, 81, 3806–3810 (1984); Yates et al., Nature 313:812–815 (1985)). FR has an effect on the stable extrachromosomal replication of the oriP by nuclear retention of the FR containing plasmids in mitosis. This activity directs plasmids into the newly forming nucleus in the telophase stage of the cell division (Krysan et al., Mol. Cell. Biol. 9:1026–1033 (1989)).

Particularly preferred vectors useful according to the invention are maintained at a high copy number in dividing and non-dividing cells of a patient. This may be achieved by employing an episomal vector such as the BPV-1 vector system described in WO 94/12629 and in Piirsoo et al., 1996, EMBO Jour. 15:1, comprising a plasmid harboring the BPV-1 origin of replication (minimal origin plus minichromosomal maintenance element) and optionally the E1 and E2 genes. The BPV-1 E1 and E2 genes are required for stable maintenance of a BPV episomal vector. These factors ensure that the plasmid is replicated to a stable copy number of up to thirty copies per cell independent of cell cycle status. The gene construct therefore persists stably in both dividing and non-dividing cells. This allows the maintenance of the gene construct in cells such as hemopoietic stem cells and more committed precursor cells.

"Minimal origin of replication" (MO) refers to a minimal cis-sequence within a papilloma virus that is necessary for initiation of DNA synthesis. The MO of BPV-1 is located at the 3' end of the upstream regulatory region within a 60 base pair DNA fragment (7914–7927) including an AT-rich region, a consensus sequence to which all papilloma viral E2 proteins bind, and an E1 protein binding site spanning nucleotide 1. The MO of HPV is located in the URR fragment (nt 7072–7933/1–99) (Chiang et al. Px,oc. Natl. Acad. Sci. USA 1992).

"E1" refers to the protein encoded by nt 849–2663 of BPV subtype 1; or to nt 832–2779 of HPV of subtype 11, or to equivalent E1 proteins of other papillomaviruses, or to functional fragments or mutants of a papillomavirus E1 protein, i.e., fragments or mutants of E1 which possess the replicating properties of E1.

"E2" refers to the protein encoded by nt 2594–3837 of BPV subtype 1; or to nt 2723–3823 of HPV subtype 11, or to equivalent E2 proteins of other papillomaviruses, or to functional fragments or mutants of a papillomavirus E2 protein, i.e., fragments or mutants of E2 which possess the replicating properties of E2.

"Minichromosomal maintenance element, (MME) refers to a region of the papilloma viral genome to which viral or human proteins essential for papilloma viral replication bind, which region is essential for stable episomal maintenance of the papilloma viral MO in a host cell, as described in Piirsoo et al. Preferably, the MME is a sequence containing multiple binding sites for the transcriptional activator E2. The MME in BPV is herein defined as the region of BPV located within the upstream regulatory region which includes a minimum of about six sequential E2 binding sites, and which gives optimum stable maintenance with about ten sequential E2 binding sites. E2 binding site 9 is a preferred sequence for this site, as described hereinbelow, wherein the sequential sites are separated by a spacer of about 4–10 nucleotides, and optimally 6 nucleotides. E1 and E2 can be provided to the plasmid either in cis or in trans, also as described in WO 94/12629 and in Piirsoo et al. "E2 binding site" refers to the minimum sequence of papillomavirus double-stranded DNA to which the E2 protein binds. An E2 binding site may include the sequence 5' ACCGTTGC-CGGT 3', (SEQ NO:12) which is high affinity E2 binding site 9 of the BPV-1 URR; alternatively, an E2 binding site may include permutations of binding site 9, which permutations are found within the URR, and which consist essentially of the consensus sequence 5'ACCN6GGT3', (SEQ NO:13) where N is, independent of its position, any nucleotide, and 6 refers to six independent nucleotides (N). One or more transcriptional activator E2 binding sites are, in most papillomaviruses, located in the upstream regulatory region, as in BPV and HPV.

A vector useful according to the invention may include a region of BPV between 6959–7945/1–470 on the BPV genetic map (see WO 94/12629), which region includes an origin of replication, a first promoter operatively associated with a gene encoding an antigen or epitope thereof, the BPV E1 gene operatively associated with a second promoter to drive transcription of the E1 gene; and the BPV E2 gene operatively associated with a third promoter to drive transcription of the E2 gene.

The promoters which drive expression of the E1 and E2 genes may be identical or different, and may be a tissue-specific promoter, such as the immunoglobulin, heavy chain promoter/enhancer for B-cell and the heavy or light chain promoters for blood cell expression, or from ubiquitously expressed genes, for example from the phosphoglycerolkinase, IE-CMV, RSV-LTR or DHFR genes. The arrangement of E1 and E2 genes relative to the BPV origin of replication may mimic the natural orientations of the sequences in the BPV genome, or it may assume a variety of other orientations, the choices of which will be apparent to one of skill in the art One skilled in the art will recognize that a variety of vectors will work according to the invention.

2. Delivery to APCs Mediated by Viral Vectors

In another preferred approach for introducing nucleic acid and an antigen into an antigen presenting cell, a viral vector containing the nucleic acid is used for transfer. Infection of cells with a viral vector has the advantage that a large proportion of cells receive the nucleic acid. Additionally, molecules encoded within the viral vector are expressed efficiently in cells which have taken up the vector nucleic acid.

1. Retroviruses: Defective retroviruses are well characterized for use in gene transfer for gene therapy purposes (for a review see Miller, A. D. (1990 Blood 76:271). A recombinant retrovirus can be constructed having a nucleic acid encoding an antigen of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14, and other standard laboratory manuals. Examples of suitable retroviruses include pLJ, pZIP, pWE and pEM which are well known to those skilled in the art. Examples of suitable packaging virus lines include ψCrip, ψCre, ψ2, and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad Sci. USA 88:8377–8381; Chowdhury et al. (1991, Science 254:1802–1805; van Beusechem et al. (1992) Proc. Natl. Acad Sci. USA 89:7640–7644; Kay et al. (1992) Human Gene Therapy 3:641–647; Dai et al. (1992) Proc. Natl. Acad Sci. USA 89:10892–10895; Hwu et al. (1993) J. Immunol. 150:4:104–115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

2. Adenoviruses: The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 d1324 or other strains of adenovirus (e.g., Adz, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad. Sci. USA 90:2812–2816) and muscle cells (Quantin et al. (1992) Proc. Natl. Acad. Sci. USA 89:2581–2584). Many replication-defective adenoviral vectors are deleted for all or parts of the viral E1 and E3 genes but retain as much as 80% of the adenoviral genetic material.

3. Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1 992) 158:97–129). It exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol 62:1963–1973). Vectors containing as little as 300 base pairs of AAV can be packaged and can integrate. Space for exogenous nucleic acid is limited to about 4.5 kb. An AAV vector such as that described in Tratschin et al. (1985) Mol. Cell. Biol. 5:3251–3260 can be used to introduce nucleic acid into cells. A variety of nucleic acids have been introduced into different cell types using AAV vectors (see for example Hermonat et al. (1984) Proc. Natl. Acad. Sci. USA 81 :6466–6,470; Tratschin et al. (1985) Mol. Cell. Biol. 4:2072–2081; Wondisford et al. (1988) Mol. Endocrinol. 2:32–39; Tratschin et al. (1984) J. Virol.51 :611 619; and Flotte et al. (1993) J. Biol. Chem. 268:3781–3790).

The delivery vehicle also may comprise a viral antigen such as any of those described above, wherein one or more of the viral proteins has been modified to include an epitope (s) to which an immune response is desired.

3. Tissue-restricted Gene Expression

Alternatively or in addition to the use of targeted delivery vehicles, DNA regulatory elements which lead to expression in APCs, their stem cells or other precursor cell types can be used according to the invention.

Tissue specific expression is provided according to the invention using genetic control elements which restrict expression of the gene with which the element is associated to a tissue for which the element is specific. Examples of such genetic control elements include locus control regions and tissue-specific promoters and enhancers.

Locus Control Regions (LCRS) (Grosveld et al., Cell 51:975–985, 1987), also known as Dominant Activator Sequences, Locus Activating Regions or Dominant Control Regions, are responsible for conferring tissue specific, integration-site independent, copy number dependent expression on transgenes integrated into chromatin in host cells. First discovered in the human globin gene system, which was prone to strong position effects when integrated into the chromatin of transgenic mice or mouse erythroleukaemia (MEL) cells (Magram et al., Nature 315:338–340, 1985; Townes et al., EMBO J. 4:1715–1723, 1985; Kollias et al., Cell 46:89–94, 1986; Antoniou et al., EMBO J. 7:377–384, 1988), LCRs have the ability to overcome such position effects when linked directly to transgenes (Grosveld et al., supra). Numerous LCRs have been defined in the art, including but not limited to the 0-globin and CD2 LCRs (Greaves et al., 1989), the macrophagespecific lysozyme LCR. (Bonifer et al., 1985, 1990), and a class II MHC LCR (Carson et al., Nucleic Acids Res. 21, 9:2065–2072, 1993).

Preferred regulatory elements include locus control regions (LCRS) such as the MHC class II LCR. Other control regions, for example, the Ig LCR for B cells, may also be used provided they lead to expression in APCs, their stem cells or other precursor cell types.

Vectors encoding elements permitting immune system evasion. Vectors useful according to the invention also may encode a sequence which serves to protect certain antigenic determinants encoded by the vector from viability to the host immune system. Thus, if the host mounts an immune response to determinants encoded by the vector, or carried on a vehicle used to deliver the nucleic acid to the antigen presenting cell, then this antigenicity may be eliminated or reduced by introducing into the open reading frame of the antigenic protein sequences from the Epstein bar virus EBNA-1 protein encoding a glycine-containing repeat, that suppresses antigen presentation of amino acid sequences linked in cis. See for example, Levitskaya et al., 1995, Nature 375:685.

A DNA sequence encoding a Glycine-containing sequence (for example, residues 93–325 of the Epstein-Barr virus nuclear antigen-1, carried on an Ncol-Apal fragment of EBNA1 (strain B95.8)) is inserted into a selected site within a gene encoding a protein which is believed or known to be immunogenic, but for which no immune response is desired upon administration of a nucleic acid according to the invention. The Glycine-encoding DNA sequence may, for example, be inserted downstream of the protein which is desired to be non-immunogenic, or downstream of an epitope of the protein which is known to be immunogenic; for example, it may be joined to the protein via an in-frame fusion at the carboxy or amino terminus of the protein, or inserted anywhere within the protein to render that protein nonimmunogenic. It is preferred that the Glycine-containing sequence is inserted within the protein at a distance wherein either terminal residue of the glycine-containing sequence is at a distance of between about 1 and 300 residues from an immunogenic epitope of the protein. In the case of a protein which contains multiple epitopes, it is believed that all epitopes of the antigenic protein will be rendered non-antigenic according to this embodiment of the invention. Preferably, the distance between the site of insertion in the protein. of the glycine-containing sequence and one amino acid of the protein epitope is between about 1 and 200 residues, more preferably 10–100 residues, and most preferably between about 20 and 50 residues. As used herein, "epitope" refers to an antigenic region of about 6–20 amino acids within a protein that is immunologically recognized as foreign.

For example, where the vector used to deliver a nucleic acid encoding an antigen to antigen presenting cells according to the invention contains the BPV E1 and E2 proteins, it is possible that the E1 and E2 proteins may cause an undesired immune response. Therefore, insertion of a glycine-containing sequence into each reading frame of these proteins may be accomplished in order to reduce or eliminate an immune response to the E1 and E2 proteins, without appreciably affecting the desired immune response to the antigen encoded by the vaccinating nucleic acid.

Glycine-containing sequence useful for obtaining masking of selected foreign proteins or immunogenic epitopes, such as those carried in vectors useful according to the invention, comprise a recombinant glycine-containing amino acid sequence having the formula: $[(Gly_a)X(Gly_b)Y(Gly_c)Z]n$, wherein each $Gly_a$, $Gly_b$, $Gly_c$, independently, may be one, two, or three sequential glycine residues; each of X, Y and Z is, independently, a hydrophobic or polar amino acid without a ring structure and having a side-chain of less than 3 atoms, wherein each of X, Y and Z, respectively, need not be identical from n repeat to n repeat; and n may be from 1–66.

It is preferred that each of X, Y and Z is, independently, selected from the group consisting of Ala, Ser, Val, Ile, Leu and Thr; more preferably, each of X, Y and Z is, independently, one of Ala and Ser; most preferably, each of X, Y and Z is, independently, Ala; more preferably, each of X and Y is not Met or Cys.

It is also preferred that the glycine-containing sequence comprises (GlyGlyXGlyYGlyZ) and n=7 repeats; or (GlyGlyXGlyYGlyGlyZ) in n=9 repeats where the remaining n repeats comprise $(Gly_a)X(Gly_b)Y(Gly_c)Z$ up to a total repeat number of 66, and preferably 28 total repeats; or the glycine-containing sequence is (GlyGlyXGlyYGlyGlyGlyZ) in n=7 repeats where the remaining n repeats comprise $(Gly_a)X(Gly_b)Y(Gly_c)Z$ up to a total repeat number of 66, and preferably 28 total repeats; or the glycine-containing sequence comprises (GlyGlyAlaGlyAlaGlyGlyla (SEQ ID NO:14) in n=9 repeats where the remaining n repeats comprise $(Gly_s,)X(Gly_b)Y(Gly_c)Z$ up to a total repeat number of 66, and preferably 28 total repeats.

It is also preferred that the glycine-containing sequence is (GlyGlyAlaGlyAlaGlyGlyGlyAla) (SEQ ID NO:15) in n=7 repeats where the remaining n repeats comprise $(Gly_a)X(Gly_b)Y(Gly_c)Z$ up to a total repeat number of 66, and preferably 28 total repeats; or the glycine-containing sequence is (GlyGlyXGlyYGlyGlyZ) in n=9 repeats and (GlyGlyXGlyYGlyGlyGlyZ) in n=7 repeats where the remaining n repeats comprise (Gly.) $X(Gly_b)Y(Gly,)Z$ up to a total repeat number of 66.

The glycine-containing sequence (GlyGlyAlaGlyAlaGlyGlyAla) in n=9 repeats and (GlyGlyAlaGlyAlaGlyGlyGlyAla) in n=7 repeats is also preferred, where the remaining n repeats comprise $(Gly_a)X(Gly_b)Y(Gly_c)Z$ up to a total repeat number of 66.

Antigens and Genes Encoding Antigens Useful According to the Invention

It is contemplated according to the invention that an immune response may be elicited via presentation of any protein or peptide capable of eliciting such a response. It is preferred that the antigen is a key epitope which gives rise to a strong immune response to a particular agent of infectious disease. If desired, more than one antigen or epitope may be encoded by the nucleic acid in order to increase the likelihood of an immune response. Thus, the vector may include a multi-gene construct in which the antigens encoded by the genes are coordinately expressed. If desired, all of the open reading frames of a pathogen's genome may be arranged together (as an expression library) in a vector in order to form a region of coding sequences which are expressed and presented by the antigen presenting cell. The use of expression libraries is described in Barry et al., 1995, Nature 377:632.

Alternatively, DNA sequences encoding antigens specific for different diseases or infectious agents-may be arranged together in a vector for delivery to and expression in an antigen presenting cell. Therefore, immune protection may be elicited against a number of diseases specified by the antigens encoded within the construct.

In a further embodiment of the present invention the antigen encoding nucleic acid sequence may contain a signal sequence for secretion of the antigen outside the cell. Signal sequences useful in the present invention are well known to those skilled in the art and are, for example, described in Blobel and Dobberstein (1975), J. Cell Biol., 6-1, 852–862. The secreted antigen will be taken up by the secreting cell and other neighbouring cells, processed as an exogenous antigen, and presented in association with Class II MHC. The delivery vehicle of the present invention may contain a mixture of nucleic acids encoding an antigen, some with, and some without, the secretion signal sequence. Thus secreted and non-secreted antigen can be produced in the same cell and both Class I and Class II MHC presentation can be produced after a single transfection event.

Antigens Useful According to the Invention are as Follows

1. Viral Antigens

Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS 1, NS 1, NS 1-NS2A, 80%E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

2. Bacterial Antigens

Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; Mycobacterium tuberculosis bacterial antigens such as mycolic acid, heat shock protein 65 (HSP65), the 30 kDa major secreted protein, antigen 85A and other mycobacterial antigen components; Helicobacter pylori bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus influenza bacterial antigen components; anthrax bacterial antigens such as anthrax protective antigen and other anthrax bacterial antigen components; rickettsiae bacterial antigens such as romps and other rickettsiae bacterial antigen components. Also included with the bacterial antigens described herein are any other bacterial, mycobacterial, mycoplasmal, rickettsial, or chlamydial antigens.

3. Fungal Antigens

Fungal antigens which can be used in the compositions and methods of the invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components, and tinea fungal antigens such as trichophytin and other coccidiodes fungal antigen components.

4. Parasite Antigens

Examples of protozoa and other parasitic antigens include, but are not limited to, plasmodium falciparum antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75–77 kDa antigen, the 56 kDa antigen and other trypanosomal antigen components 5. Tumor Antigens Tumor antigens which can be used in the compositions and methods of the invention include, but are not limited to, prostate specific antigen (PSA), telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the invention that antigens from any type of tumor cell can be used in the compositions and methods described herein.

6. Antigens Involved in Autoimmunity

Antigens which have been shown to be involved in autoimmunity and could be used in the delivery vehicles of the present invention to induce tolerance include, but are not limited to, myelin basic protein, myelin oligodendrocyte glycoprotein and proteolipid protein of multiple sclerosis and CII collagen protein of rheumatoid arthritis.

It is known that bacterial DNA can have immunostimulatory properties (Tokunaga et al., J. Nat. Cancer Insti., 1984, 72:955; Togunaga et al., Microbiol. Immunol. 1992, 36:55). Thus, for a nucleic acid encoding any one or more of the above-described antigens, it is preferred that the nucleic acid has immunostimulatory properties and may contain specifically identified CpG motifs that have been demonstrated to confer immunostimulation (Krieg et al., Nature, 1995, 374:546; Yi et al., Jour. Immunol., 1996, 156:558)

DOSAGE, ROUTE OF ADMINISTRATION AND PHARMACEUTICAL FORMULATIONS

According to the present invention, nucleic acid encoding one or more antigens or epitopes thereof may be used in gene therapy in order to provide immune protection against various infectious agents and diseases. The nucleic acid may be delivered to antigen presenting cells as part of a vehicle for delivering a nucleic acid to a cell which may specifically target a cell type or which may be untargeted with respect to the recipient cell. Delivery of a nucleic acid to APCs according to the present invention may be accomplished via ex vivo gene therapy or in in vivo gene therapy. For prophylactic and therapeutic vaccines, in vivo gene therapy is preferred, and for therapeutic vaccines, ex vivo gene therapy also is appropriate. A gene may be delivered to cells cultured ex vivo prior to reinfusion of the transfected cells into the patient or the gene may be delivered in a gene delivery vehicle complex by direct in vivo injection into the patient's vascular system or in a body area rich in the target cells. The in vivo injection may be made subcutaneously, intravenously, intramuscularly or intraperitoneally. The delivery vehicle may also be delivered by oral, nasal, vaginal or urethral routes, and may be delivered in combination with other delivery vehicles such as microspheres, gene gun, or Bioject™. Techniques for ex vivo and in vivo gene therapy are known to those skilled in the art. Generally, the compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection desired. Suitable dosage ranges are on the order of, where ex vivo transfected cells are administered to a patient, $10^5$–$10^8$, and optionally $10^6$–$10^7$ cells are administered in a single dose; where a gene/delivery vehicle complex is administered 100 ng–10 mg, or 1 µg–1 mg, or optionally 1 µg–10 µg of complex or mixture is administered in a single dose. Suitable regimens for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of a composition of this invention will depend, inter alia, upon the administration schedule, the unit dose of antigen administered or expressed by an encoding nucleic acid that is administered, whether the compositions are administered in combination with other therapeutic agents, the immune status and health of the recipient, and the therapeutic activity of the particular nucleic acid molecule, delivery complex, or ex vivo transfected cell.

Complexes and mixtures according to the invention also may be mixed in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Upon administration with a composition as described herein, via injection, oral, transdermal, or other routes, the immune system of the host will respond to the polypeptide antigen or the nucleic acid encoded antigen and the polypeptide antigen by producing either an effective cellular or humoral immune response to the antigen(s) or both effective cellular and humoral immune responses, as described herein.

Compositions of the invention can be given in a single dose schedule, or in a multiple dose schedule. A multiple dose schedule is one in which a primary course of vaccination can include 1–10 separate doses, followed by other doses given at subsequent time intervals required to maintain and or reinforce the immune response, for example, at 1–4 months for a second dose, and if needed, a subsequent dose(s) after several months. Periodic boosters at intervals of 1–5 years, usually 3 years, may be desirable to maintain the desired levels of protective immunity. The course of the immunization can be followed by in vitro proliferation assays of peripheral blood lymphocytes (PBLS) co-cultured with ESAT6 or ST-CF, and by measuring the levels of IFN-γ released from the primed lymphocytes. The assays can be performed using conventional labels, such as radionucleotides, enzymes, fluorescent labels and the like. These techniques are known to one skilled in the art and can be found in U.S. Pat. Nos. 3,791,932; 4,174,384; and 3,949,064, which are hereby incorporated by reference.

In addition to allowing maximization of the immune response, the ability to co-deliver DNA and antigen to APCs has the advantage of being able to modulate the type of immune response induced. It is known that DNA immunization tends to produce a T helper-type 1 (Th1) response, whereas protein immunization induces a T helper-type 2 (Th2) response (Raz et al., 1996, PNAS 93:5141). Thus, by manipulation of the DNA and protein/peptide components of the complex or mixture of the invention, the type of immune response may be manipulated by varying the relative amounts of each component.

Complexes and mixtures of the invention also may find use as diagnostic reagents. For example, they may be used to determine the susceptibility of a particular individual to a treatment regimen which employs the complexes or mixtures, and thus may be helpful in modifying an existing treatment protocol or in determining a prognosis for an affected individual. In addition, they may be used to predict which individuals will be at substantial risk for developing an infection by an organism, pathogen or agent for which vaccination is desired.

The invention may be used to generate both prophylactic and therapeutic immune responses. Optionally, the immune system can be primed and boosted either using the same complex or mixture or using combinations of different complexes or mixtures described herein, or combinations of complexes or mixtures described herein with conventional vaccines known in the art, e.g., recombinant protein vaccines or killed virus vaccines.

EXEMPLIFICATION

1. The Following Examples Demonstrate Cell Type-specific Expression in Antigen Presenting Cells in Animal Models Cell Type-specific Expression of the Human Glucocerebrosidase Gene in Cells of the Monocyte-macrophage Lineage in several Lines of Transgenic Mice A construct was generated in which the mouse MHC class II Ea gene Locus Control Region (LCR, Carson and Wiles, Nucl. Acids Res., 21, (2065–2072 (1993)) was linked to the human gene encoding glucocerebrosidase (GC). Several transgenic lines were made with linearized DNA of this construct. Expression of human GC and functional activity was detectable in the spleen cells of most transgenic lines. Non-transgenic mice (ntg) had no detectable human GC activity. The spleen contains both B lymphocytes and macrophages/dendritic cells, and so to definitively demonstrate expression in macrophages/dendritic cells, enriched populations of activated, transgenic macrophages w ere produced by thioglycollate injection into the peritoneum of transgenic mice. Analysis of the resulting macrophage populations for expression of human GC showed that F4/80- positive macrophages (Gordon et al., Curr. Topics. Microbiol. immunol., (1992) 181, 1–37) abundantly expressed human GC (as detected by monoclonal antibody 8E4). This demonstrates APC-specific expression of the heterologous gene rising the MHC LCR.

In Vivo Vaccination: Generation of Transgenic Mice Expressing Influenza NP Under MHC LCR Control, and Generation of Anti-NP Immunity in Syngeneic Non-transgenic Littermates by Transplantation of Transgenic Spleen and Bone Marrow Cells To demonstrate that expression of foreign proteins in the APC can generate protective cellular and/or-humoral immune responses, transgenic lines are made in which the Influenza NP gene is expressed under the control of the MHC class II Ea LCR as described above.

From these mice, spleen cells or bone marrow cells are isolated and infused into non-transgenic syngeneic mice. Mice are then analyzed for expression of the NP gene, which is expected to be present in the donor cells and their differentiated descendants. Analysis of the transplant recipients is expected to reveal that some have successfully generated NP-specific cytotoxic T cells and anti-NP antibody responses.

Anti-influenza Vaccines to Generate Immunity Directed Against the Hemagglutinin Component of the Viral Capsid Transgenic lines are made in which the Influenza Hemagglutinin (HA) gene is expressed under the control of the MHC class II Ea LCR described above. From these mice, spleen cells or bone marrow cells are isolated and infused into non-transgenic syngeneic mice. Mice are then analyzed for expression of the HA gene, which is shown to be present in the donor cells and their differentiated descendants. Analysis of the transplant recipients is expected to reveal that some have successfully generated HA-specific cytotoxic T cells and anti-HA antibody responses.

Anti-HIV Vaccines

Transgenic mice are made expressing HIV-1 tat, rev, nef or gag genes, and combinations thereof, under the control of the MHC class II Ea LCR described above. Transplantation of transgenic spleen cells to syngeneic non-transgenic mice is expected to elicit a cytotoxic T cell response which can be measure in vitro using Chromium$^{51}$ release assays for T cell-mediated cytotoxicity. To measure the T cell response, T cells from transplantation recipients are challenged with syngeneic, non-transgenic, irradiated, Cr$^{51}$-labeled target Antigen-Presenting Cells in the presence of immunodominant peptides from the HIV-1 nef, rev, gag and tat proteins. Effective T cell responses are detected by measuring Cr$^{51}$ release as a result of target cell lysis. Serum antibody responses against HIV-1 nef, rev, gag and tat are also measured in the transplant recipients, to confirm the generation of a humoral response.

Anti-hepatitis B Virus (HBV) Vaccines

Transgenic mice are made expressing the HBc, HBe, S, pre-S and pX genes, and combinations thereof, under the control of the MHC class II Ea LCR. Transplantation of transgenic spleen cells to syngeneic non-transgenic mice is expected to elicit a cytotoxic T cell response which can be measured in vitro using Chromium$^{51}$ release assays for T cell-mediated cytotoxicity. To measure the T cell response, T cells from transplantation recipients are challenged with syngeneic, non-transgenic, irradiated, Cr$^{51}$-labeled target Antigen-Presenting Cells in the presence of immunodominant peptides from the HBc, HBe, S, pre-S, and pX proteins. Effective T cell responses are detected by measuring Cr$^{51}$ release as a result of target cell lysis. Serum antibody responses against the HBc, HBe, S, pre-S, and pX proteins are also measured in the transplant recipients, to confirm the generation of a humoral response.

Anti-hepatitis C Virus (HC7V) Vaccines

Transgenic mice are made expressing nucleocapsid protein C22-3, the NS3 and NS4-region derived C200 and C33c proteins, and combinations thereof, under the control of the MHC class II Ea LCR. Transplantation of transgenic spleen cells to syngeneic non-transgenic mice is expected to elicit a cytotoxic T cell response which can be measured in vitro using Chromium$^5$ release assays for T cell-mediated Cytotoxicity. To measure the T cell response, T cells from transplantation recipients are challenged with syngeneic, non-transgenic, irradiated, Cr$^{51}$-labeled target Antigen-Presenting Cells in the presence of immunodominant peptides from nucleocapsid protein C22-3, the NS3 and NS4-region derived C200 and C33c proteins. Effective T cell responses are detected by measuring Cr$^{51}$ release as a result of the target cell lysis. Serum antibody responses against the nucleocapsid protein C22-3, the NS3 and NS4- region derived C200 and C22c proteins are also measured in the transplant recipients, to confirm the generation of a humoral response.

Anti-human Papilloma Virus (HPV) Vaccines

Transgenic mice are made expressing the HPV 16 proteins E1, E2, E7, E5 and E6, and combinations thereof, under the control of the MHC class II Ea LCR. Transplantation of transgenic spleen cells to syngeneic non-transgenic mice is expected to elicit a cytotoxic T cell response which can be measured in vitro using Chromium$^{51}$ release assays for T cell-mediated cytotoxicity. To measure the T cell response, T cells from transplantation recipients are challenged with syngeneic, non-transgenic, irradiated, Cr$^{51}$-labeled target Antigen-Presenting cells in the presence of immunodominant peptides from the E1, E2, E7, E5 and E6 proteins. Effective T cell responses are detected by measuring Cr$^{51}$ release as a result of target cell lysis. Serum antibody responses against the E1, E2, E7 E5 and E6 proteins are also measured in the transplant recipients, to confirm the generation of a humoral response.

Anti-tumor Vaccines

Lines of transgenic mice are made expressing the genes encoding the melanoma-specific antigen MAGE-1, tyrosinase, the murine homologue of the HER2/neu proto-oncogene which is mutated in ovarian and breast tumors, the HPV 3.6 E7 protein, and the connexin 37 protein which is mutated in the 3LL lung carcinoma. Bone marrow and spleen cells of these transgenic mice are transplanted to syngeneic non-transgenic mice to elicit cytotoxic T-cell mediated and humoral immune response to the proteins encoded by the transgenes. MAGE-1/tyrosinase, HER2/neu, HPV-16 E7, and connexin 37 transgenic-transplant recipients and untransplanted controls are subsequently injected subcutaneously with tumor cells from the B16 mouse melanoma, murine mammary carcinoma T5O/80, the 3LL mouse lung carcinoma, or the C3 mouse tumor transfected with HPV 16 genomic DNA, respectively, and tumor growth is monitored. Transplant recipients are expected to show much reduced tumor growth than non-transplanted controls, confirming that protective anti-tumorimmune responses-have been generated.

Moreover, non-transplanted recipients already bearing tumors of the types described above are expected to be cured of their cancers by an infusion of bone marrow or spleen cells from syngeneic mice transgenic for the corresponding tumor-specific antigen-coding gene also described above.

2. Examples of Gene Therapy Using the Delivery Vehicle of the Present Invention

Anti-influenza Vaccines to Generate Immunity Directed Against Hemagglutinin Component of the Viral Capsid A delivery vehicle comprising a plasmid vector in which the Influenza Hemagglutinin (HA) gene is expressed under the control of the MHC class II Ea LCR described above, is administered to subjects by direct intravascular injection or by transfection of cultured bone marrow-derived cells in vitro which are then reinfused into patients intravenously. Subsequent analysis of the patients is expected to reveal that some patients have successfully generated HA-specific cytotoxic T cells and anti-HA antibody responses.

A delivery vehicle comprising a plasmid vector in which nucleotide sequences from the influenza matrix protein gene encoding a peptide including the HLA A2 restricted epitope located at residues 57–68 (Goton et al, 1987, Nature 326:331–332. Moss et al 1991, PNAS 88:8987–8990) are expressed under the control of the MHC class II Ea LCR described above is administered to patients by direct intravascular injection or by transfection of cultured bone marrow-derived cells in vitro which are then reinfused into patients intravenously. Subsequent analysis of the patients is expected to reveal that some patients have successfully generated HA-specific, cytotoxic T cells.

Anti-HIV Vaccines

A delivery vehicle comprising a plasmid vector in which the HIV-1 tat, rev, nef or gag genes, and combinations thereof, are expressed under the control of the MHC class II Ea LCR is administered to patients by direct intravascular injection or by transfection of cultured bone marrow-derived cells in vitro which are then reinfused into patients intravenously. Subsequent analysis of the patients is expected to reveal that some patients have successfully generated CTL responses against the HIV-1 nef, rev, tat and gag proteins. Effective T cell responses are detected by measuring $Cr^{51}$ release as a result of target cell lysis. Serum antibody responses against HIV-1 nef, rev, tat and gag are also measured in the transplant recipients, confirming the generation of humoral response.

A delivery vehicle comprising a plasmid vector containing nucleotide sequences from the HIV-1 gag gene which encode peptides including the HLAB27 and B8 restricted epitopes in HIV p17 Gag and HIV p24 Gag (Nixon et al. 1988, Nature 336:484–487, Nixon and McMichael, 1991 AIDS 5:1 eO49–1059) and combinations thereof, expressed under the control of the MHC class II Ea LCR, is administered to patients by direct intravascular injection or by transfection of cultured bone marrow-derived cells in vitro which are then reinfused into patients intravenously. Subsequent analysis of the patients is expected to reveal that some patients have successfully generated CTL responses against Gag protein sequences. Effective T cell responses are detected by measuring $Cr^{51}$ release as a result of target cell lysis.

Anti-hepatitis B Virus (HBV) Vaccines

A delivery vehicle comprising a plasmid vector in which HBV HBc, HBe, S, pre-S, and pX genes, and combinations thereof, are expressed under the control of the MHC class II Ea LCR is administered to patients by direct intravascular injection or by transfection of cultured bone marrow-derived cells in vitro which are then reinfused into patients intravenously. Subsequent analysis of the patients is expected to reveal that some patients have successfully generated CTL responses against the HBV HBc, HBe, S, pre-S, and pX proteins. Effective T cell responses are detected by measuring $Cr^{51}$ release as a result of target cell lysis. Serum antibody responses against HBV HBc, HBe, S, pre-S, and pX proteins are also measured in the transplant recipients, confirming the generation of humoral response.

Anti-hepatitis C Virus (HCV) Vaccines

A delivery vehicle comprising a plasmid vector in which the genes encoding the HCB nucleocapsid protein C22-3, the NS3 and NS4-region-derived C200 and C33c proteins, and combinations thereof, are expressed under the control of the MHC class II Ea LCR is administered to patients by direct intravascular injection or by transfection of cultured bone marrow-derived cells in vitro which are then reinfused into patients intravenously. Subsequent analysis of the patients is expected to reveal that some patients have successfully generated CTL responses against nucleocapsid protein C22-3, the NS3 and NS4-region-derived C200 and C22c proteins. Effective T cell responses are detected by measuring $Cr^{51}$ release as a result of target cell lysis. Serum antibody responses against nucleocapsid protein C22-3, the NS3 and NS4 region-derived C200 and C33c proteins are also measured in the transplant recipients, confirming the generation of a humoral response.

Anti-human Papilloma Virus (HPV) Vaccines

A delivery vehicle comprising a plasmid vector in which genes encoding the HPV 16 proteins E1, E2, E7 E5 and E6, and combinations thereof, are expressed under the control of the MHC class II Ea LCR, is administered to patients by direct intravascular injection or by transfection of cultured bone marrow-derived cells in vitro which are then reinfused into patients intravenously. Subsequent analysis of the patients is expected to reveal that some patients have successfully generated CTL responses against E1, E2, E7 E5 and E6 proteins. Effective T cell responses are detected by measuring $Cr^{51}$ release as a result of target cell lysis. Serum antibody responses are also measured in the transplant recipients, confirming the generation of a humoral response.

Anti-tumor Vaccines

A delivery vehicle comprising a plasmid vector in which genes encoding the melanoma-specific antigen MAGE-1, tyrosinase, the murine homologue of the HER2/neu proto-oncogene which is mutated in ovarian and breast tumors, and the HPV 16 E7 protein are expressed under the control of the MHC class II Ea LCR, is administered to patients by direct intravascular injection or by transfection of cultured bone marrow-derived cells in vitro which are then reinfused into patients intravenously. Subsequent analysis of the patients is expected to reveal that some patients have successfully generated CTL responses against MAGE-1, tyrosinase, HER2/neu or HPV E6 or E7 proteins. Effective T cell responses are detected by measuring $Cr^{51}$ release as a result of target cell lysis. Serum antibody responses against MAGE-1, tyrosinase, HER2/neu, or HPV E6 or E7 proteins are also measured in the transplant recipients, confirming the generation of humoral response. In addition tumor regression may be observed.

3. Examples of Delivery Systems That Allow Presentation of Antigen in Association With Class I and Class II MHC (In Vivo)

The following examples teach one of skill in the art how to differentiate MHC Class I and Class II responses in vivo, and how to obtain an increased MHC Class II-mediated immune response using a construct prepared and administered according to the invention.

Addition of Pentide/Protein to the Delivery Vehicle

To demonstrate that administration of a delivery system containing peptide/protein antigens gives rise to a greater helper T cell response (i.e. predominantly a class II restricted response) than administration of a delivery vehicle in which the antigen is solely encoded on the nucleic acid, mice are vaccinated with a delivery vehicle with or without antigenic peptides. The complex intended for delivery will have previously been tested for delivery of both antigen and DNA in vivo. Testing is performed by screening complex formulations for the ability to generate an immune response within the animals. Possible complex formulations include, but are not limited to, those described in International Patent Application No. PCT/GB96/01396. The DNA contained within the delivery vehicle either encodes no antigenic gene or the gene for influenza nucleoprotein. The antigenic peptides are appropriate, Class II presented, epitopes of NP or the whole NP protein. T cells from the immunized mice are then assayed for class I- and class II-restricted responses. When the delivery vehicle contained antigenic peptide/protein but no antigen gene a predominantly class II-restricted response is observed, whereas in the absence of both antigenic peptides/protein, and antigen gene, no class II-restricted response is seen. In the presence of the antigen gene, class I and class II responses are observed but the class II response is increased when antigenic peptides/protein are included on the delivery vehicle. Thus, addition of antigenic peptide/protein to the delivery vehicle produces an increased class II-restricted response. Class I-restricted CTL responses are measured by $Cr^{51}$ release assay and Class II-restricted helper T cell responses are measured by T cell proliferation assay or cytokine release assay.

Addition of Secretion Signal Sequence to Antigen Gene

To demonstrate that administration of a delivery vehicle containing DNA encoding an antigen gene with a secretion signal sequence that is functional in mammalian cells gives rise to a greater Class II response than administration of a delivery vehicle in which an non-secreted version of the antigen is produced, mice are vaccinated with a delivery vehicle containing a DNA molecule encoding the influenza nucleoprotein gene with or without a secretary signal sequence T cells from the immunized mice are then assayed for CTL and helper T cell responses in order to determine the predominantly class I- and class II-restricted response, respectively. The mice which had been immunized with the secreted form of NP show increased helper T cell (i.e. predominantly class II-restricted) responses when compared to immunization with the gene encoding the non-secreted antigen. Thus, addition of secretory signal sequence to the antigenic gene produces an increased helper T cell response (i.e. predominantly a class II-restricted response).

4. Examples of Delivery Systems That Allow Presentation of Antigen in Association With Class I and Class II MHC (In Vitro)

The following examples provide in vitro assays for differentiating MHC Class I and Class II immune responses, and for obtaining an increased MHC Class II immune response using constructs and methods according to the invention.

It has been shown that dendritic cells (DC) can be derived from Peripheral Blood Mononuclear Cells (PBMCs) in vitro by culturing with GM-CSF and IL-4 for one week (Romain et al. (1994) *J. Exp. Med.* 180:83), and that these cells can then be matured resulting in an increase in their ability to stimulate naive allogenic T cells and a decrease in their capacity to process antigen (Sallusto et al. (1994) *J. Exp. Med.* 179: 1109). This in vitro system has been utilised to assess the ability of the delivery vehicle to deliver antigens encoding genes and to assess their presentation by Class I or Class II MHC molecules.

Transfection of Dendritic Cells

To demonstrate that a complex according to the invention is able to transfect the in vitro matured dendritic cells (DC) described above, DC were transfected with peptide complexes containing pEGFP-NI (commercially available plasmid from Clonetech). The plasmid, pEGFP-NI encodes green fluorescent protein (GFP) which can be visualised by its natural fluorescence when visualised via a fluorescence microscope. The peptide complexes were made with 2 µg NBC9 and 0.6 µg LIP 9 per µg of pEGF-NI (Lip 9 is a N-palmityl derivative of NBC9 as described in International Patent Application No. PCT/GB96/01396). The complexes were made up by adding the following constituents in the following order mixing the sample well after each addition:

| | |
|---|---|
| NBC 9 (10 mg/ml in water) | 43.75 ml |
| Sterile milli-Q filtered water | 507.5 ml |
| 0.5M phosphate buffer, pH 7.4 | 43.75 ml |
| 5M NaCl | 105 ml |
| pEGFP-N1 (0.5 mg/ml) | 175 ml |
| Lip 9 (1 mg/ml) | 52.9 ml |

The mixture was incubated at room temperature for I hour and overnight at 4° C. 850 ml was then diluted into 3400 ml of PEG dilution buffer.

PEG dilution buffer:

10% PEG 8000

25 mM phosphate pH 7.4

37.5 mM NaCl

DC were generated as described by Romani et al. (J. Exp. Med. 1994 180:63–93). Briefly, PBMC were prepared from Buffy coats by standard protocols known in the art. The PBMC were resuspended in RPMI-1640, 10% FCS and were allowed to adhere to plastic dishes. After 2 hours at 37° C., 5% $CO_2$ the nonadherent cells were removed, the adherent cells were gently washed and subsequently cultured with GM-CSF (800 U/ml) and IL-4 (500 U/ml). The cultures were fed with cytokines every second day of culture. On day 7 of the culture, the cells were harvested and resuspended to $1.26 \times 10^6$ cells/ml in RAT medium (RPMI 1640, human serum albumin 1 mg/ml; human transferrin (partly saturated) 50 µg/ml). Using 6 well plates 12 µl of 10 mM chloroquine and 863 µl of DC were added to a well. 125µl of complex was then added per well and the cells were incubated at 37° C., 5% $CO_2$ for 4 hours. The cells were removed from the wells harvested and resuspended in I ml complete medium (RPMI-1640, 10% FCS) per well and return to the plate for a 24 hour incubation at 37° C., 5% $CO_2$. Each well was then harvested, cytospun onto a slide and tranfected cells were then visualised using a LEICA fluorescence microscope (positive cells appear bright). FIG. 3 shows a typical field of view.

To demonstrate that cells can be transfected with complexes that contain antigen and thus antigen and DNA can be delivered to the same cell.

COS and dendritic cells have been transfected with complexes consisting of K6Cl22 peptide and pCMVb (Clonetech) whereas COS cells incubated with an equivalent amount of naked DNA show no transfection.

K6Cl22 is a peptide that contains an epitope of influenza A nucleoprotein (A/NT/60/68), and a stretch of lysine residues for ionic interaction with the phosphate backbone of the DNA. Thus this peptide is an antigen-DNA binding fusion peptide. The sequence of the peptide is:

NH2-KKKKKKGGFLGFWRGENGRKTRSAYERMCNILKGK-COOH (SEQ ID NO:16)

Preparation of K6CL22 via Recombinant DNA Methods

K6CL22 may be prepared by expression of a nucleotide sequence encoding K6CL22. For example, the following sequence may be expressed in *E. coli*.

NH2-K K K K K K G G F L
5' AAA AAA AAG AAA AAA AAA GGT GGT TTG CTG
G F W R G E N G R K T R
GGT TTC TGG CGT GOT GAA AAC GGT CGT AAA ACC CGT
S A Y E R M C N I L K G
TCT GCT TAC GAA CGT ATG TGC AAC ATC CTG AAA GGT
K —COOH (SEQ ID NO:16)
AAA 3' (SEQ ID NO:17)

The polypeptide may be expressed from this sequence in any given expression system known in the art, and purified according to conventional purification techniques.

Synthesis of K6CL22 and LicK6CL22

The following abbreviations are used. Boc-t—-Butoxycarbonyl; Fmoc—Fluorenylmethoxycarbonyl; tBu—tButyl; Pbf-2,2,4,6,7-pentamethyldihydrobenzofuran-5-sulfonyl; PEG—polyethyleneglycol; PS—polystyrene; Trt—trityl; RP-HPLC—reverse phase high performance liquid chromatography.

Preparation of K6CL22 Peptide

K6CL22 (also referred to herein as K6CL22, K6CLII, CL22 or CLII) has the following amino acid sequence:

NH2-KKKKKKGGFLGFWRGENGRKTRSAYERMCNILKGK-COOH (SEQ ID NO:16).

K6CL22 was prepared by solid phase peptide synthesis on Fmoc-Lys (Boc)-O-PEG-PS-Resin at a 0.85 mmol scale. The synthesis was accomplished using a Biosearch 9050 plus Pepsynthesizer in extended synthesis cycle mode. Lysine and tryptophan side chains were Boc protected; arginine side chains were Pbf protected; serine, threonine and tyrosine side chains were tBu protected; the asparagine and cysteine side chain was Trt protected and glutamate side chains were tBu protected. The amino acid derivatives were coupled in a 3 molar excess using 0.6M O—(1H-benzotriazo-1-yl)tetramethyluronium tetrafluoroborate (TBTU) in dimethylformamide/0.9M N-ethyldiisopropylamine in dimethylformamide as activating agents. Deprotection of the N-terminal Fmoc group before each coupling was achieved using a solution of 20% piperidine in dimethylformamide (1 min at high flow rate followed by 10 min at 3 ml /min.). The coupling time for each residue was 1.5 h.

On completion, the resin conjugated peptide was washed with dichloromethane and dried. The peptide was cleaved from the resin using trifluoroacetic acid/triisopropylsilane/thioanisole/1,2-ethanedithiol (92.5: 2.5: 2.5: 2.5) for 1.5 h at room temperature, which simultaneously deprotected the amino acid side chains. The resin was then removed by filtration and washed with trifluoroacetic acid. The combined filtrate and washings were concentrated by evaporation then precipitated using diethyl ether followed by centrifugation to give the crude peptide. The crude peptide was dissolved in a minimum volume of 20 mM ammonium acetate, pH 4.6 and purified using a Sephadex G25 (Superfine) gel filtration column (100×2.6 cm) run in the same buffer. The fractions containing peptide, as determined by analytical RP-HPLC, were pooled and lyophilised. Further purification was achieved by preparative HPLC using a $C_{28}$ RP-HPLC column (Dynamax 83-221-C) and a gradient of 20–50% acetonitrile (0.1% trifluoroacetic acid) in water (0.1% trifluoroacetic acid) over 30 min. The fractions corresponding to the major peak on the chromatograph were pooled and lyophilised. Finally, the peptide was desalted using a Sephadex G15 (Medium) gel filtration column (70×2.6 cm) run in 20 mM ammonium acetate, pH 4.6. The peptide fractions, which were detected by analysis at 226 nm, were pooled and lyophilised. The pure peptide was stored at 20° C.

The peptide (expected molar mass 4101.9) was characterized using matrix assisted laser desorption/ionisation (MALDI) mass spectrometry. 0.1 –0.5 mg of peptide was dissolved in 1 ml of 0.1% triflucroacetic acid, and 0.5 µl applied to the target and analyzed using a Kratos Kompact MALDI II-tDE spectrometer.

Preparation of LIC-K6CL22 Lipopeptide

LIC-K6CL22 is a disulphide-linked cholesterol-K6CL22 conjugate with the following structure:

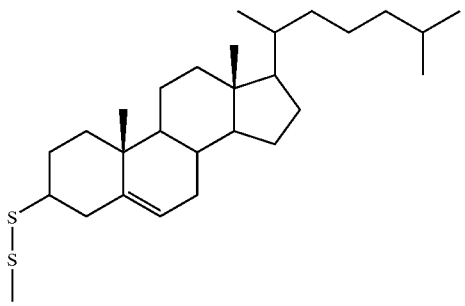

NH2- KKKKKKGGFLGFWRGENGRKTRSAYERM-CNILK
GK-COOH (SEQ ID NO: 16).

21.0 mg (97 µmol) 2,2'-dithiodipyridine was dissolved in 1 ml methanol and added to 40.0 mg (9.7 µmol) K6CL22 made up in 4 ml methanol. The reaction was left at room temperature for 1 h. The methanol was evaporated off under vacuum and 2 ml water added to the solid residue. The suspension was passed through a 0.4 µm filter, and the filtrate was injected onto a preparative $C_{18}$ RP-HPLC (Dynamax 83-221-C) column and purified using 0–30% acetonitrile (0.1% trifluoroacetic acid) in water (0.1% trifluoroacetic acid) gradient. The peptide containing fractions were pooled and lyophilised. 10 mg (45 µmol) modified K6CL22 were dissolved in 2 ml methanol and 0.5 mg 3β-thiocholesterol in 1 ml chloroform added. The solution was mixed and left at room temperature for 48 h. The solvents were evaporated off under vacuum and the residue dissolved in 2 ml water and filtered to remove excess lipid. The peptide was purified finally on a preparative $C_4$ RP-HPLC column (Dynamax 83-523-C5) using a 5–100% acetonitrile (0.1% triflucroacetic acid) in water (0.1% trifluoroacetic acid) gradient. The lipopeptide containing fractions were pooled and lyophilised.

The pure lipopeptide, LIC-K6CL22 (expected molar mass 4502.1), was characterized by mass spectrometry as described for K6CL22.

Structure of CL26 Peptide

CL26 has the following amino acid sequence:
H-KKKKKKKKKKKKGGFLGFWRGENGRKTRS
AYERMCNILKGK-OH (SEQ ID NO:18)

The amino acid composition of CL26 is identical to that of K6CL22 except a six lysine sequence extension at the-N-terminus.

Preparation of CL26 Peptide

CL26 was prepared by solid phase peptide synthesis using the method described for K6CL22. CL26 was purified using the method described for K6CL22.

The peptide (expected molar mass 4871.0) was characterised using matrix assisted laser desorption/ionisation (MALDI) mass spectrometry. 0.1–0.5 mg of peptide was dissolved in 1 ml of 0.1% trifluoroacetic acid, and 0.5 µl applied to the target and analysed using a Kratos Kompact MALDI II-tDE spectrometer.

Disulphide Formation to Form CL26 Dimer 1.0 ml of 20 mM ammonium bicarbonate was added to 10.0 mg free thiol containing CL26 peptide. The cysteine thiols were left to oxidise at 25° C. in a vial left open to the air. The progress of dimerisation was followed by observing the change in original retention time of the peptide by capillary electrophoresis. After 16 h the peptide was judged to have dimerised completely. Addition of 10 mM DTT to a peptide subsample reversed the observed shift in retention time. Dimer formation was also confirmed by gel filtration analysis using a Superdex Peptide (HR 10/30) column. Finally, the peptide was frozen and lyophilised to give the bicarbonate salt.

Preparation of K6CL22-DNA Complexes for PCS and Zeta Analysis and Transfection Assays K6CL22 concentration was determined by absorbance at 280 nm using $E^{280}_{0.1\%}=1.67$ cm$^{-1}$ DNA concentration was determined by absorbance at 260 nm using $E^{260}_{0.1\%}=20$ cm$^{-1}$.

Complexes between K6CL22 and DNA were formed in the following way in a laminar flow hood: A stock solution of K6CL22 (typically 8–12 mg/ml) was stored in water at −20° C. This was thawed and diluted to 4–400 µg/ml in either 10 mM HEPES pH7.4 (Hepes) or 10 mM HEPES/150 mM NaCl pH7.4 (HBS). (It should be noted that these non-reducing conditions favor the formation of peptide dimers via disulfide bonding between peptides of cysteine residues in the peptide). A stock solution of pCMVβ plasmid DNA (typically 2–4 mg/ml in either water or TE buffer) was diluted to 40 µg/ml in Hepes or HBS. Peptide (typically 0.4–1 ml) was added to an equal volume of diluted DNA. Different target ratios of Peptide:DNA were achieved by varying the concentration of added peptide. Samples were immediately mixed by gently sucking up and down in a pipette tip and left to incubate at room temperature for a minimum of one hour or if required overnight at 4° C. Peptide and DNA were mixed as described above and incubated over night at 4° C. The final DNA concentration was 40 µg/ml. The results indicate that small particles are formed at various ratios of peptide:DNA in HEPES buffer in the absence of added NaCl. However there is a particular ratio at which large particles/aggregates are formed. With this peptide the ratio is approx. 1.4:1 (peptide:DNA). Peptide and DNA were mixed as described above and incubated for one hour at room temperature. The final DNA concentration was 40 µg/ml.

The results show that in the presence of 150 mM NaCl large particles/aggregates of complex of approx. 100 nm are formed after one hour. Larger aggregates may form on further incubation. Little variation of size is observed with increased peptide/DNA ratio.

Photon Correlation Spectroscopy (PCS) Q Quasi-elastic Laser Light Scattering (QUELLS)

For PCS analysis the buffers used in the preparation of samples were filtered through 20 nm filters. Analyses were carried out at 25° C. and at an angle of 90° using a Malvern Instruments 4700 PCS instrument fitted with an argon-ion laser. Samples were allowed to equilibrate to 25° C. prior to measuring, and an average Zav was determined from a minimum of three measurements. Typically the laser power was set to 12 mW. The PMT aperture was 100 µm. Zav and intensity and volume distributions were determined using Malvern PCS software. Constants used in the software calculations were as follows: Viscosity=0.88 cP, RI medium=1.33, RI particle=1.6, Imaginary RI of particle=0.

Zeta Potential Analysis

Zeta potential was determined on samples prepared in Hepes using a Malvern Instruments Zetasizer 3000 fitted with a standard Zeta cell. The Zeta cell was first flushed with 20 nm filtered Hepes to equilibrate the cell followed by a pulse of air to blow out the buffer. A 2 ml sample was then loaded into the cell. The Zeta potential was determined from an average of 6 measurements for each sample. The data was analyzed using Malvern Zeta software with automatic settings, set for a positively zeta potential. Samples prepared in HEPES for PCS analysis were also analyzed for Zeta potential.

This graph indicates that as the peptide:DNA ratio is increased the zeta potential of the complex becomes less negative. At a ratio of 1.4:1 that zeta potential is zero. The results demonstrate that the average (Zav) particle size is approximately 100 nm, and aggregation is occurring at a ratio in the range of 1.2–1.6 $\mu$g peptide/$\mu$g DNA, with an average of 1.4.

Preparation of Transfection Complexes and Determination of Condensing Activity

A "transfection complex" as used herein, refers to a noncovalent association of K6CL22 and nucleic acid, that is, an association based on charge:charge(+:−) interaction between the negatively charged phosphate groups of the nucleic acid and the positively charged cationic groups (e.g., amino groups) of the peptide.

A transfection complex including K6CL22 and a nucleic acid comprises condensed nucleic acid at certain peptide-:nucleic acid ration.

One can determine whether or not a nucleic acid is condensed by a gel retardation assay in which condensed nucleic acid migrates slower or remains in the well of an agarose gel or a nondenaturing polyacrylamide gel.

Preparation of transfection complexes and a gel retardation assay is performed as follows.

Transfection complexes are prepared by combining nucleic acid and K6CL22 peptide under conditions which permit condensation of the nucleic acid. A concentration of nucleic acid is selected, for example, 20, 30, or 40 $\mu$g/ml and possibly 50, 60, 70, or 100 $\mu$g/ml, and prepared in a low salt buffer, e.g., 150 mM NaCl.

In one embodiment, the required amount of DNA is made up to 20 $\mu$g/ml in 150 mM NaCl; 25 mM HEPES, pH 7.4, or in 0.6 M NaCl; 25 mM HEPES, pH 7.4 and aliquotted between wells on a multiwell plate. The amount of conjugate or peptide required to give positive charge:phosphate ratios of between 0.1 and 5.0 is calculated. This is made up to an equal volume to the DNA aliquots (0.05–0.5 ml) in either 150 mM sodium chloride; 25 mM HEPES, pH 7.4 or 0.6M sodium chloride; 25 mM HEPES, pH 7.4. The plate containing the DNA is placed on a plate shaker and shaken while the peptide is added at a rate of 0.1 volume per minute. After addition of K6CL22 peptide is complete, the solution is incubated at room temperature for at least 30 minutes. A sample for each positive charge:phosphate ratio is subjected to electrophoresis on an agarose gel. The gel is stained with ethidium bromide and visualized under UV light. Condensed DNA remains n the well of the gel and does not migrate in the electric field.

Characteristics of the Transfection Complex
1) Overall Size

It is preferred according to the invention that the size of a transfection complex when formulated and measured by PCS fall within the range of 5 nm to 1500 nm. Complex size is measured by laser light scattering or atomic force microscopy, or electron microscopy.

2) Ratio of K6CL22 Peptide/Nucleic Acid.

A transfection complex according to the invention may have a ratio of the number of peptide/the number of nucleic acid molecules in a particle that is within the range of 10/1 to 1,000,000/1. This ratio will depend upon the relative sizes of the peptide and nucleic acid molecules, the degree of condensing activity of the peptide, and the degree of condensation that the nucleic acid attains. More particularly, the range will be 200/1 –20,000/1. For example, for K6CL22 in combination with an approximate 8 kb vector, a useful ratio for untargeted delivery of the vector to cells is approximately 2,500:1 (relative numbers of molecules). For licK6CL22 (K6CL22 conjugated to lipid) in combination with an 8 kb vector, a useful ratio for targeted delivery of the vector to cells approximately 2,000:1. Where the nucleic acid is an oligonucleotide of, e.g., 10–50 nucleotides in length, the ratio of peptide/oligonucleotide is in the range of 0.1–10.0 and is preferably 0.5–1.0.

In terms of pg peptide/$\mu$g nucleic acid, it has been determined that the ratio of K6CL22 peptide/nucleic acid which is most useful in transfection is in the range of 1.0 –3.0, with the highest transfection efficiency generally attained in the range of 1.6–2.2.

The ratio of positive/negative charges in a transfection complex containing K6CL22 and a nucleic acid may be within the range 0.2–20 per phosphate residue in the nucleic acid; this ratio more preferably being within the range 0.8–3.0.

3) Chloroquine

Increased transfection efficiency is observed when a transfection complex containing K6CL22 or lipidated K6CL22 is coadministered with chloroquine. The range of concentrations useful according to the invention are generally from 10 um to 1 mM. At the higher dosage, the maximum amount of chloroquine administered with the transfection complex in vivo should not exceed 3.5 mg/kg body weight. For ex vivo applications, the final concentration of chloroquine after dilution from the formulation is in the range of 50 nM–200 $\mu$M, with a preferred range of 1 $\mu$M–100 $\mu$M.

It has also been found that transfection efficiency is increased by extending the time period to which the target cells are exposed to the transfection complex in the presence of chloroquine. This time period may be from 2 hours to as much as 24–48 hours, with the longer incubation times resulting in increased transfection efficiency in the presence of chloroquine.

4) Functional Groups

K6CL22 also may contain one or more attached functional groups, for example, a lipid (licK6CL22). Other functional groups refer to a protein, peptide, lipid, or chemical group that is covalently or non-covalently (e.g., via a coiled coil interaction) linked to K6CL22 or licK6CL22, and which may confer an additional biological function with respect to complex stability in biological fluids, entry into a cell, or delivery of DNA to the cell nucleus, or integration into the chromosome. The covalent linkage may be a stable or labile linkage. Thus, where it is desired to add a functional group to K6CL22 via chemical means, this may be accomplished via addition of the functional group to an internal Serine, Threonine, or Cysteine residue, preferably at a position in the sequence which will be exposed for conjugation to a selected ligand. Cysteine allows specific conjugation via the thiol side chain, to compounds containing other reactive thiol groups (via disulfides), alkylating functions (to form thioether bonds), or other thiol reactive groups such as maleimide derivatives. Bonds of "defined stability" are described hereinbelow, and include bonds such as acid labile bonds (hydrazone) or linkages that are less stable in the reducing environment of the cytosol (disulfide). Such bonds are useful for carrying functional groups on the transfection complex. Where the functional group is a peptide, the covalent linkage may be a peptide bond, thus creating a fusion protein.

Examples of functional groups useful according to the invention include but are not limited to the following: a) a ligand, such as i) an antigenic peptide, or ii) a targeting molecule having a cognate receptor on the surface of a target cell; b) a lipid; c) a neutral hydrophilic polymer; d) an endosomal disruption agent; e) an enzyme; and f) an agent which promotes intracellular trafficking into the nucleus, and combinations thereof.

As used herein, the term "lipid" refers to a four—thirty carbon molecule that is insoluble in water and soluble in alcohol. The term includes fats, fatty oils, essential oils, waxes, sterols, cholesterols, phospliolipids, glycolipids, sulfolipids, aminolipids, chromolipids, and fatty acid. K6CL22 can be specifically modified by condensation with a lipid, for example, an activated ester of a fatty acid. The fatty acid is ideally either palmitic acid, oleic acid, such as dioleoylphosphatidylethanolamine, myristic acid, or cholesterol, although other fatty acids, such as stearic acid, may also be employed.

A functional group useful according to the invention also includes a ligand which serves to promote cellular uptake, e.g., by disrupting membrane structure, such as the HA peptide from the influenza virus. Additional fusogenic-peptides useful according to the invention include the fusogenic-peptide from Sendai Virus (D. Rapaport and Y. Shai, J. Biol. Chem. 1994,263,15124–15131), the fusogenic peptide sequence from HIV gp41 protein (M. Rafalaski, J. D. Lear and W. F. DeGrado, Biochemistry 1990,29, 7917–7922), the fusogenic peptide sequence from Paradaxin (D. Rapaport, G. R. Hague, Y. Pouny and Y. Shai, Biochemistry 1993,32,3291–3297), and the fusogenic peptide sequence from Melittin: (C. R. Dawson et al., Biochem. Biophys. Acta: 1978,510,75).

The DNA and complex solutions were made as follows: DNA solution: 100 µg/ml pCMVβ, 25 mM phosphate pH 7.4, 0.6 M NaCl. Complex solution: 100 µg/m PCMVβ, 25 mM phosphate pH 7.4, 0.6 M NaCl, 200 ug/ml K6Cl22. These solutions were incubated at room temperature for 1 hour and then 4° C. overnight. COS cells were seeded at 1×10$^5$ cells per well in 6 well plates (in DMEM, 10% Fetal calf serum (FCS)) 24 hours before incubation with complex or DNA.

Transfection of Cells

As described below, cells are transfected with a complex comprising K6CL22 and a nucleic acid, and the nucleic acid or its gene product is detected in the cell.

Transfection Protocol 1

Figures 7A, 7B:
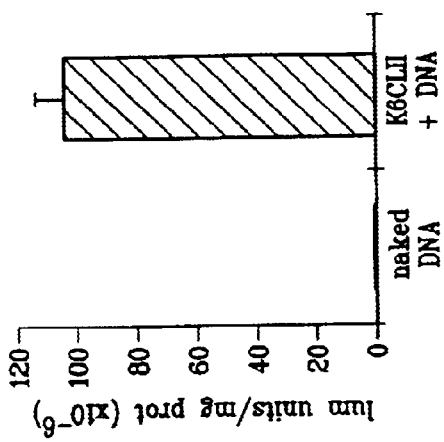
FIG. 7A presents data for triplicate transfections of COS cells with naked DNA or K6Cl22 and DNA complexes. The values provided are: luminescence units read from a luminometer (lum units); the amount of protein found in the sample (mg); luminescence units per mg protein (lum/mg); average luminescence units per mg of protein for each condition (Av); standard error (St. Error).
FIG. 7B is a bar graph of the data presented in FIG. 7A.

The DNA and complex solutions were diluted into PEG diluent (10% PEG 8000, 25 mM phosphate pH 7.4, 37.5 mM NaCl) to a final DNA concentration of 20 µg/ml. Just prior to transfection the COS cells were washed with PBS and 875 µl RATQ medium (RAT medium with 137.14 µM chloroquine) was added per well. 125 µl of diluted complex or DNA solution was then added per well and the cells were incubated at 37° C. for 5 hours. The cells were then assayed for β-galactosidase activity using the Tropix Galacto-Light™ kit (Tropix, catalogue no. BL300G) according to the manufacturer's instructions. Briefly, the wells were washed with DMEM, 10% FCS, and then 250 µl of lysis buffer (provided by the kit, with dithiothreitol added to 1 mM) was added per well. The cells were then scraped off and were pipetted up and down to aid cell lysis. The lysed cells were transferred to an eppendorf tube and centrifuged at 13K for 2 mins. The supernatant was transferred to a clean eppendorf tube. 2–10 µl of the supernatant was added to a luminometer assay tube and was made up to 10 µl with lysis buffer. 100 µl of Reaction buffer is added to each tube, the samples are incubated at room temperature for 60 mins and then analyzed using Light Emission Accelerator and a Barthoid lumat LIB 9501 luminometer. The protein concentration of the cleared cell lysate was measured using the Bio-Rad DC protein assay kit (Bio-Rad). The results are then expressed as relative light units per mg of protein (FIG. 7). Each transfection was carried out in triplicate.

Clearly, there is no transfection of the COS cells with naked DNA, but there is very efficient transfection with K6Cl22/DNA complex. Since it is known in the art that cationic peptide/DNA complexes are taken up into cells through the endocytic pathway (Wagner, E., Curiel, D. and Cotten, Matt (1994) Advanced Drug Delivery Reviews 14: 113–135) the epitope containing K6Cl22 peptide must be delivered to the endosomes of the transfected cells. The endosome is the compartment of the APC delivery to which results in Class II antigen presentation.

Transfection Protocol 2

1. Trypsinise cells to harvest and seed into 6-well plates, 1×10$^5$ cells/well in 3 ml. Allow triplicate wells per point (usually Mock, positive control and 12 samples) and two sets of plates per experiment. Incubate at 37° C. overnight to establish.

2. Next day aspirate medium from wells and carefully wash with SF RPMI (1×).

3. Add 875 µl RAQ (or RA where the experiment is done in the absence of chloroquine) per well. Then add 125 µl complex (or SF RPMI) dropwise, using a gilson. Gently swirl plates to ensure mixing. Incubate at 37° C. for 5 hours.

4. After incubation, aspirate the transfection media from the wells and replace with 3 ml fresh DF10 per well. Incubate overnight.

5. Assess transfection efficiency the following day by (a) Galacto-light and X-gal staining for CMVβ plasmid or (b) Immunostaining and ELISA for ntr-containing plasmids. (CMVβ was bought from Clontech Laboratories, Inc. Catalogue Number 6177-1. Originally made by MacGregor & Caskey, Nucl. Acids Res. vol 17 p2365 (1989).)

RAQ Medium

Add 11.36 ml human serum album to 500 ml RPMI. Store this (RA) at 4° C. Prior to setting up transfections, dispense the required volume of RA (0.875 ml×no. of wells) into a sterile container and add 13.7 µl of 10 mM chloroquine (Q) per ml. This leads to a final concentration of 120 µM chloroquine in the transfection media after the addition of complex.

Mocks

Mock wells are essentially negative controls, i.e., not transfected. Add 125 µl SF RPMI to the RAQ (step 3 above) instead of complex.

Positive control

Stock DNA is kept at concentrations of around 0.5 mg/ml; higher concentrations should be diluted down to this with $H_2O$ and the exact concentration determined.

PEG diluent (see below):

log PEG 8000

5 ml 0.5M PO$_4$—pH7.4

750 μl 5M NaCl

Make up to 100 ml with dH$_2$O and filter through 0.2 mM filter to sterilize Make up 'positive control' complex as follows;

a) Add the following in descending order to a well a 'v'-bottomed 96-well plate:

15 mg/ml NBC9

2.4 μl (2 μg/μg peptide/DNA dH$_2$O*

103.8 μl 0.5M PO$_4$ 9.0 μl

5M NaCl 21.6 μl

DNA*

36.0 μl 1 mg/ml LIP9

7.2 μl (0.4 μg/μg peptide/DNA (180 μl final)

*amounts are given for a 0.5 mg/ml DNA solution. For other stock DNA concentrations adjust amounts accordingly. A final concentration of 100 μg/ml is required.

b) Cover plate with a plate sealer plus lid (to minimise evaporation) and incubate for 1 hour at RT, followed by overnight in the fridge.

c) Just prior to transfection, add 660 μl of PEG diluent to a well of a 24-well plate and put plate on shaker in hood. Set to shake at 500–600. Remove 165 μl of complex from 96-well plate and add dropwise to PEG whilst shaking.

d) Add 125 μl diluted complex to RAQ in wells (use within 1 hour of dilution).

Samples are at 20 μg/ml DNA. Add 125 μl per well.

X-gal Staining (CMVβ-Transfected Cells)

Protocol 3

1. Remove supernatant and wash cells with PBS (approx. 2 mls/well).
2. Fix cells with 1 ml/well of 0.05% gluteraldehyde. Incubate at RT for 10 mins.
3. Wash cells with PBS.
4. Stain cells with 1 ml/well of X-gal solution. Incubate plate overnight at 37° C.
5. Next day look for presence of blue cells. Blue stained cells indicate that the gene has been successfully delivered to the cells. Gluteraldehyde Stock gluteraldehyde at 25% is obtained from SIGMA and kept frozen in aliquots. Dilute to 0.05% with PBS (I in 500 dilution).

X-gal Solution

X-gal stock:

40 mg/ml in Dimethyl formamide.

X-gal buffer:

20 mM K$_3$Fe(CN)$_6$ Potassium Ferricyanide (0.66 g/100 mls)

20 mM K$_4$Fe(CN). 3H$_2$0 Potassium Ferrocyanide (0.84 g/100 mls) 2 mM MgCl$_2$ in PBS.

Dilute X-gal stock in X-gal buffer by a factor of 1 in 40 to give a 1 mg/ml solution.

Galacto-Light Assay (CMVβ-Transfected Cells)

Protocol 4

1. Wash cells 1× with PBS.
2. To prepare cell extracts, add 250 μl lysis buffer/well of the 6-well plate. Scrape off cells and pipette up and down to aid cell lysis.
3. Transfer to eppendorf. Centrifuge a 13K rpm for 2 mins.
4. Transfer supernatants to clean eppendorfs.
5. For each supernatant, transfer 10 μl to an illuminometer tube.
6. Prepare positive and negative controls.
7. Add 100 μl of Reaction buffer (with repeat pipette) to each illuminometer tube. Shake to mix. Incubate at room temperature for 60 mins.
8. Prepare illuminometer by washing through with Light Emission Accelerator, three times, by selecting 'others', 'operator function', 'wash cycle', 'start' (2×). Exit out of wash cycle.
9. Run samples by selecting 'measure', 'raw data', 'continue', 10s (enter), 1 replicate (enter). Setting the illuminometer time for 10 seconds per point will allow the injection of 100 μl Light Emission Accelerator per tube. Remember to check level of Light Emission Accelerator at regular intervals.
10. If readings are too high dilute samples with Galacto-Light Buffer Diluent (10 μl sample in 90 μl buffer) and re-read.
11. Wash illuminometer though with dH$_2$O after use (exit 'measure' program and re-enter wash cycle as indicated in step 7).

Lysis Buffer

Add fresh 100 mM stock DTT (Dithiothreitol) to kit lysis solution to 1 mM (1%).

Reaction Buffer

Warm Galacton Substrate and Galacto-Light Buffer Diluent to room temperature. Dilute Galacton Substrate 100-fold with Galacto-Light Buffer Diluent just prior to use.

Positive Control

Add 1 μl of β-galactosidase (10 units/ml, see Galacto-Light protocol for details) to 9 μl mock transfected cell extract.

Negative Control

Assay a volume of cell extract equivalent to the volume of experimental cell extract used (i.e mocks).

To Demonstrate That DC Can be Transfected With Complexes That Contain Antigen.

Complexes are made which are similar to those described in the previous example. These complexes may contain DNA encoding a reporter gene (e.g. luciferase) which is condensed by a peptide/protein which contains an antigenic sequence and a DNA-binding sequence, such as K6C122. The complexes may also include other DNA condensing peptides or other lipidated peptides as described in International Patent Application No. PCT/GB96/01396. Such complexes have been shown to transfect COS cells (see above) and experimental optimisation of the complexes will result in transfection of DC. Optimization can be done by empirically testing slightly different complexes for their ability to transfect DC. The transfection efficiency can be assessed by methods such as visualising green fluorescent protein (GFP)

expressing cells using a fluorescence microscope or measuring luciferase or β-galactosiciase activity. Methodologies for measuring these reporter proteins are described herein.

To Demonstrate That Antigen Which is Incubated With Cells When Complexed Into a Delivery Vehicle is More Readily Cell Associated Than Free Antigen.

The antigen used in these experiments is a peptide that contains an epitope sequence from influenza A nucleoprotein (K6CL22), as above. The peptide was fluorescently labeled through the cysteine using Fluorescein-maleimide. The labeling was approximately 7% efficient. The protocol for the labelling was as follows: 4.2 mg K6CL22 was dissolved in 0.5 ml 20 mM MES, pH 6.5. Next, 2.1 mg fluorescein-5-maleimide (Molecular Probes, Europe) was dissolved in 250 ul ethanol and added to the peptide solution. Ethanol was added dropwise until the agitated solution cleared. After 1 h at 24° C. the sample was desalted an a PD-10 column (Pierce & Warriner, UK) using 50% aqueous acetonitrile. The fractions containing labelled peptide were lyophilised and stored at −20° C. This peptide will be termed K6Cl22-F1.

Figure 6:
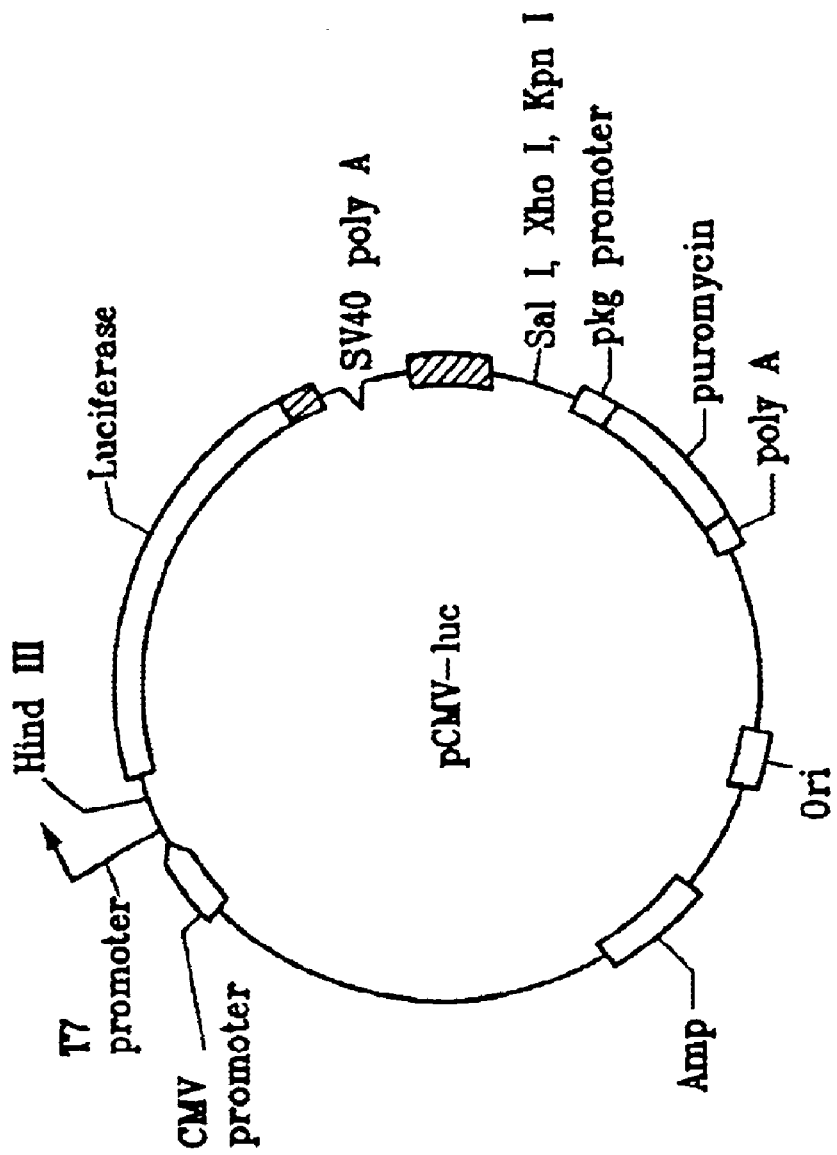
FIG. 6 is a schematic illustration of the plasmid pCMVluc, a luciferase expression vector which has the luciferase gene driven from the CMV immediate early promoter. The plasmid includes the luciferase gene, which contains an SV40 intron and polyA sequence, a bacterial origin of replication and the betalactamase gene for selection in bacteria. The plasmid also includes the puromycin gene for selection in eukaryotic cells.

A non-viral delivery system was made using K6Cl22-F1 and pCMVIuc (FIG. 6). The delivery vehicle was made in the following way. Two separate solutions were made up peptide and DNA Peptide solution: 19.2 ml of K6Cl22-F (5 mg/ml in sterile water) was added to 1180.8 ml of 10 mM HEPES, 150 mM NaCl (HES). DNA solution: 56.5 ml of pCMVIuc (0.5 mg/ml) was added to 1143.5 ml of HBS.

The peptide solution was then flash mixed with the DNA solution by adding quickly by pipette followed by repeated pipetting. The complex solution was left at room temperature for 1–2 hours before adding to the cells.

A control peptide solution contained 19.2 m! of K6Cl22-F1 (5 mg/ml) was added to 2380.8 ml of 10 mM HEPES, 150 mM NaCl (HBS).

COS cells were seeded at $1\times10^5$ cells per well in 6 well plates 24 hours before incubation with complex, peptide or buffer. The COS cells were washed once with PBS and 800 ml RAT medium was added. 200 ml of complex, free peptide or HES were then added to the cells. After an incubation of 30 mins the cells were washed twice with PBS and then incubated with 2 ml PBS, 1 mM EDTA to release the adhered cells. The cells were harvested, resuspended in 500 ml PBS and analysed by FACS analysis (Beckton Dickinson FACScan). The FACS data clearly show that the cells to which complex has been delivered are associated with more fluorescence and therefore more peptide (i.e. antigen) than those incubated with peptide alone (FIG. 5).

To Demonstrate That DC Transfected With Antigen Expressing Constructs Can Stimulate Autologous T Cells.

It has previously been shown that transfected DC are capable of stimulating the relevant T cell clones (Alijagic et al. Eur. J. Immunol. 1995 25:3100–3107).

Human PBMC were prepared from Buffy coats by methods known in the art (Current Protocols in Immunology, ed. J. E. Coligan et al). The PBMCs are split into two portions, from one T cells were purified by standard non-T cell depletion (magnetic beads) technologies known in the art (Current Protocols in Immunology, ed. J. E. Coligan et al) and from the other portion DC were derived as described above.

The DC were then transfected with plasmid encoding influenza A nucleoprotein protein by similar complexes to those described above. The complexes require optimisation to increase transfection efficiency; as described in PCT/GB96/01396. The transfected DC were then incubated with the autologous T cells at various ratios and the proliferative response of the T cells was measured by $^3$H-thymidine incorporation by methodolgy known to those familiar with the art (Current. Protocols in Immunology, ed. J. E. Coligan et al). In the presence of transfected DC the T cell proliferation is expected to be substantially greater than when incubated with untransfected DC.

There are a number of methods by which presentation of influenza nucleoprotein (NP) can be analysed to assess whether it is Class I or II restricted. The ability of the DC to stimulate CD4+ or CD8+ subsets of the T cell population can be measured. Transfected DC are incubated at different DC:T cell ratios with either autologous CD4+ or CD8+ T cells. The relative proliferation of the T cells then allows assessment of whether the antigen (NP) is being presented in a Class I or Class II restricted manner. Stimulation of CD4+ cells signifies Class II presentation while stimulation of CD8+ cells signifies Class I presentation.

After transfection of the DC with an NP expressing plasmid the DC will be capable of stimulating CD8+ cells to proliferate to a greater extent than CD4+ cells and thus antigen presentation was mainly MHC Class I restricted. Class I or II restriction of antigen presentation can also be measured by analysis of the cytokines produced when transfected DC are incubated with autologous T cells. Transfected DC and autologous T cells are incubated together at different ratios (usually in the range of 1:1 to 1:100 of DC:T cell).

To Demonstrate That Antigen Delivered to DC is Presented to Autologous T Cells and That Presentation is Principally via MHC Class II Presentation.

Antigen can be delivered to DC by inclusion of the antigen in the delivery vehicle. There are a number of methods by which antigen may be included in the delivery system. The antigen may be conjugated, by conjugation chemistry, to DNA-binding peptides. The conjugation chemistries may include, but are not restricted to, those described in International Patent Application No. PCT/GB96/01396. The antigen may be an epitope which, together with a DNA-binding sequence, can be synthesised by standard peptide chemistry techniques. The antigen may also be a recombinant molecule which is designed to contain the antigen and a single, or multiple, DNA-binding sequences. In the above cases the antigen is bound to the complex by ionic interaction between the DNA-binding function and the phosphate backbone of the DNA. The antigen-DNA-binding sequence conjugate-may or may not be the only DNA condensing agent in the delivery vehicle. The antigen may also be bound to the delivery vehicle by hydrophobic, electrostatic, covalent, or other interactions. The antigen may be any protein, or part thereof, to which an immune response can be generated.

Delivery vehicles that contain antigen may be tested for their efficiency of delivery of antigen to DC by testing, as follows. Test complexes are made and tested for their ability to deliver antigen to DC by measuring presentation of the antigen by the DC to which antigen has been delivered. Methods to measure the presentation of the antigen are described below. Methods by which the delivery may be optimized for better nucleic acid/antigen delivery are described in International Patent Application No. PCT/GB96/01396.

Using the complex it can then be shown that DC that have been incubated with antigen containing delivery vehicle are able to present the antigen to T cells, The antigen used in these experiments must be a 'Recall antigen'. A Recall antigen is an antigen to which the donor from whom the DC and T cells were purified has already generated an immune response. Examples of recall antigens are tetanus toxoid and influenza nucleoprotein (in donors who have previously been infected with influenza). Presentation of the recall antigen can be assessed by incubation of DC with autologous T cells and measurement of the proliferation of the T cells by measuring $^3$H-thymidine incorporation. The DC and T cells are incubated at various ratios (usually 1:1 to 1:100 DC:T cells). To test whether the antigen is presented by Class I or Class II MHC molecules one of a number of assays can be carried out. These include, but are not restricted to, measurement of the ability of the DC to stimulate CD4+ or CD8+ subsets of the T cell population or measurement of cytokine production when DC are incubated with autologous T cells. To measure of the ability of the DC to stimulate CD4+ or CD8+ subsets of the T cell population transfected DC are incubated at different DC:T cell ratios with either autologous CD4+ or CD8+ T cells. The relative proliferation of the T cells then allows assessment of whether the antigen is being presented in a Class I or Class II restricted manner. Stimulation of CD4+ cells signifies Class II presentation while stimulation of CD8+ cells signifies Class I presentation.

Similar assays are set up to measure cytokine production. DC are incubated with autologous T cells and after a given time point, usually but not always 24 hrs samples of the medium are taken and assayed for cytokines. Examples of cytokines which are commonly measured are IFN-gamma (signifies a Th1 response) or IL-4 (signifies Th2 response). Commercial kits are available to measure the levels of these cytokines (R&D Systems). Cytokine production can also be measured by more sensitive assays based on the ELISPOT technique (Current Protocols in Immunology, ed. J. E. Coligan et al).

To Demonstrate That Delivery of Antigen and DNA to DC Generates a Stronger Proliferative Response From Autologous T Cells Than Delivery of Antigen or DNA Alone Delivery of antigen alone or DNA alone to DC generally leads to presentation of epitopes of the antigen, in association with MHC molecules, on the surface of the DC. Delivery of antigen tends to lead to presentation in association with MHC Class II molecules, whereas delivery of DNA (i.e. transfection of the DC) generally leads to presentation in association with Class I molecules. Delivery of both DNA and antigen leads to increased presentation by the DC compared to delivering either DNA or antigen alone.

Delivery vehicles that contain antigen and DNA may be tested for optimal delivery to a target APC cell as follows. Test delivery vehicles are made and tested for their ability to deliver antigen and DNA to DC by measuring presentation of the antigen by the DC to which antigen has been delivered. Methods to measure the presentation of the antigen are described in the two previous examples. Methods by which the complex may be optimized for better delivery are described in International Patent Application No. PCT/GB96/01396.

DC to which both DNA and antigen are delivered are expected to show increased ability to stimulate proliferation of autologous T cells (measured by $^3$H-thymidine incorporation) compared to DC to which only DNA or protein/peptide antigen has been delivered. Thus, delivery of both DNA and peptide/protein antigen is expected to show significant advantage for the generation of an immune response compared with delivery of either separately.

The invention also encompasses the co-administration of two separate moieties, (i) nucleic acid and (ii)peptide antigen, as a mixture. It is believed that such co-administration will result in an increased ability of the APC to stimulate proliferation of autologous T cells compared to APC to which only DNA or protein/peptide antigen has been delivered.

Addition of Secretion Signal to Antigen Gene

To demonstrate that transfection with a delivery vehicle containing DNA encoding an antigen gene with a secretion signal sequence that is functional in mammalian cells gives rise to a greater Class II response than transfection with a delivery vehicle in which an non-secreted version of the antigen is produced, in vitro derived dendritic cells (from donors previously infected with influenza A) are transfected with a delivery vehicle containing a DNA molecule encoding the influenza nucleoprotein gene with or without a secretory signal sequence. Syngeneic T cells are then assayed for class I- and class II-restricted responses when incubated with the transfected DCs (prepared from the same PBMC sample as the transfected DCs). Dendritic cells transfected with the secreted form of NP show increased Class II-restricted T cell activation ability when compared to DCs transferred with the gene encoding the non-secreted antigen. Thus, addition of secretory signal sequence to the antigenic gene produces an increased class II-restricted response.

Comparative Demonstration That a Complex or Mixture According to the Invention, Containing an Epitope and a Nucleic Acid, Induces a Stronger Immune Response Than a Free Epitope.

To demonstrate that delivery of an epitope or antigen as part of a delivery complex is more effective in inducing inmunogenicity than delivery of 'free' antigen (that is, an epitope or antigen such as a peptide or polypeptide that is free of nucleic acid), mice are vaccinated with a mixture or complex according to the invention, i.e., nucleic acid and a peptide antigen, or with the same peptide antigen free of nucleic acid. The immune responses in the vaccinated mice are measured by standard immunological assays which are well known to those skilled in the art, such assays are $Cr^{51}$ release assays, T cell proliferation assays and cytokine assays (Current Protocols in Immunology, ed. J. E. Coligan et al), as described herein. For example, a comparative demonstration may be performed using an antigen which consists of an epitope of an antigenic protein known to be presented by the mouse strain being immunized, such as a peptide epitope of influenza nucleoprotein, or it can be a whole protein, such as the influenza nucleoprotein. The mice are vaccinated by subcutaneous, intravenous, intraperitoneal or other routes. The mice may be subject to boosting injections at periods of 1 to 4 weeks after the priming injections. The mice are sacrificed at least 3 weeks after the priming or boosting injection, their splenocytes are harvested and subject to standard immunological assays to determine the level of the immune response. A complex or mixture according to the invention is determined to elicit a more effective immune response where the proliferative response to the test antigen of splenocytes from mice immunized with a complex or mixture according to the invention is at least two-fold and preferably five- to ten-fold greater in magnitude than the proliferative response of splenocytes from animals immunized with antigen alone.

Once the magnitude of the immune response is determined to be at least two-fold greater in a comparative assay, the type of immune response generated is further defined using $Cr^{51}$ release assays and cytokine assays. Complexes or mixtures according to the invention will preferably elicit both a cellular and a humoral immune response, at least one of which is two-fold or greater in magnitude than a control or prior art vaccine in a comparative assay. Alternatively, the inventive complexes or mixtures will elicit either a cellular or a humoral immune response, that response of which is at least two-fold and preferably five- to ten-fold greater in magnitude than a control vaccine in a comparative assay. A cellular immune response is indicated by a cytotoxic T cell response, as measured by $Cr^{51}$ release assays, and is indicative of a class I restricted response. Measurement of this response in the presence of anti-murine CD4 versus anti-murine CD8 antibodies may provide a more accurate indication of the MHC restriction of the response, and whether the immune response also involves a humoral immune response. That is, a response in the presence of anti-CD8 antibodies is Class II restricted whereas a response in the presence of anti-CD4 antibodies is Class I restricted. Anti-CD4 or anti-CD8 antibodies also may be used in the proliferation assays to indicate whether the immune response is MHC class I or MHC class II restricted.

EXAMPLE 1

Transfection of Human Dendritic Cells With K6CL22/DNA

Generation of Human Dendritic Cells (DC)

Figure 8:
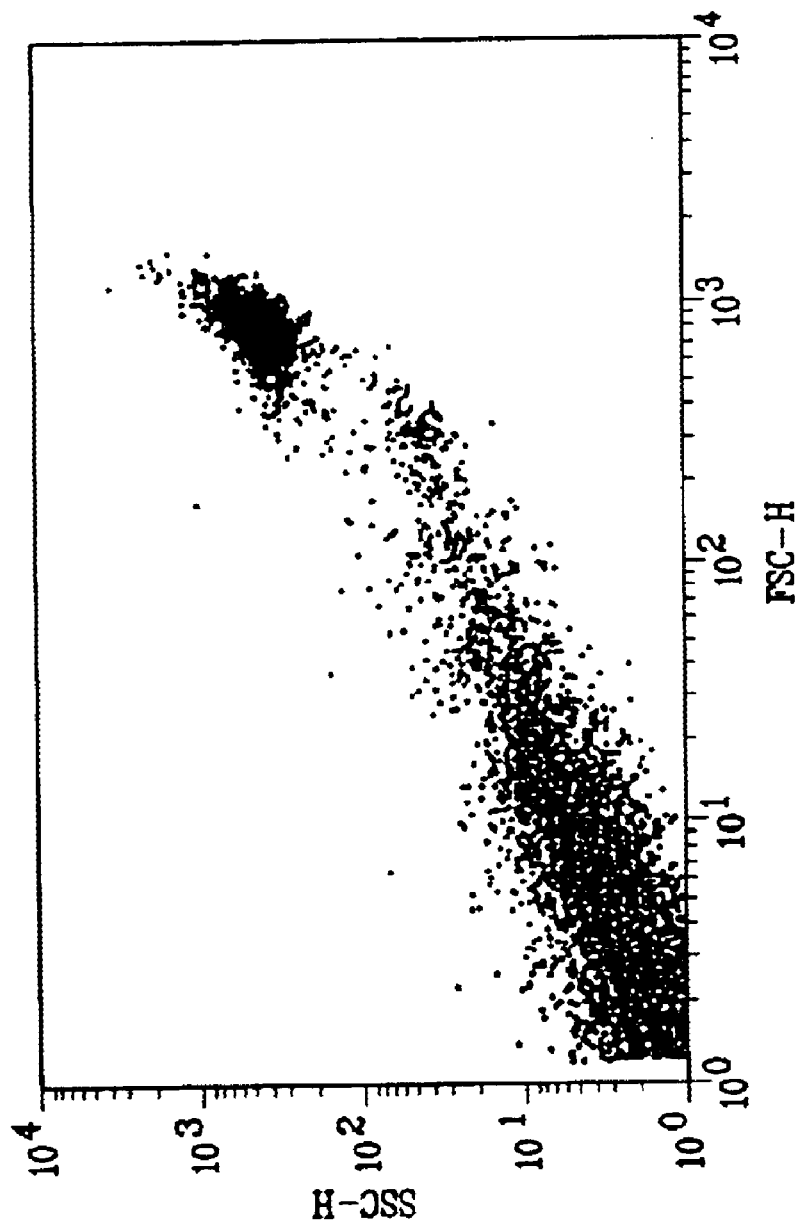
FIG. 8 shows a population of cells which is relatively homogeneous as analyzed by forward and side scatter on a FACscan.
Figure 9:
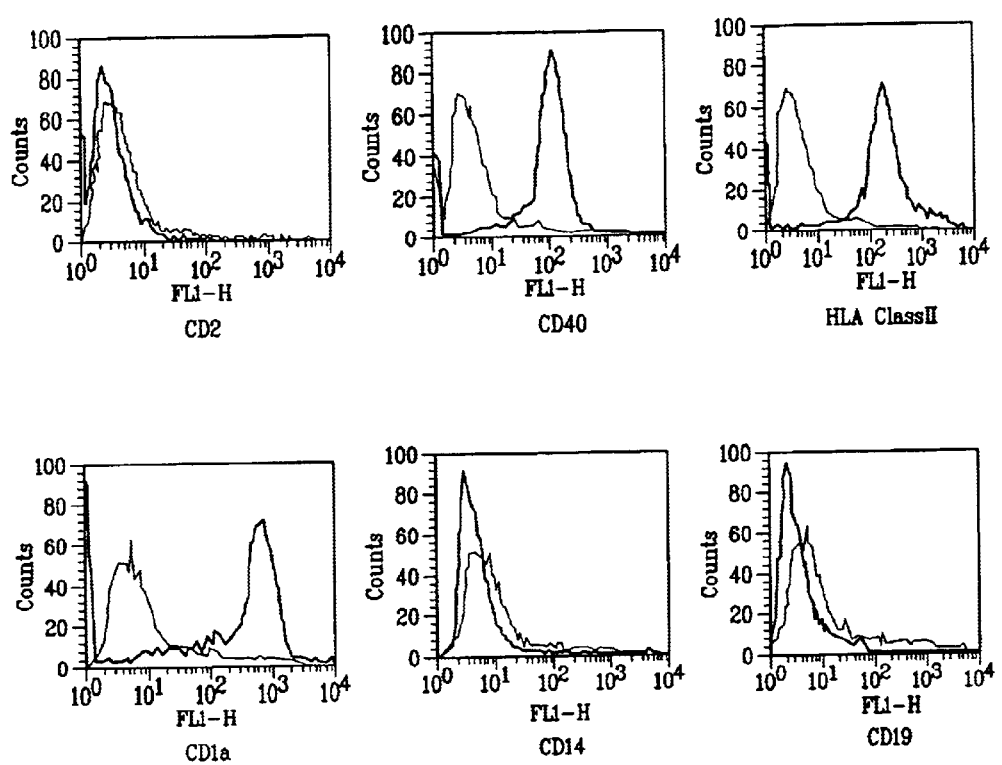
FIG. 9, dendritic cells were analyzed for surface markers using FITC or PE labeled antibodies specific for those markers and a Becton Dickinson FACscan and some isotype negative control antibodies were used.

Human DC were provided as described by Romani et al (J. Exp. Med. 1994, 180:83–93). Briefly, human PBMC were prepared from Buffy coats by standard protocols known in the art. The PBMC were resuspended in DC medium (RPMI-1640, 10% FCS, 2 mM glutamine, 1% non-essential amino acids, 50 μM P-mercaptoethanol, 10 units/ml penicillin, 1 00 g/ml streptomycin) and were allowed to adhere to plastic tissue culture dishes. After 2 hours at 37° C., 5% $CO_2$ the nonadherent cells were removed, the adherent cells were gently washed and subsequently cultured with DC medium plus cytokines (GM-CSF (800 U/ml) and IL-4 (500 U/ml)). The cultures were fed with cytokines every second day of culture. After 6 to 7 days of culture the cells have the 'DC-like' surface markers which are known in the art to identify these cells. The population of cells is relatively homogeneous as analyzed by forward and side scatter on a FACscan (FIG. 8) and the surface markers characteristic of these cells are as expected ($CD14^-$, $CD19^-$, $HLA-DR^+$, $CD1a^+$, $CD40^+$; FIG. 9): In FIG. 9, dendritic cells were analyzed for surface markers using FITC or PE labeled antibodies specific for those markers. A Becton Dickinson FAC scan and some isotype negative control antibodies were used.

Figure 10:
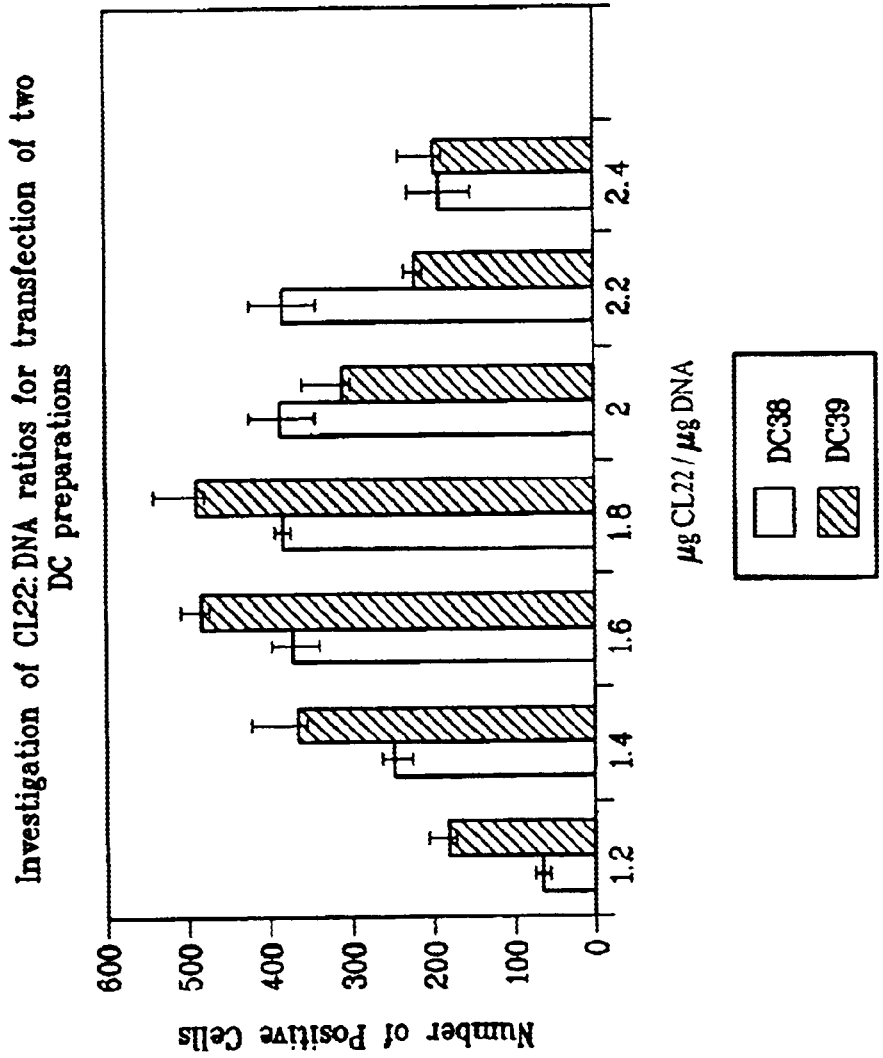
FIG. 10 shows a graph of transfection efficiency wherein the peptide/DNA ratio was varied between 1.2 and 2.6.

FIGS. 10–14 show results of transfections for two different preparations of dendritic cells in which certain variables were tested in order to determine the effect on transfection efficiency. In FIG. 10, the peptide/DNA ratio was varied between 1.2 and 2.6, with the highest transfection efficiency being obtained at ratios in the range of 1.4–2.0. The transfections were performed in 40 μM chloroquine, with a transfection time of 4 hours and an expression time of overnight.

Figure 11:
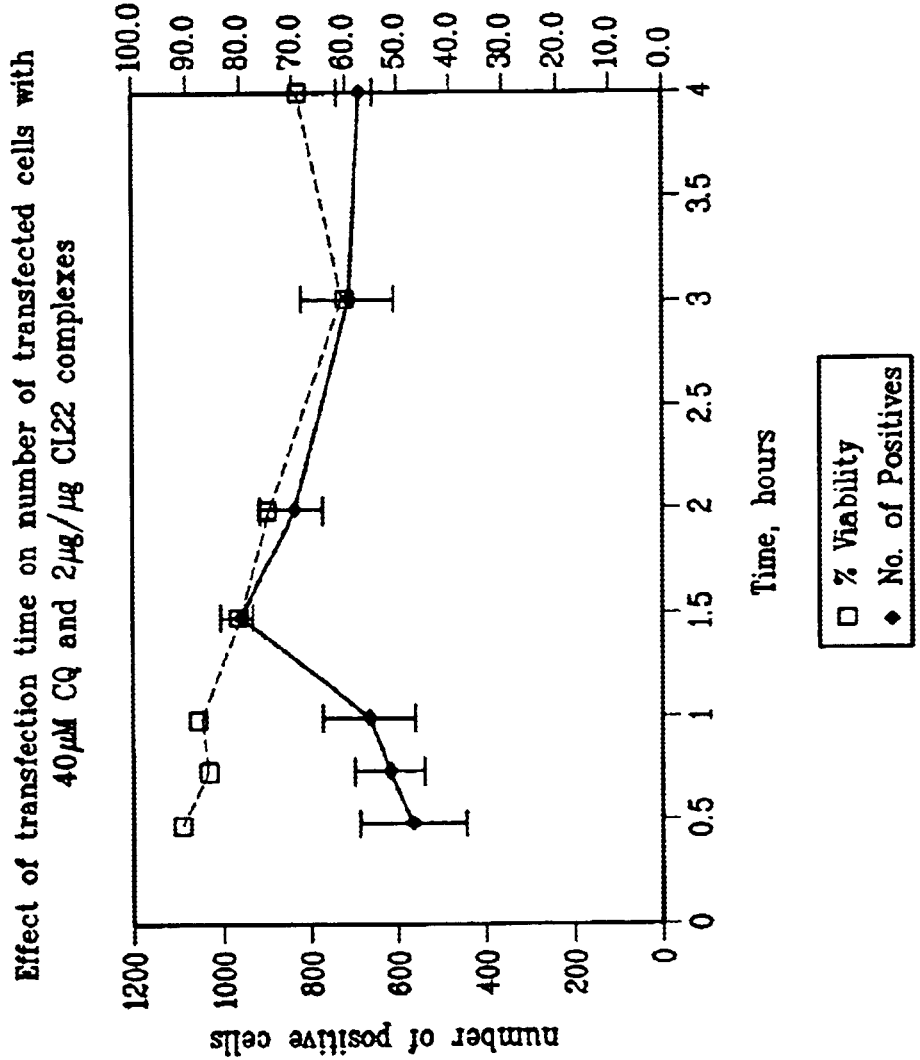
FIG. 11 shows results of transfections of dendritic cells with a variable transfection time.

FIG. 11 shows results of transfections of dendritic cells with a variable transfection time. Dendritic cells were transfected with 2 μg K6CL22/μg DNA for various transfection times, as indicated, in 40 μM chloroquine. The expression time was overnight and the cell viability was also assessed, at the time of harvest, by trypan blue staining.

Figure 12:
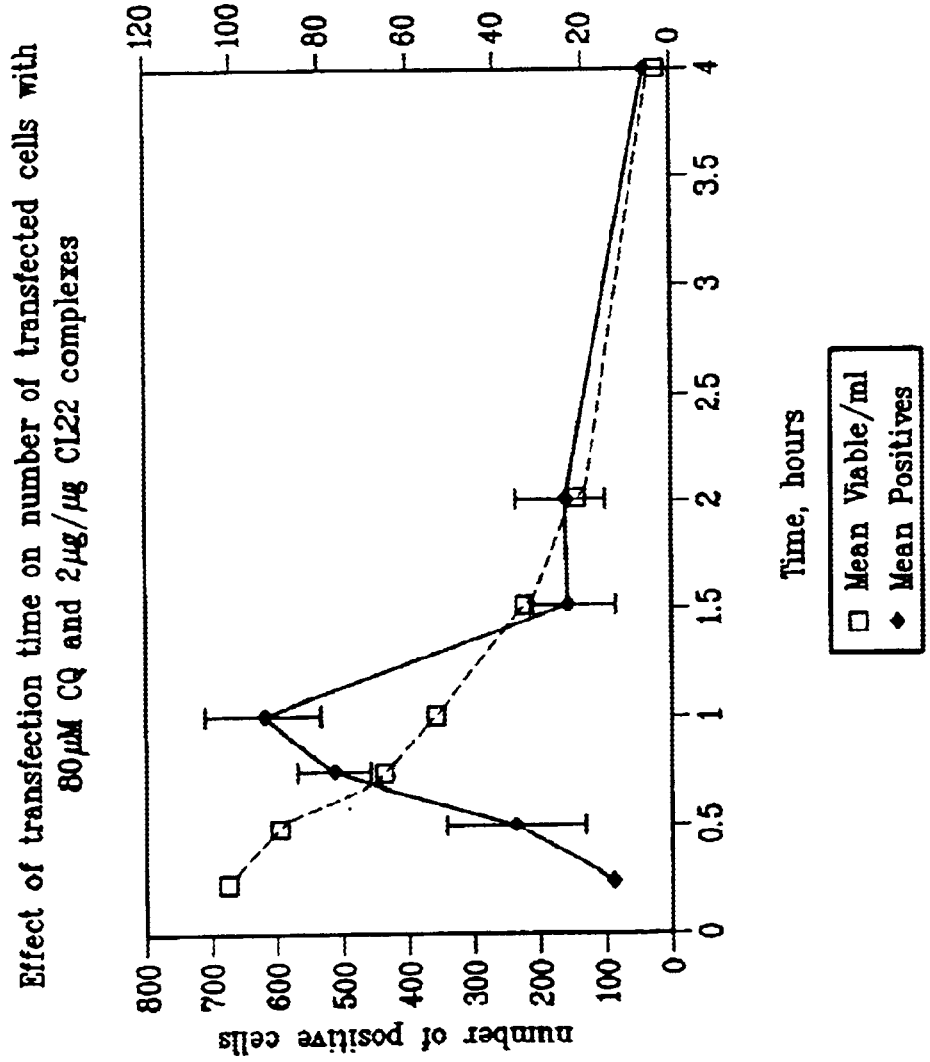
FIG. 12 shows results of transfections of dendritic cells with a variable transfection time.

FIG. 12 shows results of transfections of dendritic cells with a variable transfection time. Dendritic cells were transfected with 2μg K6CL22/μg DNA for various transfection times, as indicated, in 80 μM chloroquine. The expression time was overnight and the cell viability was also assessed, at the time of harvest, by trypan blue staining.

Figure 13:
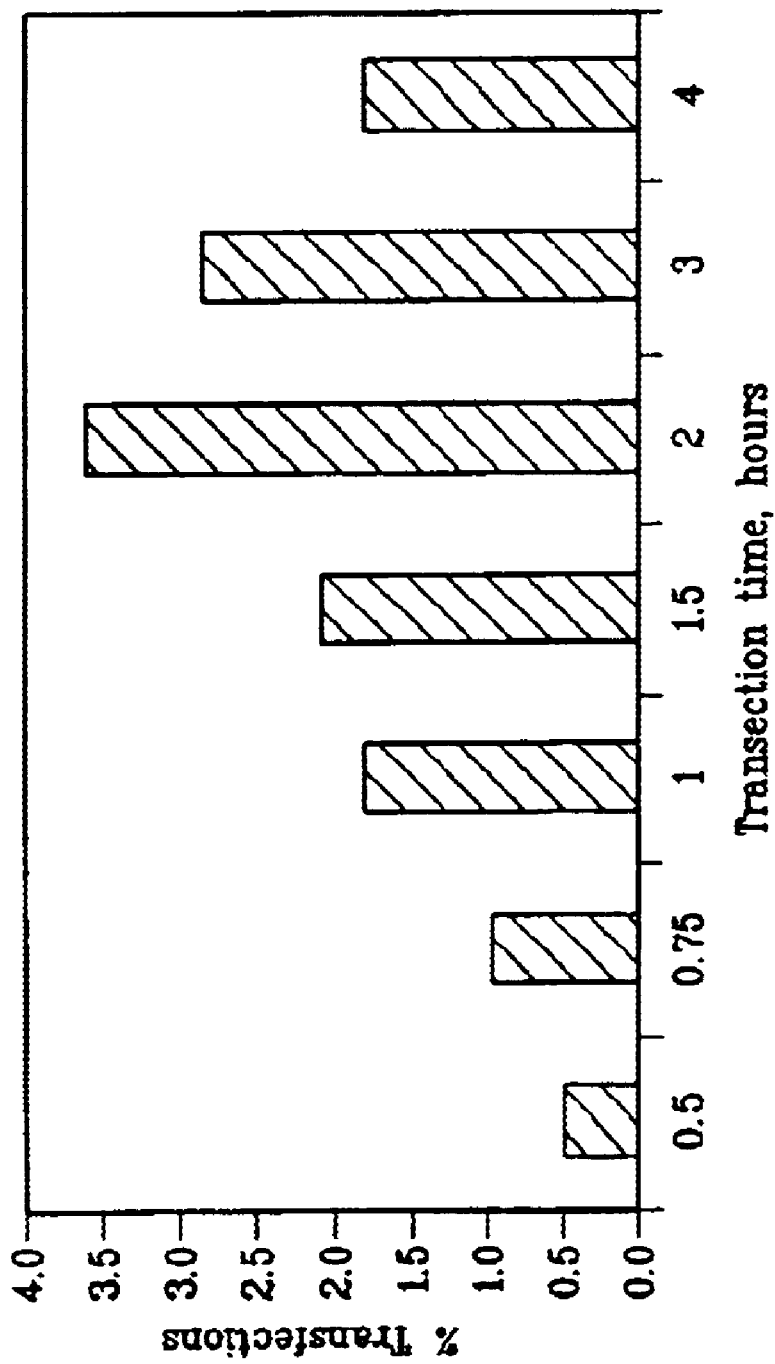
FIG. 13 shows results of transfection efficiency in which the time of transfection is varied.

FIG. 13 shows results of transfection efficiency in which the time of transfection is varied. Transfection of dendritic cells was performed using 2 μgK6CL22/μgDNA in the presence of 40 μM Chloroquine. Transfection efficiency is calculated as (total number of positive cells divided by total number of viable cells)×100. Expression time was overnight.

Figure 14:
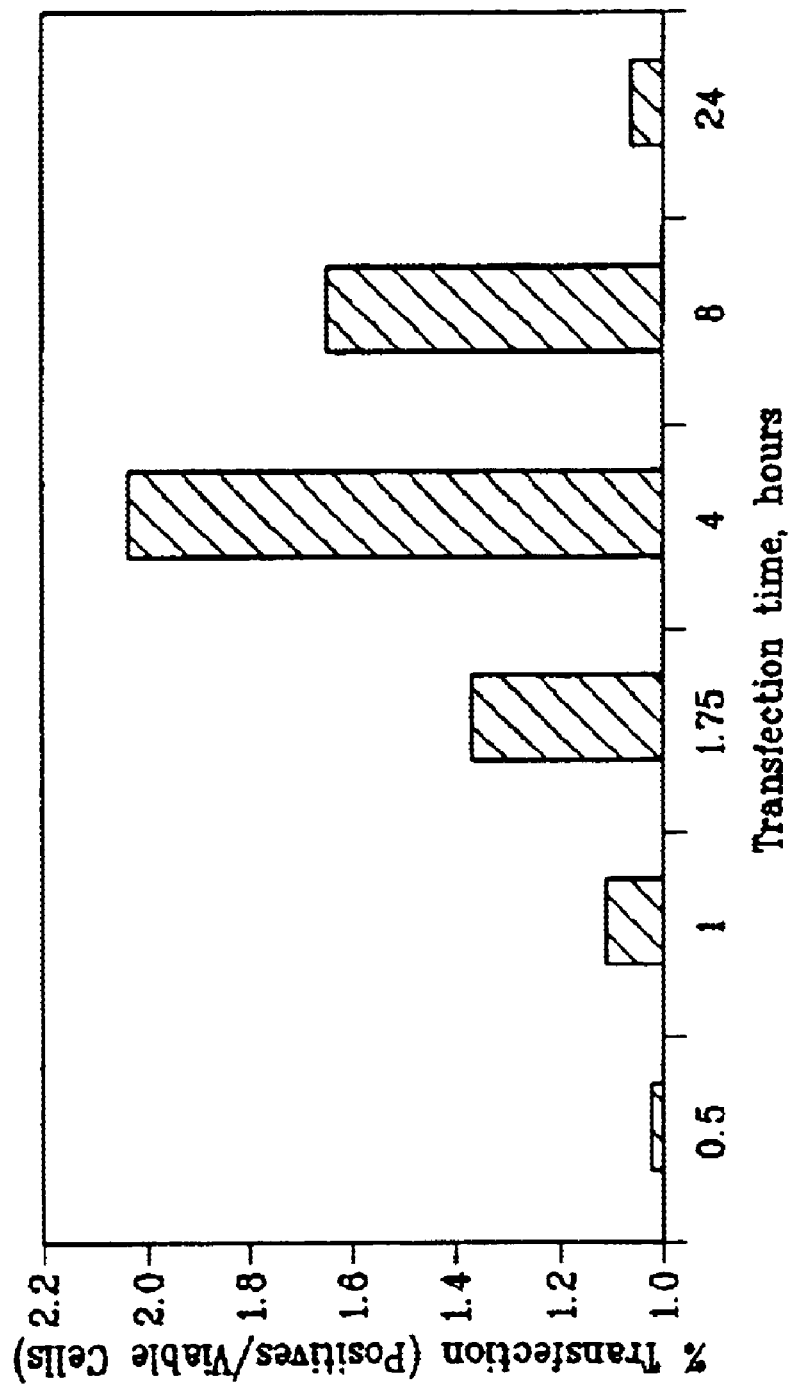
FIG. 14 shows the effect of transfection time on transfection efficiency using 2 µg K6CL22/µg DNA and 20 µM chloroquine.

FIG. 14 shows the effect of transfection time on transfection efficiency using 2 μg K6CL22 μg DNA and 20 μM chloroquine. Transfection efficiency is calculated as (total number of positive cells divided by total number of viable cells)×100. Expression time was overnight.

EXAMPLE 2

Figure 15:
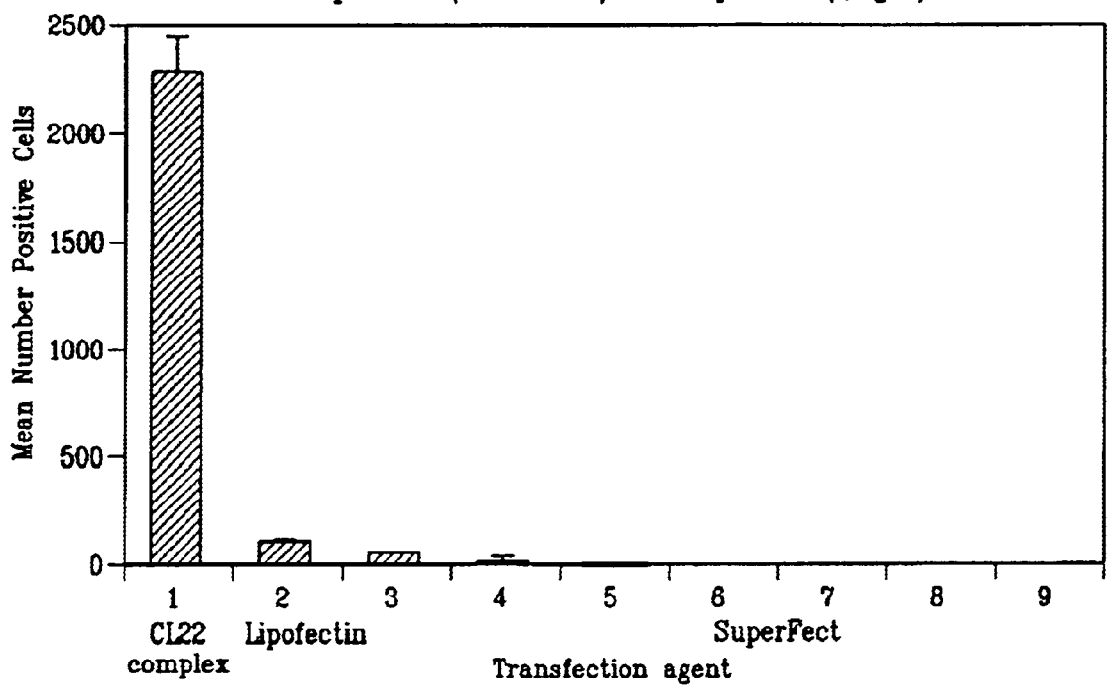
FIG. 15 presents a comparison of K6Cl22 based delivery complexes with Lipofectin (Gibco-BRL) and SuperFect (Qiagen).

Comparison of K6Cl22 Transfection Complex and Lipofectin and Superfect With Respect to Efficiency of Transfection of Dendritic Cells Equal numbers of dendritic cells from the same preparation were transfected with the following agents, all the cells were then cytospun and the number of positive cells counted by visualization using fluorescence microscope. The transfection agents were; 2 μg K6Cl22/μg pEGFP-NI delivery complexes with 80 μM chloroquine and a transfection time of 1 h (1); Lipofectin used at 2.5 μg pEGFP-NI/10 μl Lipofectin (2) and 10 μg pEGFP-NI/20 μl Lipofectin (3); SuperFect used at various amounts of pEGFPNI/SuperFect–1 μg/2 μl (4), 1 g/4 μl (5), 1 μg/8 μl (6), 2.5 μl/5 μl (7), 2.5 μl/10 μl (8) and 2.5 μl/20 μl (9). The transfections with Lipofectin were carried out as described in the product protocol (Gibco, BRL) with a four hour transfection period followed by three fold dilution and an overnight expression period. The transfections with SuperFect were carried out as described in the product protocol (Qiagen) again with an overnight expression period. The results, shown in FIG. 15), are the means of at least triplicate points (except 2 which is the mean of duplicate points) and the error bars are standard errors.

EXAMPLE 3

Transfection of Human Dendritic Cells With CL22 or CL26

Figure 16:
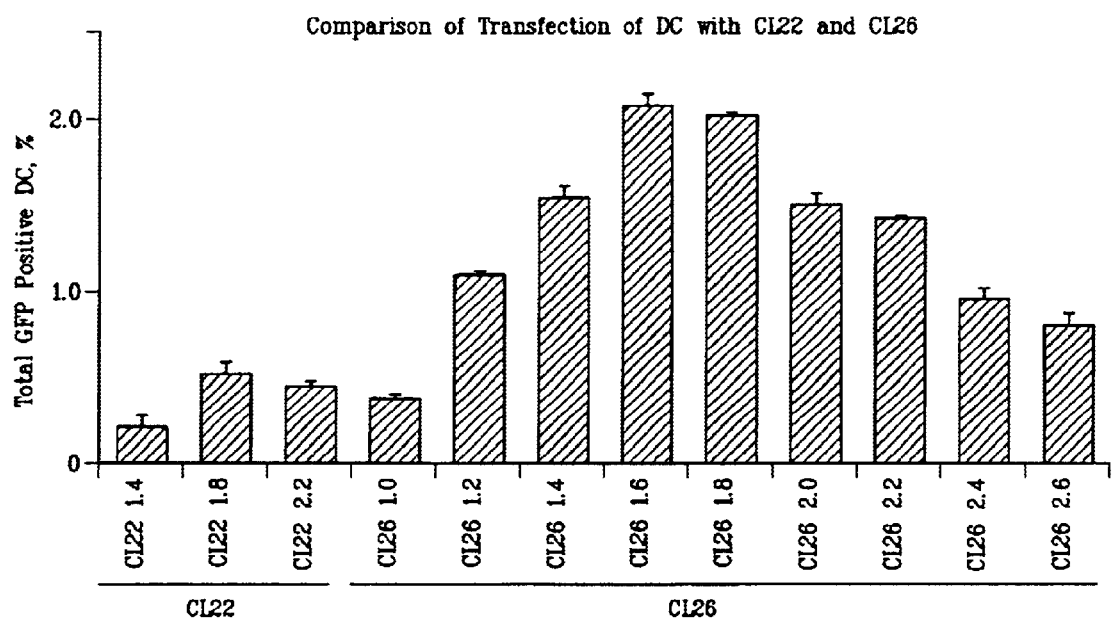
FIG. 16 shows results of transfection of dendritic cells with CL22 and CL26.
Figure 17:
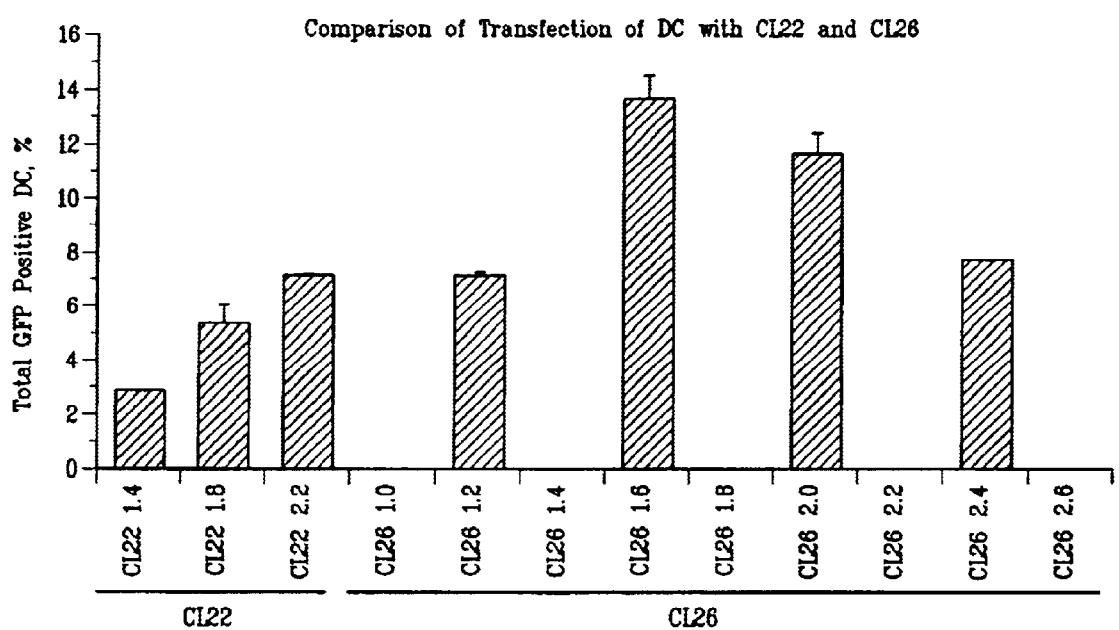
FIG. 17 shows results of transfection of dendritic cells with CL22 and CL26.
Figure 18:
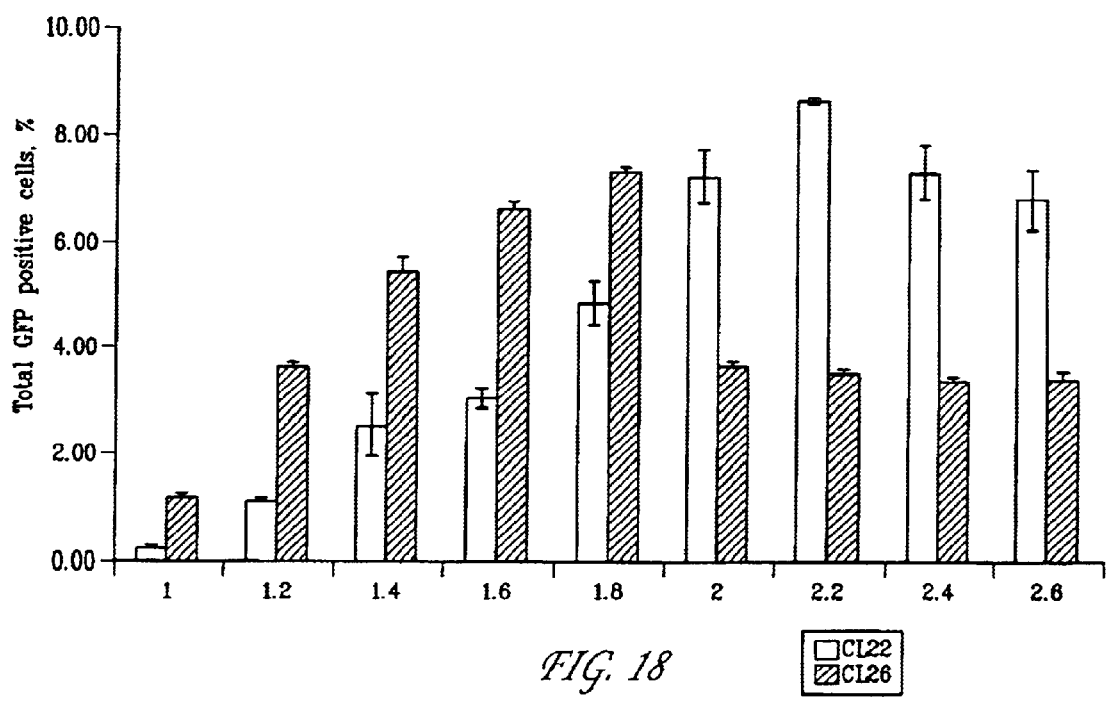
FIG. 18 shows results of transfection of dendritic cells with CL22 and CL26.

FIGS. 16–20 show comparisons of the transfection of dendritic cells with different polypeptides according to the invention. Dendritic cells were generated and transfected as described in Example 1. In the experiments described in this example, DNA (pEGFP-NI) was used at 1 mg. FIGS. 16–18 show results of transfections for three different preparations of dendritic cells in which the transfection efficiency with CL22-complexed DNA and CL26-complexed DNA was compared. In FIGS. 16 and 17, the peptide/DNA ratio was varied between 1.4 and 2.2 for CL22 and 1.0 and 2.6 for CL22. The optimal ratio is 1.6 mg CL26:1 mg DNA for CL26 and is in the range of 1.6–2.2 mg CL22:1 mg DNA for CL22. These data demonstrate that dendritic cells are transfected at a higher efficiency with CL26-complexed DNA as compared to CL22-complexed DNA.

In FIG. 18 dendritic cells were transfected with either CL22-complexed DNA or CL26-complexed DNA. The peptide/DNA ratio was varied between 1.0 and 2.6. In this experiment, dendritic cells are transfected at a higher efficiency with CL26-complexed DNA as compared to CL22-complexed DNA when the peptide/DNA ratio is between 1 and 1.8. However, when the peptide/DNA ratio is between 2 and 2.6, the efficiency off transfection is greater with CL22-complexed DNA as compared to CL26-complexed DNA.

Figure 19:
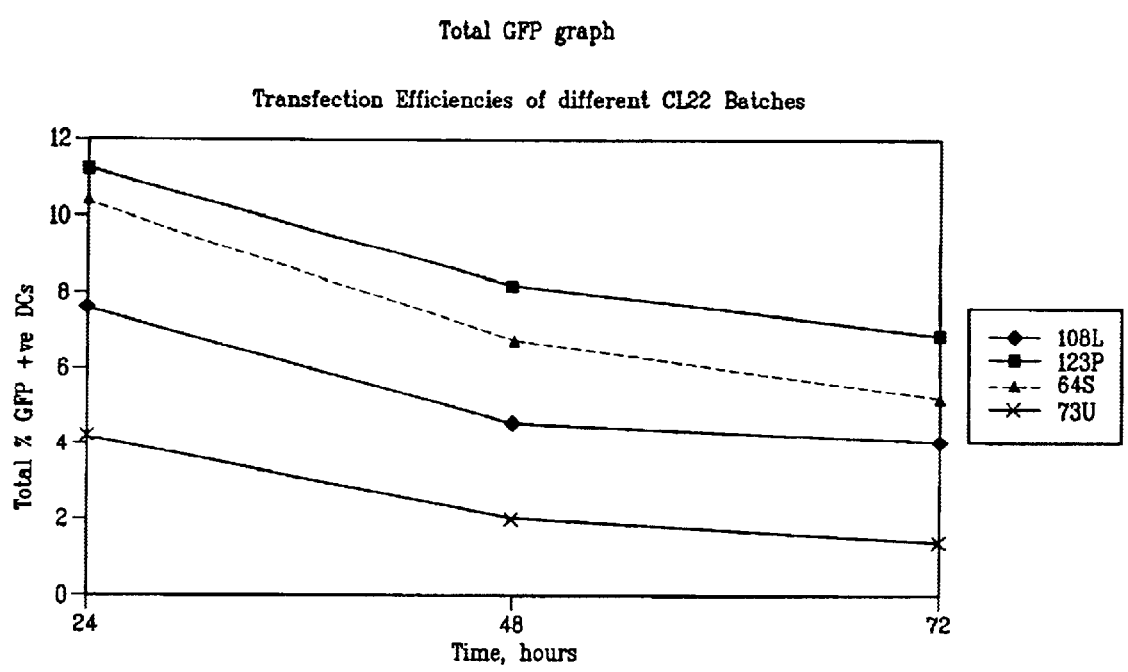
FIG. 19 is a comparison of the transfection efficiency of different preparations of CL22.

The variation in the relative ability of these two peptides to deliver DNA to dendritic cells can be explained, in part, by a variation in the transfection efficiency of different peptide preparations. FIG. 19 is a comparison of the transfection efficiency of different preparations of CL22 (designated as 108L, 123P, 64S and 73U. This figure demonstrates the variation in the transfection efficiency that is observed with different preparations of the CL22 peptide.

Figure 20:
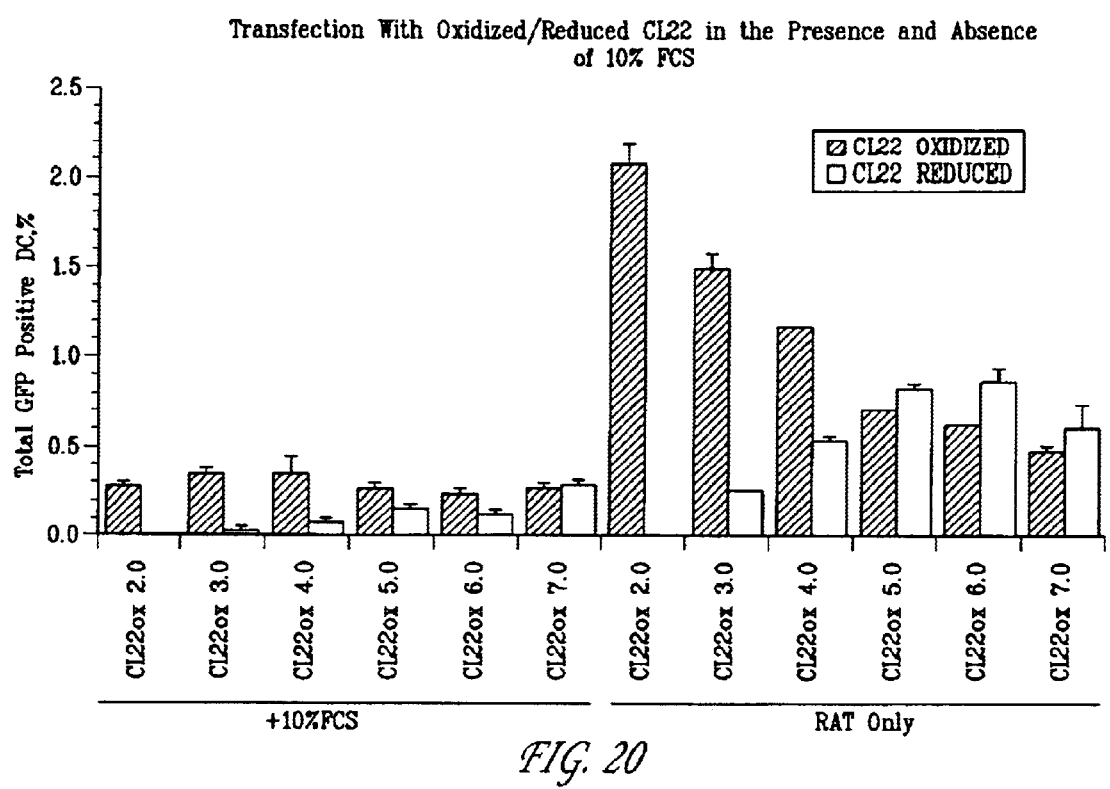
FIG. 20 is a bar graph of transfection efficiency for CL22 monomer and dimer in dendritic cells.

FIG. 20 compares the transfection efficiency of dendritic cells with CL22 in either monomeric (reduced) or dimeric (oxidized) form.

Blocking of Cysteine Thiol of K6CL22 Using N-Ethylmaleimide (NEM)

6.0 mg (1.5 $\mu$mol.) K6CL22 (batch 42A) was dissolved in 0.90 ml PBS and the cysteine reduced by adding 3.0 mg (20 $\mu$mol.) DTT in 0.10 ml water. After 2 h at room temperature the DTT was removed by gel filtration using a 1.6×30 cm column packed with Sephadex G25 Fine, and using 20 mM ammonium acetate, pH 5.0, as running buffer.

The fractions containing peptide were pooled, lyophilized and 4.0 mg freshly reduced peptide made up to 1.0 ml in PBS. The molar ratio of free thiol to peptide, as determined by an Ellman's assay (ref: Hermanson, GT (1996) "Bioconjugate Techniques" pp.88–90. (Published by Academic Press Ltd, London), was 0.88.

To 900 $\mu$l 4.0 mg/ml freshly reduced K6CL22, 100 $\mu$l water containing 0.8 mg (6.4 $\mu$mol) NEM was added. After 3 h incubation at 25° C. an Ellman's assay failed to detect the presence of free thiols. The excess NEM was removed by gel filtration, as described above, before lyophilization to give 2.1 mg thiol blocked peptide. Analysis by MALDI-TOF mass spectrometry gave an observed molecular weight of 4227.8 (expected MW 4227.0) for the blocked peptide; there was also a minor peak corresponding with the mass of the unblocked peptide, which may have been due to thiol deprotection during analysis.

Disulphide Formation to Give K6CL22 Dimers

To 1.0 ml of 5.0 mg/ml free thiol containing K6CL22 peptide in water was added 1.0 ml 0.1 M sodium borate, pH 8.0. The cysteine thiols were left to oxidize at 25° C. in a vial left open to the air. The progress of dimerisation was followed by observing the change in original retention time of the peptide by capillary electrophoresis. After 16 h the peptide was judged to have dimerised completely. Addition of 10 mM DTT to a peptide subsample reversed the observed shift in retention time. Dimer formation was also confirmed by gel filtration analysis using a Superdex Peptide (HR10/30) column. Finally, the sodium borate salt was removed by gel filtration in ammonium acetate followed by lyophilization, as described previously.

Transfection results demonstrate that CL22 monomer transfects dendritic cells poorly compared with CL22 dimer when the peptide/DNA ratio is between 2.0 and 4.0. Dendritic cells are transfected at a higher efficiency with CL22 dimer as compared to CL22 monomer in the presence or absence of FCS although the transfection efficiency is greatly reduced in the presence of FCS as compared to in the absence of FCS.

EXAMPLE 4

Presentation of Antigen by Human Dendritic Cells (DC) Transfected With Antigen Encoding Genes It was investigated whether DC transfected using the peptide/DNA complexes could present epitopes expressed from transgenes. The antigen used was influenza A nucleoprotein (A/NT/60/68).

A panel of donors was intially screened to determine the memory response to two specific NP peptides. The NP peptides, termed NP1 (ELRSRYWAI) (SEQ ID NO:19) and NP2i 6 (ILRGSVAHK) (SEQ ID NO:20) are known to be HLA-restricted to B8 and A3 respectively. The memory response was measured using fresh PBMC and an NP-peptide in an IFNgamma ELISpot assay exactly as described by Lalvani et al., 1997 (J. Exp. Med. 186:859–865). The following experiments were carried out with cells from donors who gave a positive response to at least one of the two peptides.

Figure 21:
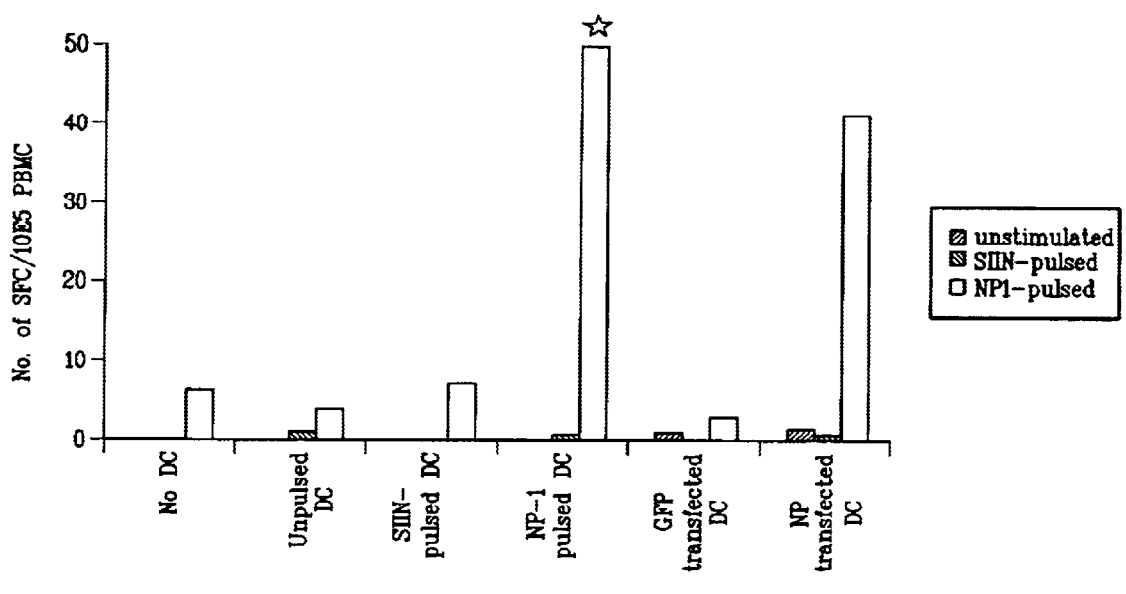
FIG. 21 is an IFNgamma ELISpot analysis of PBMC (HLA-B8) stimulated for 9 days with various DC preparations. The ELISpot was carried out using no stimulatory peptide, an irrelevant ovalbumin peptide (SIINFEKL) (SEQ ID NO:22) or the NP1 peptide. The number of spot forming cells (SFC) is plotted for each stimulation and assay condition. The results are the mean of triplicate samples. The star indicates that the spots were difficult to count and the true value is probably slightly higher than the bar suggests.
Figure 22:
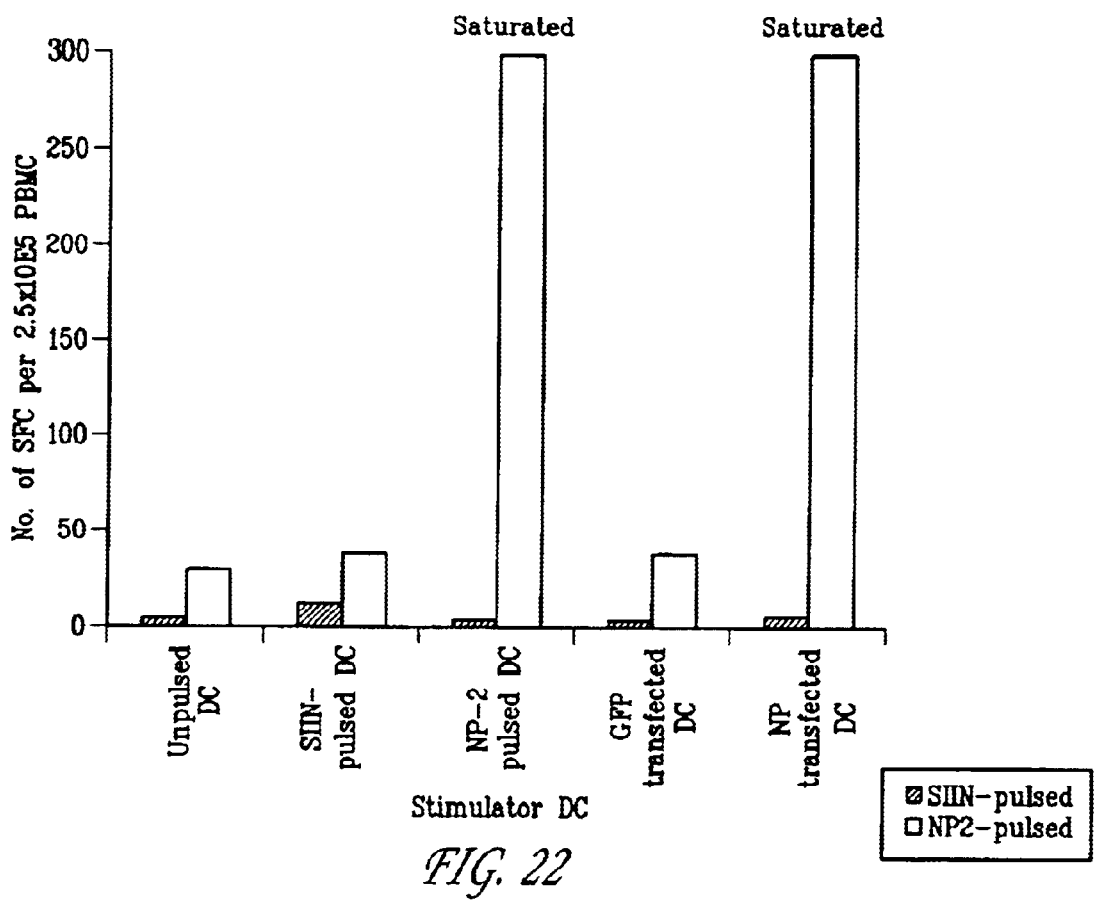
FIG. 22 is an IFNgamma ELISpot analysis of PBMC (HLA-A3) stimulated for 9 days with various DC preparations. The ELISpot was carried out using either an irrelevant C ovalbumin peptide (SIINFEKL) (SEQ ID NO:22) or the NP2 peptide. The number of spot forming cells (SFC) is plotted for each stimulation and assay condition. The results are the mean of triplicate samples. The responses from cells stimulated with either NP2 peptide-pulsed DC or NP transfected DC saturated the wells and were therefore greater than 300 SFC per $2.5 \times 10^5$ PBMC.
Figure 23:
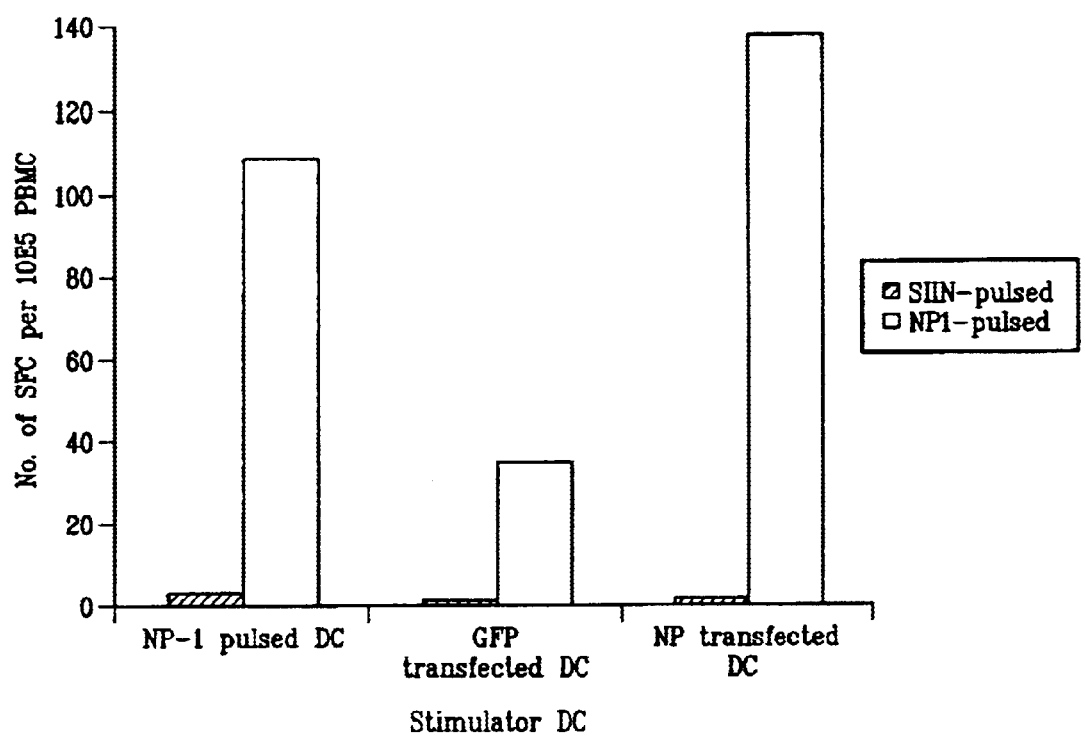
FIG. 23 is a IFNgamma ELISpot analysis of purifed CD8+ cells (HLA-B8) stimulated for 9 days with various DC preparations. The ELISpot was carried out using either an irrelevant ovalbumin peptide (SIINFEKL) or the NP1 peptide. The number of spot forming cells (SFC) is plotted for each stimulation and assay condition. The results are the mean of triplicate samples.
Figure 27:
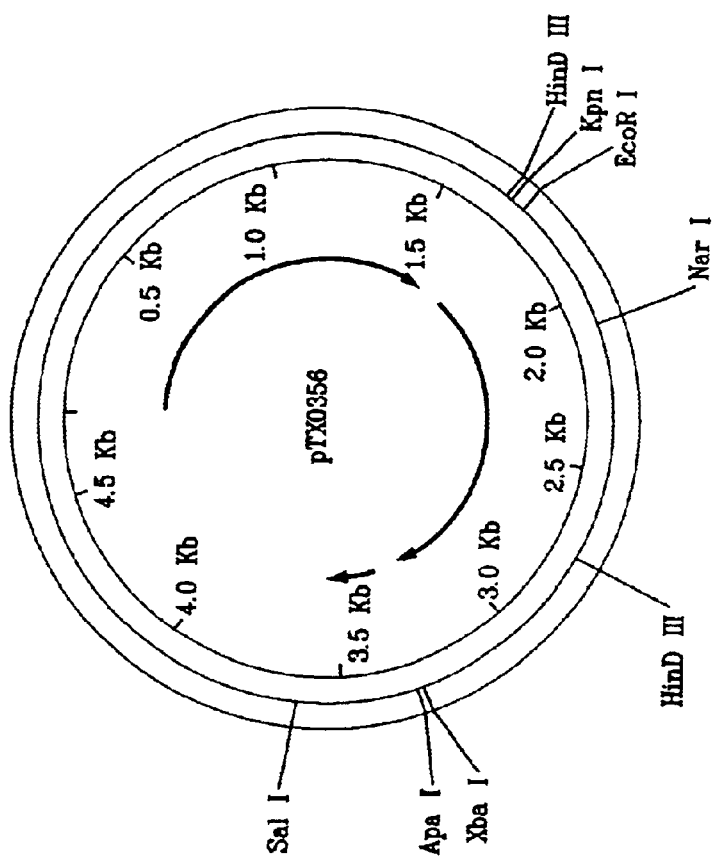
FIG. 27 shows pTX0356—The influenza A nucleoprotein expression plasmid.

DC were prepared from the donors (50–100 ml fresh blood), in DC medium (RPMI-1640 supplemented with 2 mM L-glutamine, 50 U/ml penicillin, 50 $\mu$g/ml streptomycin and 10% heat-inactivated fetal calf serum), as described previously and were transfected on day 4 with GFP or NP expressing constructs (pEGFP-NI, Clontech or pTX0356, FIG. 27, respectively). The following day, transfected DC (stimulators) were incubated with freshly prepared PBMC or purified CD8+ T cells (purified using Dynabeads M450 CD8 and DETACHaBEADS according to the manufacturer's protocols, DYNAL). As controls, NP peptide-pulsed, irrelevant peptide-pulsed, unpulsed and irrelevant DNA (GFP) transfected DC were also incubated with the appropriate responder population. 2×10$^6$ PBMC or 0.5–1×10$^6$ CD8+ T cells were mixed with the DC at a ratio of 10:1, in 2 ml of DC medium in 24-well dishes. The co-cultures were maintained for 9 days with IL-7 (10 ng/ml) added on day 0 and IL-2 (10 U/ml) added on days 3 and 7. On day 9 an ELISpot assay was carried out as described below. FIGS. 21 and 22 show the results of two independent experiments using PBMC as the stimulated cells and FIG. 23 shows the ELISpot results when CD8+ cells were used as the responding cell population. These results show that both the peptide-pulsed and NP-transfected DC stimulate the responding population to specifically increase the proportion of cells responsive to a specific NP peptide. There is no specific stimulation with the control DC. Thus stimulation of either PBMC or CD8+ T cells with transfected DC results in stimulation of NP peptide-specific T cells. The T cells are presumed to be CD8$^+$ T cells due to the use of an HLA Class I restricted peptide in the ELISpot assay.

Figure 24:
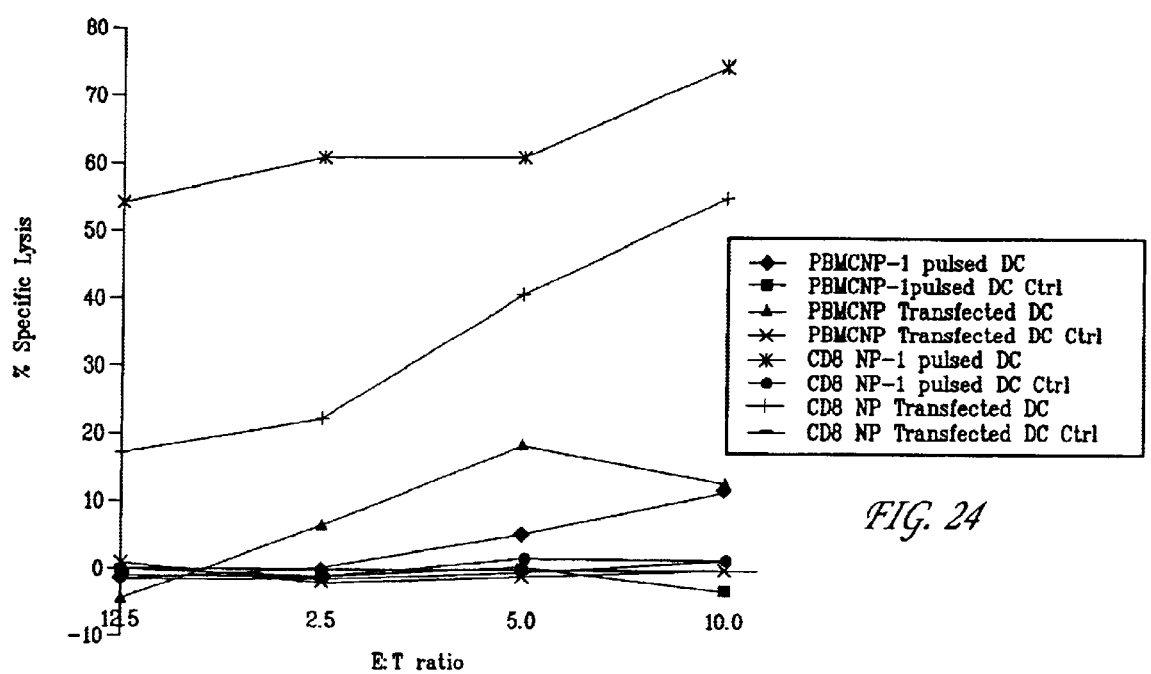
FIG. 24 shows the peptide-specific cytotoxic activity of PBMC or CD8+ populations (HLA A3) stimulated with peptide-pulsed or transfected DC. The target cells are PHA blasts pulsed with NP2 peptide or unpulsed in the case of controls (Ctrl).
Figure 25:
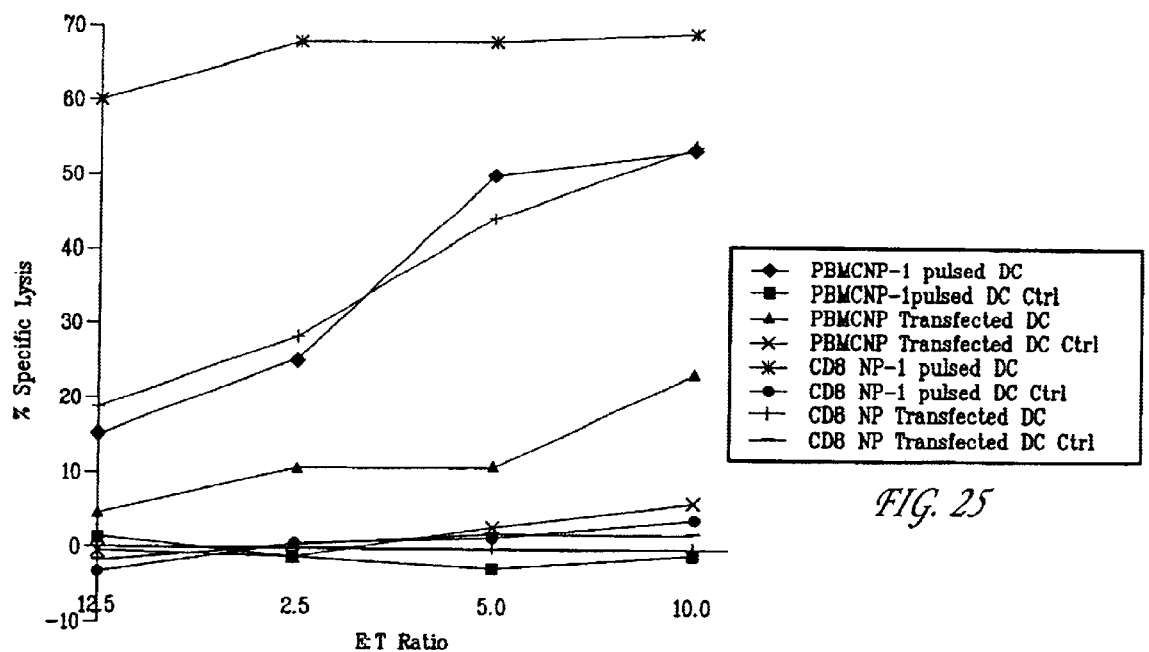
FIG. 25 shows the peptide-specific cytotoxic activity of PBMC or CD8+ populations (HLA B8) stimulated with peptide-pulsed or transfected DC. The target cells are PHA blasts pulsed with NP1 peptide or unpulsed in the case of controls (Ctrl).

To demonstrate that NP-specific CTLs have been stimulated a $^{51}$Cr-release assay was carried out after the responders had received a further round of stimulation. The second round of stimulation was carried out in an identical manner to the first. The results of the CTL assays are shown in FIGS. 24 & 25. Increased target cell lysis is observed with T cells incubated with NP peptide-pulsed DC or DC transfected with the NP expressing construct (pTX0356). Thus stimulation of the PBMC or CD8$^+$ cell populations with transfected DC results in an increase in the anti-NP specific cytotoxic activity of the resultant population.

Materials and Methods

DC Transfection

DC were transfected in 24 well plates with 3×10$^5$ cells per well and CL22-NPPk complexes. CL22-NPPk complexes were made by mixing equal volumes of CL22 peptide and pTX0356 DNA, both in HBS (10 mM HEPES, pH 7.4, 150 mM NaCl), such that the final mix has a DNA concentration of 20 $\mu$g/ml and a peptide to DNA mass ratio of 2:1. 125 $\mu$l complex and 4 $\mu$l 10 mM chloroquine (pH 7.4) were added to the well in such a manner as not to mix the two solutions. 871 µl of cells in the appropriate serum-free medium was added to the well so that all three solutions mix. The plates were centrifuged at 200 g for 5 mins and were incubated at 37° C., 5% $CO_2$ for 90 min. The medium was then removed from each well, centrifuged at 200 g for 5 min to pellet the cells in suspension, the supernatant was removed and the pellet resuspended in growth medium (usually RAB).

The resuspended cells were returned to the well from which they were removed and the plates were incubated at 37° C., 5% $CO_2$ overnight, prior to use in the stimulation cultures.

DC Peptide-pulsing

DC were pulsed with 100 µM peptide at a cell concentration of $1-2 \times 10^6$/ml in the presence of 3 µg/ml β-2 microglobulin for 4h at 20° C. in OPTI-MEM. The cells are then washed thoroughly prior to use.

ELISpot Assay

The ELISpot plates were prepared as follows: 96-well PVD-backed plates (MAIP-545, Millipore) were coated with 15 µg/ml anti-INFgamma mAb 1-DIK (100 ul per well, MABTECH) overnight at 4° C. The wells were washed 6 times with RPMI-1640 and blocked with RPMI-1640 supplemented with 2 mM L-glutamine, 50 U/ml penicillin, 50 µg/ml streptomycin and 5% heat-inactivated pooled human AB serum (RAB) for 1 h. $0.5-5 \times 10^5$ PBMC stimulated with 2 µM peptide were added to each well and the plates were incubated for 6–14h at 37° C., 5% $CO_2$. The assays were stopped by shaking off the contents of the wells and washing 6 times with PBS, 0.05% Tween-20. A 100 µl of a 1 µg/ml stock f biotinylated anti-IFNgamma mAb 7-B6-1 biotin (MABTECH) in PBS/Tween was added to each well and the plates were incubated for 3 h. The plates were wash 6 times with PBS/Tween-20 and 100 µl of a 1:800 dilution of streptavidin peroxidase conjugate was added. The plate was incubated for a further 2 h at room temperature. A PBS/Tween wash was carried out six times and then 200 µl of chromogenic peroxidase substrate (Vector AEC kit) was added. Once maximal spot development was obtained (5–30min), the plates were washed with tap water, air-dried and the spots were counted under a microstereoscope (only large spots with fuzzy borders were scored: SFC (spot forming cells)). Responses were considered positive if a minimum of 5 SFC were present per well and this number was at least twice that in negative control wells.

$^{51}$Cr-release Assay

The $^{51}$Cr-release assays were carried as follows: Target cells, PHA-blasts ($10^6$ to $10^7$), were prepared in OPTI-MEM medium (Gibco-BRL) and split into two aliquots. The PHA-blasts were prepared by incubating $10^7$ PBMC with 2 µg/ml PHA in 10 ml medium in an upright T25 for 3–5 days. 100 µM peptide was added to one PHA-blast aliquot only and 100–200 µCi $^{51}$Cr was added to each aliquot. The cells were incubated at 37° C., 5% $CO_2$ for 90 min with gentle agitation every 20 mins. Cells were washed 3 times with 15 ml OPTI-MEM and were resuspended in 1 ml RAB. The cells were counted and diluted to $10^4$ to $10^5$ cells per ml, depending on the number of effectors available. The effector cells, i.e. the stimulated T cells, were washed once in RAB, counted and diluted to the appropriate concentration. The cells were serially diluted into 96-well U-bottom plates in triplicate (0.1 ml/well). An equal volume of target cells was added to the well to give the desired effector:target ratio. The plate(s) was then centrifuged at 60 g for 5 min. For spontaneous release, only targets were added and the well was made up to the equivalent volume with medium, for maximum release 0.1 ml of 2% SDS was added to wells containing targets only. Cells were incubated at 37° C., 5% $CO_2$ for 4 hr. 30 µl of the supernatant was taken from each well and added to the filter plates (LumaPlate™96, Packard, 6005164), dried and then counted in a Packard Topcount. The percentage specific lysis is calculated as ((experimental release-spontaneous release)/(maximum release-spontaneous release))×100.

EXAMPLE 5

Immunisation of Mice With Transfected Primary Murine Dendritic Cells

In order to determine whether DC transfected with peptide/DNA complexes are able to generate an anti-transgene immune response in vivo, transfected primary murine DC were administered to mice and the resulting immune responses measured. The antigen used was influenza A nucleoprotein (A/NT/80/68), and the plasmid DNA encoding it was pTX0356.

Dendritic cells (bmDC) were generated from the bone marrow of Balb/c mice (see method below). The resultant bmDC were of typical veiled cell morphology and were only lightly adherent to plastic. FACs analysis revealed the presence of typical dendritic cell phenotype: MHC $I^{hi}$, MHC $II^{hi}$, $CD40^+$, $CD80^+$, $CD86^+$, $DEC-205^+$. The bmDC were transfected on day 7 of culture using the protocol below. Following transfection, the dendritic cells were more adherent. 8–10 week old Balb/c mice were immunised intravenously with $3 \times 10^5$ transfected bmDC (pTX0356), NP peptide-pulsed bmDC ($NP_{147-155}$) or untreated bmDC. The cells were administered suspended in 100 µl PBS on days 0, 7 and 28. Separate dendritic cell/transfection preparations were used for each administration.

Figure 26:
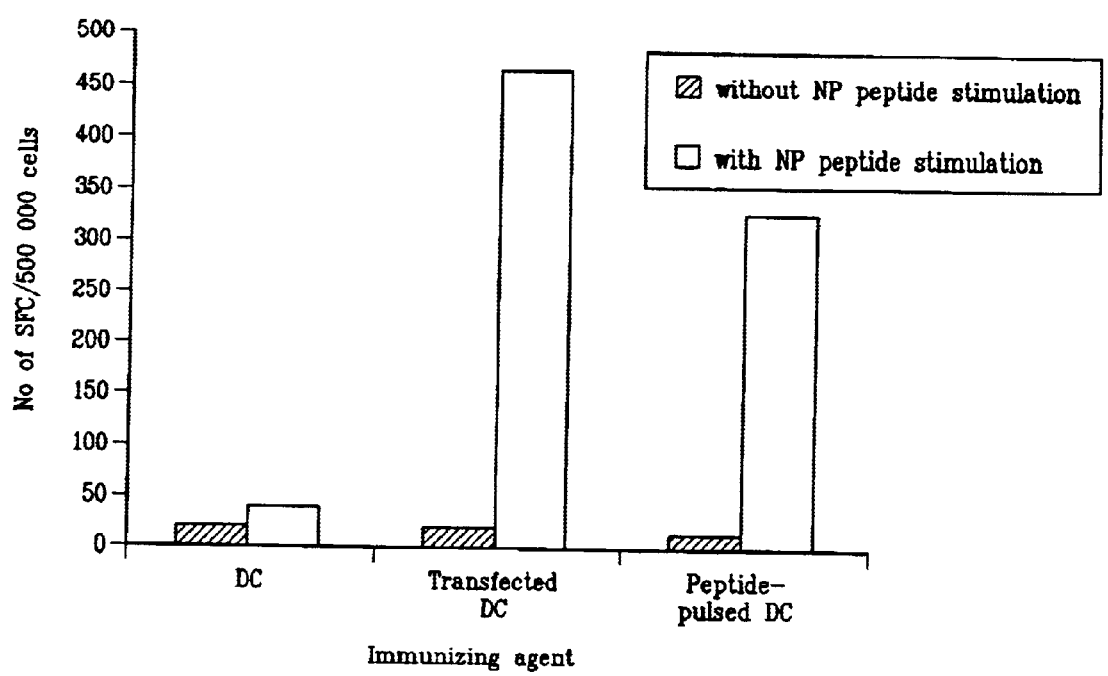
FIG. 26 is an IFNgamma ELISpot analysis of splenocytes from mice immunised intravenously with bone marrow derived dendritic cells. The ELISpot was carried out using no peptide stimulation or $NP_{147-155}$ peptide stimulation. The number of spot forming cells (SFC) is plotted. The results are the mean from two mice, each analysed in triplicate.

To assess transfection efficiency, parallel transfections were performed using plasmid DNA (pEGFP-NI, Clontech) encoding the green fluorescent protein, GFP. The three transfections gave transfection efficiencies of around 1%, 0.1% and 1.4% for cells used at days 0, 7 and 28 respectively. The mice were sacrificed on day 35 and their spleens were immediately removed. Single cells suspensions were prepared and an ELISpot assay was carried out to assess the number of NP-peptide specific T cells in each preparation (see method below). Based on the number of spots, intravenous injection of CL22-NPPK transfected dendritic cells provides an efficient means of inducing a CD8-based immune response in an animal model (FIG. 26). This indicates that in vivo administration of bmDC transfected by a CL22/DNA complex, containing a DNA construct expressing an antigen encoding gene, results in cellular immune responses to MHC Class I-restricted epitopes.

Materials and Methods

Murine Primary Dendritic Cell (bmDC) Culture

Bone marrow derived dendritic cells were prepared and cultured in accordance with the procedure of Tüting et al (Tüting T., DeLeo A. B., Lotze M. T. & Storkus W. J. 1997 Genetically modified bone marrow-derived dendritic cells expressing tumor-associated viral or "self" antigens induce antitumor immunity in vivo. *Eur. J. Immunol.* 27: 2702–2707).

Murine bmDC Transfection

CL22-NPPK complexes were set up at a peptide to DNA mass ratio of 1.8:1, at a DNA concentration of 20 µg/ml in HBS, and were incubated with $3\times10^5$ dendritic cells/well of a 24 well culture plate in a total volume of 1 ml containing 20 µM chloroquine. The plates were centrifuged for 30 sec @ 1400 rpm in a Sorval RT 6000D centrifuge prior to incubation at 37° C., 5% $CO_2$ for 2 h. Cells were harvested by gentle pipetting, washed twice with PBS and adjusted to $3\times10^5$ cells/100 µl in PBS and were immediately administered to the mice or were cultured.

Immunisation

8–10 week old Balb/c mice were immunised intravenously with $3\times10^5$ transfected dendritic cells suspended in 100 µl PBS on days 0, 7 and 28. Separate dendritic cell/transfection preps were used for each day.

Preparation of Spleen Cells and Performance of the ELISpot Assay

Spleens were individually macerated through 0.4 µm nylon membranes and cell clumps were disrupted by repeated pipetting following which erythrocytes were lysed with ammonium chloride. Cells were resuspended in complete medium (RPMI-1640, 2 mM L-Glutamine, 5% FCS, 50 µM β-mercaptoethanol, 10 mM HEPES) and adjusted to give $5\times10^6$ cells/ml. 100 µl of cells ($5\times10^5$ cells) were added/well to wells of a 96 well plate (Millipore Multiscreen HA plate, coated overnight with primary anti-mouse IFNγ Ab, 5 µg/µl, Pharmingen 18181D, and blocked by a 60 min incubation with 5% BSA) and were incubated in the presence or absence of NP Class I peptide, $NP_{147\text{-}155}$ (amino acids 147–155, TYQRTRALV) (SEQ ID NO:21) (1 µg/ml), for 20 h at 37° C., 5% $CO_2$. Cells were lysed with distilled water (2 min) prior to washing with PBS containing 0.05% TWEEN 20. Plates were then incubated with biotinylated rat anti-mouse IFNγ antibody (Pharmingen 18112D) overnight at 4° C. After washing, plates were incubated with avidin-peroxidase conjugate (Sigma, 2µg/ml) for 2 h at room temperature, and following extensive washing AEC substrate (Vector Laboratories) was added (in accordance with the manufacturers instructions) for 4 min. Washing with water brought the reaction to a halt. After air-drying, spots were counted using an image analyser.

Other Embodiments

Other embodiments are within the following claims. The contents of the references referred to herein are incorporated by reference thereto in their entireties.

---

What is claimed is:

1. A method of eliciting an immune response in a mammal comprising intramuscularly or subcutaneously administering to said mammal a mixture comprising (i) a nucleic acid encoding at least a first immunogenic epitope operably linked to transcriptional regulatory elements for expression of said immunogenic epitope and (ii) a peptide comprising a second immunogenic epitope such that the nucleic acid and the peptide are taken up by and the nucleic acid is expressed in a professional antigen presenting cell of the mammal as said first immunogenic epitope, wherein an immune response is elicited in the mammal to said first immunogenic epitope and said second immunogenic epitope, provided that said mixture is not a virus.

2. The method of claim 1 wherein the mixture administered comprises a complex comprising (i) said nucleic acid encoding at least a first immunogenic epitope and (ii) said peptide comprising said second immunogenic epitope wherein said peptide further comprises a nucleic acid-binding sequence, wherein said complex is taken up by and the nucleic acid expressed in a professional antigen presenting cell of said mammal.

3. The method of claim 1 wherein said second epitope is present in a two-domain polypeptide comprising said second immunogenic epitope fused to a nucleic acid-binding amino acid sequence, wherein upon administration of said nucleic acid to said mammal, an immune response is elicited to said immunogenic epitope.

4. A method of eliciting an immune response in a mammal comprising administering to said mammal professional antigen presenting cells to which a mixture comprising (i) a recombinant nucleic acid encoding a first immunogenic epitope operably linked to transcriptional regulatory elements for expression of said immunogenic epitope, and (ii) a peptide comprising a second immunogenic epitope that is not normally present in said antigen presenting cells has been delivered and wherein upon administration of said antigen presenting cells an immune response is elicited in said mammal to said first immunogenic epitope and said second immunogenic epitope provided that said nucleic acid and said peptide are not delivered to said antigen presenting cells in the form of a virus.

5. The method of claim 1 or 4 wherein said first immunogenic epitope and said second immunogenic epitope are the same epitope.

6. The method of claim 1 or 4 wherein said first immunogenic epitope and said second immunogenic epitope are different epitopes.

7. The method of claim 6 wherein said first immunogenic epitope is an epitope of a first polypeptide and said second immunogenic epitope is an epitope of a second polypeptide.

8. The method of claim 1 or 4 wherein said first immunogenic epitope and said second immunogenic epitope are epitopes of a single polypeptide.

9. The method of claim 8 wherein said first immunogenic epitope and said second immunogenic epitope are epitopes of a single organism.

10. The method of claim 1 or 4 wherein the nucleic acid encodes more than one immunogenic epitope.

11. The method of claim 1 or 4 wherein said first immunogenic epitope and said second immunogenic epitope are from an infectious agent.

12. The method of claim 1 or 4 wherein said first immunogenic epitope and said second immunogenic epitope are present in the mammal during the course of a disease.

13. The method of claim 12 wherein the disease is caused by an infectious pathogen and said nucleic acid comprises an open reading frame from the pathogen's genome.

14. The method of claim 13 wherein said nucleic acid comprises multiple open reading frames from the pathogen's genome.

15. The method of claim 1 or 4 wherein the nucleic acid comprises a multi-gene construct.

16. The method of claim 15 wherein the genes of said multi-gene construct are coordinately expressed.

17. The method of claim 1 or 4, further comprising a nucleic acid encoding a third immunogenic epitope, wherein said first immunogenic epitope is present in a mammal during the course of a first disease and said third immunogenic epitope is present in a mammal during the course of a second disease, and said administration elicits an immune response against said first immunogenic epitope and said third immunogenic epitope.

18. The method of claim 17 wherein said first disease is caused by a first pathogen and said second disease is caused by a second pathogen.

19. The method of claim 1 or 4, wherein said first and/or said second epitope comprises an immunodominant epitope of influenza NP.

20. The method of claim 1 or 4, said nucleic acid further comprising a locus control region (LCR) which restricts expression of a coding sequence that is operatively linked thereto to professional antigen presenting cells.

21. The method of claim 20, said locus control region being the MHC class II LCR or the Ig LCR.

22. The method of claim 1 or 4 wherein said peptide further comprises at least one additional immunogenic epitope.

23. The method of claim 4 wherein said second epitope is present in a two-domain polypeptide comprising said second immunogenic epitope fused to a nucleic acid-binding amino acid sequence, wherein upon administration of said dentritic cell to said mammal, an immune response is elicited to said immunogenic epitope.

24. The method of claim 13 or 23 wherein said second immunogenic epitope is from the same organism as at least the first immunogenic epitope.

25. A method of eliciting an immune response in a mammal comprising intramuscularly or subcutaneously administering to said mammal a complex comprising (i) a nucleic acid and (ii) a peptide comprising a first immunogenic epitope and a nucleic acid binding sequence such that said nucleic acid and said peptide are taken up by a professional antigen presenting cell of said mammal, wherein an immune response is elicited in said mammal to said first immunogenic epitope, provided that said complex is not a virus.

26. The method of claim 25, wherein said first immunogenic epitope is from an infectious agent or organism.

27. The method of claim 25 wherein said first immunogenic epitope is present in the mammal during the course of a disease.

28. The method of claim 25, said complex further comprising a second immunogenic epitope.

29. The method of claim 28, said first immunogenic epitope and said second immunogenic epitope being epitopes of the same antigen.

30. The method of claim 28, said first immunogenic epitope and said second immunogenic epitope being epitopes of the same infectious agent or organism.

31. The method of claim 25 or 28, said first immunogenic epitope and/or said second immunogenic epitope comprising an immunodominant epitope of influenza NP.

32. The method of claim 25 wherein said peptide further comprises at least one additional immunogenic epitope.

33. A composition for eliciting an immune response in a mammal comprising a complex comprising (i) a vector comprising a nucleic acid encoding at least a first immunogenic epitope operably linked to transcriptional regulatory elements and a sequence which permits maintenance of said vector in episomal form, and (ii) a peptide containing a second immunogenic epitope and a nucleic acid binding sequence, provided that said complex is not a virus.

34. The composition of claim 33 wherein said complex is adapted for selective expression in antigen presenting cells by the presence in the vector of a locus control region which restricts expression of a nucleic acid coding sequence that is operatively linked thereto to professional antigen presenting cells.

35. The composition of claim 34, said locus control region being one of the MHC class II LCR or the Ig LCR.

36. The composition of claim 33 wherein said second immunogenic epitope is from the same organism as the first immunogenic epitope.

37. The composition of claim 36, said second epitope comprising an immunodominant epitope of influenza NP.

38. The method of claim 33 wherein said peptide further comprises at least one additional immunogenic epitope.

39. A composition for eliciting an immune response in a mammal comprising an antigen presenting cell comprising (i) a vector comprising a nucleic acid encoding at least a first immunogenic epitope, a sequence which permits maintenance of said vector in episomal form, and a gene control element for obtaining selective expression of said vector sequences in an antigen presenting cell operably linked to said nucleic acid encoding said first immunogenic epitope, provided that said vector is not a virus, and (ii) a second immunogenic epitope.

40. The composition of claim 39, said gene control element comprising a locus control region which restricts expression of a coding sequence that is operatively linked thereto to professional antigen presenting cells.

41. The composition of claim 33 or 39, said sequence which permits maintenance of said vector in episomal form comprising a papilloma virus sequence.

42. The composition of claim 41, said papilloma virus sequence comprising a minimal origin of replication and a minimal maintenance element.

43. The composition of claim 41, said papilloma virus sequence further comprising the E1 and E2 genes.

44. The composition of claim 41, said papilloma virus sequence being from bovine papilloma virus.

45. The composition of claim 33 or 39 wherein said nucleic acid encodes more than one immunogenic epitope.

46. The composition of claim 33 or 39 wherein said immunogenic epitopes are immunogenic epitopes of an infectious agent.

47. The composition of claim 33 or 39 wherein said immunogenic epitopes are present in the mammal during the course of a disease.

48. The composition of claim 47 wherein the disease is caused by an infectious pathogen and said nucleic acid comprises an open reading frame from the pathogen's genome.

49. The composition of claim 33 or 39 wherein the nucleic acid comprises a multi-gene construct.

50. The composition of claim 49 wherein said nucleic acid encodes a first immunogenic epitope that is present in a mammal during the course of a first disease and wherein said nucleic acid further encodes a third immunogenic epitope that is present in a mammal during the course of a second disease, thereby eliciting an immune response against said first epitope and said third immunogenic epitope.

51. The composition of claim 50 wherein said first disease is caused by a first pathogen and said second disease is caused by a second pathogen.

52. The composition of claim 33 or 39 wherein said first immunogenic epitope or said second immunogenic epitope comprises an immunodominant epitope of influenza NP.

53. The method of claim 39 wherein said peptide further comprises at least one additional immunogenic epitope.

* * * * *

SEQUENCE LISTING

```
<160> NUMBER OF SEQ ID NOS:  22

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 1

Thr Arg Arg Ala Trp Arg Arg Ala Lys Arg Arg Ala Ala Arg Arg Cys
 1               5                  10                  15

Gly Val Ser Ala Arg Arg Ala Ala Arg Arg Ala Trp Arg Arg Glu
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 2

Ala Lys Lys Trp Ala Lys Lys Ala Ala Lys Lys Ala Ser Val Gly Cys
 1               5                  10                  15

Lys Lys Ala Ala Lys Lys Glu Ala Lys Lys Trp Ala Lys Lys Thr
            20                  25                  30

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Novel
      Sequence
```

```
<221> NAME/KEY: UNSURE
<222> LOCATION: (3)
<223> OTHER INFORMATION: X is Serine, Threonine or Proline
<221> NAME/KEY: UNSURE
<222> LOCATION: (7)
<223> OTHER INFORMATION: X is Alanine or Valine
<221> NAME/KEY: UNSURE
<222> LOCATION: (8)
<223> OTHER INFORMATION: X is Alanine, Threonine or Proline
<221> NAME/KEY: UNSURE
<222> LOCATION: (9)
<223> OTHER INFORMATION: X is Lysine, Alanine, Threonine or Valine
<221> NAME/KEY: UNSURE
<222> LOCATION: (12)
<223> OTHER INFORMATION: X is Alanine or Valine

<400> SEQUENCE: 3

Lys Lys Xaa Pro Lys Lys Xaa Xaa Xaa Pro Ala Xaa
 1               5                  10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)
<223> OTHER INFORMATION: X is Alanine or Valine

<400> SEQUENCE: 4

Xaa Lys Ser Pro Ala Lys Ala Lys Ala
 1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)
<223> OTHER INFORMATION: X is Lysine or Arginine
<221> NAME/KEY: UNSURE
<222> LOCATION: (2)
<223> OTHER INFORMATION: X is Alanine or Threonine
<221> NAME/KEY: UNSURE
<222> LOCATION: (10)
<223> OTHER INFORMATION: X is Proline, Alanine or Serine
<221> NAME/KEY: UNSURE
<222> LOCATION: (12)
<223> OTHER INFORMATION: X is Lysine, Threonine or Valine

<400> SEQUENCE: 5

Xaa Xaa Val Lys Pro Lys Ala Ala Lys Xaa Lys Xaa
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 6

Pro Lys Lys Lys Arg Lys Val Gln
 1               5
```

```
<210> SEQ ID NO 7
<211> LENGTH: 61
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 7

Pro Lys Lys Lys Arg Lys Val Glu Lys Lys Ser Pro Lys Lys Ala Lys
       1               5                  10                  15
      Lys Pro Ala Ala Lys Ser Pro Ala Lys Ala Lys Ala Lys Ala Val Lys
                   20                  25                  30
      Pro Lys Ala Ala Lys Pro Lys Lys Pro Lys Lys Arg Lys Val Glu
                   35                  40                  45
      Lys Lys Ser Pro Lys Lys Ala Lys Lys Pro Ala Ala Cys
              50                  55                  60

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 8

Lys Ala Val Lys Pro Lys Ala Ala Lys Pro Lys Lys Pro Lys Lys Lys
 1               5                  10                  15

Arg Lys Val Glu Lys Lys Ser Pro Lys Lys Ala Lys Lys Pro Ala Ala
                20                  25                  30

Cys

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 9

Lys Lys Ser Pro Lys Lys Ala Lys Lys Pro Ala Ala Lys Lys Ser Pro
 1               5                  10                  15

Lys Lys Ala Lys Lys Pro Ala Ala Cys
                20                  25

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 10

Lys Lys Ser Pro Lys Lys Ala Lys Lys Pro Ala Ala Lys Lys Ser Pro
 1               5                  10                  15

Lys Lys Ala Lys Lys Pro Ala Ala Lys Lys Ser Pro Lys Lys Ala Lys
                20                  25                  30

Lys Pro Ala Ala Cys
         35

<210> SEQ ID NO 11
<211> LENGTH: 49
<212> TYPE: PRT
```

```
<213> ORGANISM: Artificial Sequence
<220> FEATURE:
<223> OTHER INFORMATION: Description of Artificial Sequence: Novel
      Sequence

<400> SEQUENCE: 11

Lys Lys Ser Pro Lys Lys Ala Lys Lys Pro Ala Ala Lys Lys Ser Pro
 1               5                  10                  15

Lys Lys Ala Lys Lys Pro Ala Ala Lys Lys Ser Pro Lys Lys Ala Lys
            20                  25                  30

Lys Pro Ala Ala Lys Lys Ser Pro Lys Lys Ala Lys Lys Pro Ala Ala
        35                  40                  45

Cys

<210> SEQ ID NO 12
<211> LENGTH: 12
<212> TYPE: DNA
<213> ORGANISM: Papillomavirus

<400> SEQUENCE: 12
accgttgccg gt                                                              12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence:
      Permutations of E2 Binding Site
<221> NAME/KEY: unsure
<222> LOCATION: (4)..(9)
<223> OTHER INFORMATION: N is any nucleotide

<400> SEQUENCE: 13
accnnnnnng gt                                                              12

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 14

Gly Gly Ala Gly Ala Gly Gly Ala
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 15

Gly Gly Ala Gly Ala Gly Gly Gly Ala
 1               5

<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence: Novel
```

Sequence

<400> SEQUENCE: 16

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Asn Ile Leu
            20                  25                  30

Lys Gly Lys
        35

<210> SEQ ID NO 17
<211> LENGTH: 105
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
aaaaaaaaga aaaaaaaagg tggtttgctg ggtttctggc gtggtgaaaa cggtcgtaaa      60
acccgttctg cttacgaacg tatgtgcaac atcctgaaag gtaaa                    105

<210> SEQ ID NO 18
<211> LENGTH: 41
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 18

Lys Lys Lys Lys Lys Lys Lys Lys Lys Lys Gly Gly Phe Leu
1               5                   10                  15

Gly Phe Trp Arg Gly Glu Asn Gly Arg Lys Thr Arg Ser Ala Tyr Glu
            20                  25                  30

Arg Met Cys Asn Ile Leu Lys Gly Lys
        35                  40

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 19

Glu Leu Arg Ser Arg Tyr Trp Ala Ile
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 20

Ile Leu Arg Gly Ser Val Ala His Lys
1               5

<210> SEQ ID NO 21
<211> LENGTH: 9

```
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 21

Thr Tyr Gln Arg Thr Arg Ala Leu Val
  1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 22

Ser Ile Ile Asn Phe Glu Lys Leu
  1               5
```